US012775004B2

(12) United States Patent
Cohen Solal et al.

(10) Patent No.: US 12,775,004 B2
(45) Date of Patent: Oct. 27, 2026

(54) METHODS OF THERAPEUTIC PROGNOSTICATION

(71) Applicant: GENETIKAPLUS LTD., Tel Aviv (IL)

(72) Inventors: Talia Cohen Solal, Bat Yam (IL); Daphna Laifenfeld, Haifa (IL); Erez Nitzan, Modiin-Maccabim-Reut (IL); Yishai Avior, Jerusalem (IL)

(73) Assignee: GENETIKAPLUS LTD., Tel Aviv (IL)

( * ) Notice: Subject to any disclaimer, the term of this patent is extended or adjusted under 35 U.S.C. 154(b) by 794 days.

(21) Appl. No.: 17/800,096

(22) PCT Filed: Feb. 16, 2021

(86) PCT No.: PCT/IL2021/050183
§ 371 (c)(1),
(2) Date: Aug. 16, 2022

(87) PCT Pub. No.: WO2021/161323
PCT Pub. Date: Aug. 19, 2021

(65) Prior Publication Data

US 2023/0094922 A1 Mar. 30, 2023

Related U.S. Application Data

(60) Provisional application No. 62/977,308, filed on Feb. 16, 2020.

(51) Int. Cl.

| | |
|---|---|
| ***G01N 33/50*** | (2006.01) |
| ***A61K 31/137*** | (2006.01) |
| ***A61K 31/343*** | (2006.01) |
| ***A61K 35/17*** | (2025.01) |
| ***A61K 35/30*** | (2015.01) |
| ***A61K 35/545*** | (2015.01) |
| ***A61P 35/00*** | (2006.01) |
| ***C12N 5/0793*** | (2010.01) |
| *A61K 31/135* | (2006.01) |
| *A61K 31/55* | (2006.01) |

(52) U.S. Cl.
CPC ....... *G01N 33/5058* (2013.01); *A61K 31/343* (2013.01); *A61K 35/17* (2013.01); *A61K 35/30* (2013.01); *A61K 35/545* (2013.01); *A61P 35/00* (2018.01); *C12N 5/0619* (2013.01); *A61K 31/135* (2013.01); *A61K 31/137* (2013.01); *A61K 31/55* (2013.01); *C12N 2503/00* (2013.01); *C12N 2506/11* (2013.01); *C12N 2506/45* (2013.01)

(58) Field of Classification Search
CPC .... G01N 33/5058; A61K 35/17; A61K 35/30; A61K 35/545; A61K 31/135; A61K 31/137; A61K 31/343; A61K 31/55; A61P 35/00; C12N 5/0619; C12N 2503/00; C12N 2506/11; C12N 2506/45
See application file for complete search history.

(56) References Cited

U.S. PATENT DOCUMENTS

| | | | |
|---|---|---|---|
| 8,257,941 | B2 | 9/2012 | Sakurada et al. |
| 9,459,266 | B2 | 10/2016 | Bahn et al. |
| 9,464,273 | B2 | 10/2016 | Reijo Pera et al. |
| 10,233,422 | B2 | 3/2019 | Reijo Pera et al. |
| 2007/0003931 | A1 | 1/2007 | Mrazek et al. |
| 2009/0053232 | A1 | 2/2009 | Eroglu et al. |
| 2009/0324559 | A1 | 12/2009 | Sakurada et al. |
| 2016/0058766 | A1 | 3/2016 | Fava et al. |
| 2016/0209400 | A1 | 7/2016 | Bohlen et al. |
| 2016/0230217 | A1 | 8/2016 | Apte et al. |
| 2019/0328782 | A1 | 10/2019 | Braithwaite et al. |

FOREIGN PATENT DOCUMENTS

| | | | |
|---|---|---|---|
| WO | 2012058201 | A2 | 5/2012 |
| WO | 2016069591 | A2 | 5/2016 |

OTHER PUBLICATIONS

Simonetti M, Paldy E, Njoo C, Bali KK, Worzfeld T, Pitzer C, Kuner T, Offermanns S, Mauceri D, Kuner R. The impact of Semaphorin 4C/Plexin-B2 signaling on fear memory via remodeling of neuronal and synaptic morphology. Mol Psychiatry. Apr. 2021;26(4):1376-1398. doi: 10.1038/s41380-019-0491-4. Epub Aug. 23, 2019. PMID: 31444474; PMCID: PMC7985029.
Stern S, Santos R, Marchetto MC, Mendes APD, Rouleau GA, Biesmans S, Wang QW, Yao J, Charnay P, Bang AG, Alda M, Gage FH. Neurons derived from patients with bipolar disorder divide into intrinsically different sub-populations of neurons, predicting the patients' responsiveness to lithium. Mol Psychiatry. Jun. 2018;23(6):1453-1465. doi: 10.1038/mp.2016.260. Epub Feb. 28, 2017. PMID: 28242870; PMCID: PMC5573640.
Vadodaria KC, Stern S, Marchetto MC, Gage FH. Serotonin in psychiatry: in vitro disease modeling using patient-derived neurons. Cell Tissue Res. Jan. 2018;371(1):161-170. doi: 10.1007/s00441-017-2670-4. Epub Aug. 15, 2017. PMID: 28812143.
Woo HI, Lim SW, Myung W, Kim DK, Lee SY. Differentially expressed genes related to major depressive disorder and antidepressant response: genome-wide gene expression analysis. Exp Mol Med. Aug. 3, 2018;50(8):1-11. doi: 10.1038/s12276-018-0123-0. PMID: 30076325; PMCID: PMC6076250.
Yi E-S, Oh S, Lee JK, Leem YH. Chronic stress-induced dendritic reorganization and abundance of synaptosomal PKA-dependent CP-AMPA receptor in the basolateral amygdala in a mouse model of depression. Biochem Biophys Res Commun. May 6, 2017;486(3):671-678. doi: 10.1016/j.bbrc.2017.03.093. Epub Mar. 20, 2017. PMID: 28336441.
Elizalde N, Pastor PM, Garcia-García AL, Serres F, Venzala E, Huarte J, Ramírez MJ, Del Rio J, Sharp T, Tordera RM. Regulation of markers of synaptic function in mouse models of depression: chronic mild stress and decreased expression of VGLUT1. J Neurochem. Sep. 1, 2010;114(5):1302-14. doi: 10.1111/j. 1471-4159.2010.06854. x. Epub Jun. 10, 2010. PMID: 20550627.

(Continued)

*Primary Examiner* — Olga N Chernyshev
(74) *Attorney, Agent, or Firm* — The Roy Gross Law Firm, LLC; Roy D. Gross

(57) ABSTRACT

Methods of determining the suitability of a subject for treatment with a therapeutic agent are provided. Methods of providing a personalized treatment protocol based on suitability of a subject to be treated with a therapeutic agent are also provided, as are methods of treating those subjects who are suitable.

20 Claims, 7 Drawing Sheets

(56) References Cited

OTHER PUBLICATIONS

Duncan WC, Sarasso S, Ferrarelli F, Selter J, Riedner BA, Hejazi NS, Yuan P, Brutsche N, Manji HK, Tononi G, Zarate CA. Concomitant BDNF and sleep slow wave changes indicate ketamine-induced plasticity in major depressive disorder. Int J Neuropsychopharmacol. Mar. 2013;16(2):301-11. doi: 10.1017/S1461145712000545. Epub Jun. 7, 2012. PMID: 22676966; PMCID: PMC3510337.
Underwood MD, Kassir SA, Bakalian MJ, Galfalvy H, Mann JJ, Arango V. Neuron density and serotonin receptor binding in prefrontal cortex in suicide. Int J Neuropsychopharmacol. May 2012;15(4):435-47. doi: 10.1017/S1461145711000691. Epub May 9, 2011. PMID: 21733245; PMCID: PMC4167642.
Kang HJ, Voleti B, Hajszan T, Rajkowska G, Stockmeier CA, Licznerski P, Lepack A, Majik MS, Jeong LS, Banasr M, Son H, Duman RS. Decreased expression of synapse-related genes and loss of synapses in major depressive disorder. Nat Med. Sep. 2012;18(9):1413-7. doi: 10.1038/nm.2886. PMID: 22885997; PMCID: PMC3491115.
Licznerski P, Duman RS. Remodeling of axo-spinous synapses in the pathophysiology and treatment of depression. Neuroscience. Oct. 22, 2013;251:33-50. doi: 10.1016/j.neuroscience.2012.09.057. Epub Oct. 2, 2012. PMID: 23036622; PMCID: PMC3566360.
Duman CH, Duman RS. Spine synapse remodeling in the pathophysiology and treatment of depression. Neurosci Lett. Aug. 5, 2015;601:20-9. doi: 10.1016/j.neulet.2015.01.022. Epub Jan. 9, 2015. PMID: 25582786; PMCID: PMC4497940.
McAvoy K, Russo C, Kim S, Rankin G, Sahay A. Fluoxetine induces input-specific hippocampal dendritic spine remodeling along the septotemporal axis in adulthood and middle age. Hippocampus. Nov. 2015;25(11):1429-46. doi: 10.1002/hipo.22464. Epub May 2, 2015. PMID: 25850664; PMCID: PMC4596739.
Ho SM, Hartley BJ, Tcw J, Beaumont M, Stafford K, Slesinger PA, Brennand KJ. Rapid Ngn2-induction of excitatory neurons from hiPSC-derived neural progenitor cells. Methods. May 15, 2016;101:113-24. doi: 10.1016/j.ymeth.2015.11.019. Epub Nov. 25, 2015. PMID: 26626326; PMCID: PMC4860098.
Tanabe K, Ang CE, Chanda S, Olmos VH, Haag D, Levinson DF, Sudhof TC, Wernig M. Transdifferentiation of human adult peripheral blood T cells into neurons. Proc Natl Acad Sci U S A. Jun. 19, 2018;115(25):6470-6475. doi: 10.1073/ponas.1720273115. Epub Jun. 4, 2018. PMID: 29866841; PMCID: PMC6016798.
Vadodaria KC, Ji Y, Skime M, Paquola A, Nelson T, Hall-Flavin D, Fredlender C, Heard KJ, Deng Y, Le AT, Dave S, Fung L, Li X, Marchetto MC, Weinshilboum R, Gage FH. Serotonin-induced hyperactivity in SSRI-resistant major depressive disorder patient-derived neurons. Mol Psychiatry. Jun. 2019;24(6):795-807. doi: 10.1038/s41380-019-0363-y. Epub Jan. 30, 2019. PMID: 30700803.
Vadodaria KC, Ji Y, Skime M, Paquola AC, Nelson T, Hall-Flavin D, Heard KJ, Fredlender C, Deng Y, Elkins J, Dani K, Le AT, Marchetto MC, Weinshilboum R, Gage FH. Altered serotonergic circuitry in SSRI-resistant major depressive disorder patient-derived neurons. Mol Psychiatry. Jun. 2019;24(6):808-818. doi: 10.1038/s41380-019-0377-5. Epub Mar. 22, 2019. PMID: 30903001; PMCID: PMC7409972.
Brennand KJ, Simone A, Jou J, Gelboin-Burkhart C, Tran N, Sangar S, Li Y, Mu Y, Chen G, Yu D, McCarthy S, Sebat J, Gage FH. Modelling schizophrenia using human induced pluripotent stem cells. Nature. May 12, 2011;473(7346):221-5. doi: 10.1038/nature09915. Epub Apr. 13, 2011. Erratum in: Nature. Nov. 24, 2011;479(7374):556. PMID: 21490598; PMCID: PMC3392969.
Robicsek O, Karry R, Petit I, Salman-Kesner N, Muller FJ, Klein E, Aberdam D, Ben-Shachar D. Abnormal neuronal differentiation and mitochondrial dysfunction in hair follicle-derived induced pluripotent stem cells of schizophrenia patients. Mol Psychiatry. Oct. 2013;18(10):1067-76. doi: 10.1038/mp.2013.67. Epub Jun. 4, 2013. PMID: 23732879.
Madison JM, et al. Characterization of bipolar disorder patient-specific induced pluripotent stem cells from a family reveals neurodevelopmental and mRNA expression abnormalities. Mol Psychiatry. Jun. 2015;20(6):703-17. doi: 10.1038/mp.2015.7. Epub Mar. 3, 2015. PMID: 25733313; PMCID: PMC4440839.
Drysdale AT, et al. Resting-state connectivity biomarkers define neurophysiological subtypes of depression. Nat Med. Jan. 2017;23(1):28-38. doi: 10.1038/nm.4246. Epub Dec. 5, 2016. Erratum in: Nat Med. Feb. 7, 2017;23 (2):264. PMID: 27918562; PMCID: PMC5624035.
Vadodaria KC, Amatya DN, Marchetto MC, Gage FH. Modeling psychiatric disorders using patient stem cell-derived neurons: a way forward. Genome Med. Jan. 4, 2018;10(1):1. doi: 10.1186/s13073-017-0512-3. PMID: 29301565; PMCID: PMC5755287.
Marchetto MC, et al. Altered proliferation and networks in neural cells derived from idiopathic autistic individuals. Mol Psychiatry. Jun. 2017;22(6):820-835. doi: 10.1038/mp.2016.95. Epub Jul. 5, 2016. PMID: 27378147; PMCID: PMC5215991.
Santos R, et al. Differentiation of Inflammation-Responsive Astrocytes from Glial Progenitors Generated from Human Induced Pluripotent Stem Cells. Stem Cell Reports. Jun. 6, 2017;8(6):1757-1769. doi: 10.1016/j.stemcr.2017.05.011. PMID: 28591655; PMCID: PMC5470172.
Yoon KJ, et al. Modeling a genetic risk for schizophrenia in iPSCs and mice reveals neural stem cell deficits associated with adherens junctions and polarity. Cell Stem Cell. Jul. 3, 2014;15(1):79-91. doi: 10.1016/j.stem.2014.05.003. Erratum In: Cell Stem Cell. Mar. 5, 2015;16(3):339. PMID: 24996170; PMCID: PMC4237009.
Vadodaria KC, Marchetto MC, Mertens J, Gage FH. Generating human serotonergic neurons in vitro: Methodological advances. Bioessays. Nov. 2016;38(11):1123-1129. doi: 10.1002/bies.201600127. Epub Sep. 22, 2016. PMID: 27716980.
Lu J, Zhong X, Liu H, Hao L, Huang CT, Sherafat MA, Jones J, Ayala M, Li L, Zhang SC. Generation of serotonin neurons from human pluripotent stem cells. Nat Biotechnol. Jan. 2016;34(1):89-94. doi: 10.1038/nbt.3435. Epub Dec. 14, 2015. PMID: 26655496; PMCID: PMC4711820.
Lee JH, Mitchell RR, McNicol JD, Shapovalova Z, Laronde S, Tanasijevic B, Milsom C, Casado F, Fiebig-Comyn A, Collins TJ, Singh KK, Bhatia M. Single Transcription Factor Conversion of Human Blood Fate to NPCs with CNS and PNS Developmental Capacity. Cell Rep. Jun. 9, 2015;11(9):1367-76. doi: 10.1016/j.celrep.2015.04.056. Epub May 21, 2015. PMID: 26004181.
Sheng C, Jungverdorben J, Wiethoff H, Lin Q, Flitsch LJ, Eckert D, Hebisch M, Fischer J, Kesavan J, Weykopf B, Schneider L, Holtkamp D, Beck H, Till A, Wullner U, Ziller MJ, Wagner W, Peitz M, Brustle O. A stably self-renewing adult blood-derived induced neural stem cell exhibiting patternability and epigenetic rejuvenation. Nat Commun. Oct. 2, 2018;9(1):4047. doi: 10.1038/s41467-018-06398-5. PMID: 30279449; PMCID: PMC6168501.
Rosoklija G, Toomayan G, Ellis SP, Keilp J, Mann JJ, Latov N, Hays AP, Dwork AJ. Structural abnormalities of subicular dendrites in subjects with schizophrenia and mood disorders: preliminary findings. Arch Gen Psychiatry. Apr. 2000;57(4):349-56. doi: 10.1001/archpsyc.57.4.349. PMID: 10768696.
Soetanto A, Wilson RS, Talbot K, Un A, Schneider JA, Sobiesk M, Kelly J, Leurgans S, Bennett DA, Arnold SE. Association of anxiety and depression with microtubule-associated protein 2- and synaptopodin-immunolabeled dendrite and spine densities in hippocampal CA3 of older humans. Arch Gen Psychiatry. May 2010;67(5):448-57. doi: 10.1001/archgenpsychiatry.2010.48. PMID: 20439826; PMCID: PMC2926797.
Donohue HS, Gabbott PL, Davies HA, Rodriguez JJ, Cordero MI, Sandi C, Medvedev NI, Popov VI, Colyer FM, Peddie CJ, Stewart MG. Chronic restraint stress induces changes in synapse morphology in stratum lacunosum-moleculare CA1 rat hippocampus: a stereological and three-dimensional ultrastructural study. Neuroscience. Jun. 30, 2006;140(2):597-606. doi: 10.1016/j.neuroscience.2006.02.072. PMID: 16600515.
Chen J, Buchanan JB, Sparkman NL, Godbout JP, Freund GG, Johnson RW. Neuroinflammation and disruption in working memory in aged mice after acute stimulation of the peripheral innate immune

(56) References Cited

OTHER PUBLICATIONS system. Brain Behav Immun. Mar. 2008,22(3):301-11. doi: 10.1016/j.bbi.2007.08.014. Epub Oct. 24, 2007. PMID: 17951027; PMCID: PMC2374919.

Sunanda, Rao MS, Raju TR. Effect of chronic restraint stress on dendritic spines and excrescences of hippocampal CA3 pyramidal neurons—a quantitative study. Brain Res. Oct. 2, 1995;694(1-2):312-7. doi: 10.1016/0006-8993(95)00822-8. PMID: 8974660.

Sheline YI, Gado MH, Kraemer HC. Untreated depression and hippocampal volume loss. Am J Psychiatry. Aug. 2003;160(8):1516-8. doi: 10.1176/appi.ajp.160.8.1516. PMID: 12900317.

Vermetten E, Vythilingam M, Southwick SM, Charney DS, Bremner JD. Long-term treatment with paroxetine increases verbal declarative memory and hippocampal volume in posttraumatic stress disorder. Biol Psychiatry. Oct. 1, 2003;54(7):693-702. doi: 10.1016/s0006-3223(03)00634-6. PMID: 14512209; PMCID: PMC3233762.

Hajszan T, MacLusky NJ, Leranth C. Short-term treatment with the antidepressant fluoxetine triggers pyramidal dendritic spine synapse formation in rat hippocampus. Eur J Neurosci. Mar. 2005;21(5):1299-303. doi: 10.1111/i.1460-9568.2005.03968.x. PMID: 15813939.

Norrholm SD, Ouimet CC. Chronic fluoxetine administration to juvenile rats prevents age-associated dendritic spine proliferation in hippocampus. Brain Res. Nov. 17, 2000;883(2):205-15. doi: 10.1016/s0006-8993(00)02909-7. PMID: 11074049.

Wang JW, David DJ, Monckton JE, Battaglia F, Hen R. Chronic fluoxetine stimulates maturation and synaptic plasticity of adult-born hippocampal granule cells. J Neurosci. Feb. 6, 2008;28(6):1374-84. doi: 10.1523/JNEUROSCI.3632-07.2008. PMID: 18256257; PMCID: PMC6671574.

Chen JL, Flanders GH, Lee WC, Lin WC, Nedivi E. Inhibitory dendrite dynamics as a general feature of the adult cortical microcircuit. J Neurosci. Aug. 31, 2011;31(35):12437-43. doi: 10.1523/JNEUROSCI.0420-11.2011. PMID: 21880904; PMCID: PMC3180878.

Bessa JM, Ferreira D, Melo I, Marques F, Cerqueira JJ, Palha JA, Almeida OF, Sousa N. The mood-improving actions of antidepressants do not depend on neurogenesis but are associated with neuronal remodeling. Mol Psychiatry. Aug. 2009;14(8):764-73, 739. doi: 10.1038/mp.2008.119. Epub Nov. 4, 2008. PMID: 18982002.

Gourley SL, Swanson AM, Koleske AJ. Corticosteroid-induced neural remodeling predicts behavioral vulnerability and resilience. J Neurosci. Feb. 13, 2013;33(7):3107-12. doi: 10.1523/JNEUROSCI.2138-12.2013. PMID: 23407965; PMCID: PMC3711631.

PCT International Search Report for International Application No. PCT/IL2021/050183, mailed May 27, 2021, 7pp.

PCT Written Opinion for International Application No. PCT/IL2021/050183, mailed May 27, 2021, 7pp.

PCT International Preliminary Report on Patentability for International Application No. PCT/IL2021/050183, issued on Aug. 11, 2022, 8pp.

Harrill, J.A. et al., "Use of high content image analysis to detect chemical-induced changes in synaptogenesis in vitro", Toxicology in Vitro, Elsevier Science, GB, vol. 25, No. 1, pp. 368-387 Feb. 1, 2011. doi: 10.1016/j.tiv.2010.10.011. Epub Oct. 20, 2010. PMID: 20969947.

Melissa J. Alldred et al., "Microarray analysis of CA1 pyramidal neurons in a mouse model of tauopathy reveals progressive synaptic dysfunction", Neurobiology of Disease, Elsevier, Amsterdam, NL, vol. 45, No. 2, pp. 751-762, Oct. 28, 2011. doi: 10.1016/j.nbd.2011.10.022. Epub Nov. 7, 2011. PMID: 22079237; PMCID: PMC3259262.

METHODS OF THERAPEUTIC PROGNOSTICATION

CROSS REFERENCE TO RELATED APPLICATIONS

This application is a National Phase of PCT Patent Application No. PCT/IL2021/050183 having International filing date of Feb. 16, 2021, which claims the benefit of priority of U.S. Provisional Patent Application No. 62/977,308, filed Feb. 16, 2020, the contents of which are all incorporated herein by reference in their entirety.

FIELD OF INVENTION

The present invention is in the field of drug suitability prognosis.

BACKGROUND OF THE INVENTION 300 million people suffer from Major Depression. Current therapies are highly non-specific and/or often non-efficacious. Approximately 63% of patients will not respond to their first line treatment. Following this, a typical patient goes through multiple rounds of drug trialing, each lasting weeks-to-months searching for the right medication for them. There are over 70 different marketed pharmaceutical drugs to treat depression. A better solution is required to avoid this trial-and-error process and get patients faster to the right drug choice for them.

Personalized medicine allows tailoring of treatment to the individual. Many tools for personalized medicine focus on genetic polymorphisms which can partially predict responsiveness to treatment. Genes alone, however, are only part of the picture. The regulation of gene expression through epigenetics, the regulation of mRNA expression through cellular cues, the changing balance of protein expression and structural changes, all of these processes are uniquely individual. A method that takes into account as many features of the individual's background as possible can bring increased accuracy to personalized medicine predictions.

SUMMARY OF THE INVENTION

The present invention provides methods of determining suitability of a subject to receive treatment with a therapeutic agent. Methods of providing a personalized treatment protocol based on suitability of a subject to be treated with a therapeutic agent are also provided, as are methods of treating those subjects who are suitable.

According to a first aspect, there is provided a method of determining suitability of a subject to be treated with a therapeutic agent, comprising:

a) providing a neuronal cell derived from a non-neuronal cell from the subject; and b) assessing the neuronal cell for at least one biomarker, wherein the biomarker is selected from a group consisting of post-synaptic puncta perimeter length, pre-synaptic puncta number, pre- and post-synaptic colocalized puncta number, pre-synaptic puncta perimeter, dendritic length, dendritic spine length, and expression of at least one gene provided in Tables 1 and 2; wherein pre-synaptic puncta number, pre- and post-synaptic colocalized puncta number, expression of at least one gene provided in Table 1 above a predetermined threshold; or post-synaptic puncta perimeter length, pre-synaptic puncta perimeter length, dendritic length, dendritic spine length, expression of at least one gene provided in Table 2 below a predetermined threshold indicates suitability of the subject to be treated with the therapeutic agent;

thereby determining suitability of a subject to be treated with a therapeutic.

According to another aspect, there is provided a method of determining suitability of a subject to be treated with a therapeutic agent, comprising:

a) providing a neuronal cell derived from a non-neuronal cell from the subject;

b) administering the therapeutic agent to the neuronal cell; and c) assessing the neuronal cell for at least one biomarker, wherein the biomarker is selected from a group consisting of, post-synaptic puncta number, density of post-synaptic puncta, pre- and post-synaptic colocalized puncta number, dendritic spine length, dendrite length and expression of at least one gene provided in Tables 3 and 4, wherein dendrite length, expression of at least one gene provided in Table 4 below a predetermined threshold or post-synaptic puncta number, pre- and post-synaptic colocalized puncta number, density of post-synaptic puncta, dendritic spine length, expression of at least one gene provided in Table 3 above a predetermined threshold indicates suitability of the subject to be treated with the therapeutic agent;

thereby determining suitability of a subject to be treated with a therapeutic.

According to another aspect, there is provided a method of determining suitability of a subject to be treated with a therapeutic agent, comprising:

a) providing a neuronal cell derived from a non-neuronal cell from the subject;

b) assessing the neuronal cell for at least one biomarker, wherein the biomarker is selected from a group consisting of pre-synaptic puncta perimeter length, pre- and post-synaptic colocalized puncta number, dendritic spine length, dendrite length, density of post-synaptic puncta and expression of at least one gene provided in either Table 5 or Table 6;

c) administering the therapeutic agent to the neuronal cell; and assessing the therapeutic agent's effect on the at least one biomarker, wherein a. downregulation of dendrite length, downregulation of expression of at least one gene provided in Table 6, upregulation of dendritic spine length, upregulation of pre- and post-synaptic colocalized puncta number, upregulation of density of post-synaptic puncta or upregulation of expression of at least one gene provided in Table 5, indicates suitability of the subject to be treated with the therapeutic agent; and b. downregulation of pre-synaptic puncta perimeter length, or dendritic spine length indicates unsuitability of the subject to be treated with the therapeutic agent;

thereby determining suitability of a subject to be treated with a therapeutic.

According to some embodiments, the biomarker is selected from a group consisting of post-synaptic puncta perimeter length, pre-synaptic puncta number, pre- and post-synaptic colocalized puncta number, pre-synaptic puncta perimeter length, and expression of at least one significant gene provided in either Tables 1 or 2.

According to some embodiments, the at least one significant gene provided in Table 1 is selected from: NPY2R, MMS22L, CASP8AP2, BRIP1, SIM1, DHFR, RBL1, MGAM, WNT8B, APAF1, MAP2K6, BLM, LBR, CALCR, ZWILCH, LONRF3, CIP2A, SMC2, C4orf46, DLX2, EIF1AX, LRRC40, LRRC8B, MCM10, TIGAR, ALG10, VGLL3, ZNF730, SLC25A24, RTKN2, BUB3, DNA2, TFAM, PCLAF, TAF7L, OSBPL11, GNB4, UTP20, MCM8, ATAD5, EXO1, CENPE, NUCKS1, FBXO5, SYCP2L, NUP50, RASA2, KNL1, SRSF1, SLC25A13, RIT2, FEZF1, KIF11, PRKDC, CHEK1, DLX1, CENPI, KIF18A, NUP155, CHML, HAUS6, TRA2B, PHF6, QSER1, ZNF678, FAM135A, PDYN, EXOC6, VMA21, CKAP2, CENPQ, DEPDC1B, XKR9, HOOK3, SNRNP48, TMPO, LCLAT1, VPS13A, RRM2, DTL, PAQR3, TAF9B, CTDSPL2, ZNF260, ZPLD1, APIS, DCLRE1A, ANGEL2, MPHOSPH6, PIGW, AGPS, FANCB, SIKE1, GPC3, LRRN3, SFRP4, ZNF347, CYP26A1, TRNT1, PCDH19, WASF3, ATAD2, C5orf34, STK38L, ME2, MELK, PDS5A, CENPF, CDC7, COMMD2, PCNA, MTBP, ZMYM4, SPIN4, TAF1A, MRPL19, BCLAF3, NUP107, RNGTT, CBX5, RBBP8, CNOT6, CDH6, TOP2A, SMC4, EX005, MCM4, PTPN13, MAPK1IP1L, SUV39H2, DMRTA1, DSCC1, ERCC8, NDC1, ASPM, RADX, LRRC3B, SELENOI, NEIL3, FANCI, USP14, TYW3, C18orf54, FKBP5, XRN2, MGA, FANCM, HELLS, ITGA6, NCAPG, CNTNAP2, ZNF66, XRCC2, ANLN, C9orf40, NUDT21, HNRNPA3, ADAL, RBM12, H2AFV, CREB1, FXN, ARHGAP11A, CDCA2, NBN, TARDBP, SMARCAD1, BDP1, and SRBD1.

According to some embodiments, the at least one significant gene provided in Table 1 is selected from: FEZF1, RIT2, XKR9, and DLX1.

According to some embodiments, the at least one significant gene provided in Table 2 is selected from: LIN37, CYP27A1, GSTT2B, DRGX, SKOR2, COLEC11, TRIM47, KIAA1211L, COL8A2, PHOX2B, HSD3B7, SLPI, ADAMTSL2, GAA, CTSD, FTH1, HS6ST1, ALDOA, TAF1C, COL11A2, NPR2, OGFR, CEMIP, TNFRSF14, CXCL8, ELN, PENK, IRF2BPL, PSD4, USH1C, SLC45A2, RPS26, JOSD2, NCMAP, GATD3B, PLEKHD1, IL17RC, PTGER4, TOM1, GLIS2, ZNF835, EN2, PNPLA7, ADAMTS15, COL6A1, TSHZ3, TULP1, KCNF1, PI4 KB, NTNG1, PCSK9, TYRP1, PRSS33, JUNB, HOXB5, BDKRB2, F12, FRMPD1, TLX3, PADI2, RARA, TBC1D10B, STARD3, NAGA, SLC2A1, PIEZO2, APOL2, PGPEP1, COL9A2, KCNA1, ACAN, TRAF1, NNMT, ZBTB4, WBP2, FAM3A, EPHB3, LOX, PGM1, MAL, ZSWIM8, PSMB10, PPP6R1, TRIM8, AIFM2, PIGS, FAM163B, SLC38A3, CCER2, PLPP4, RABEP2, LOXL1, THBS2, DUSP1, CCDC187, P2RX2, NDRG1, ITPRIP, ACOT1, RARRES2, SST, TMEM72, LIMS2, PVALB, CHST8, NDUFA4L2, YIPF3, YPEL3, ISL2, FZD9, RPRM, CXCL6, GRAMD1A, PPM1M, PDZRN3, NTNG2, SSH3, ABCD1, PRCD, WFIKKN2, C1R, FGF10, NKX3-2, FSTL3, C9orf24, HOXB6, FBLN1, COL5A3, C1S, NCOR2, TMEM175, C20orf85, and AVIL.

According to some embodiments, the at least one significant gene provided in Table 2 is selected from: ELN and EYA2.

According to some embodiments, the biomarker is selected from a group consisting of density of post-synaptic puncta, pre- and post-synaptic colocalized puncta number, dendritic spine length, and expression of at least one significant gene provided in either Tables 3 or 4.

According to some embodiments, the at least one significant gene provided in Table 3 is selected from: SLC25A13, SPIN4, SLC25A17, SIM1, NPY2R, ZC3H13, WNT8B, F8, TIGAR, DMRTA1, ZWILCH, WNT10B, GPC3, ZBTB24, NOS2, EIF1AX, HLA-DMA, CHML, DHFR, OSBPL11, MCUR1, CDH6, TFAM, SNRNP48, MEIOC, BAG4, STK38L, HESX1, LRRC8B, MGA, FREM2, SFRP4, TSGA10IP, MDN1, MCM4, CCDC150, HAUS6, TNFRSF13C, PPAT, SLC7A11, ARHGEF26, S100A13, FBXO22, SIKE1, ANKRD27, NFKBID, RNGTT, POU5F1B, PRKDC, MGME1, TXNRD1, SMG1, DLX2, WWP1, SYCP2L, ZNF347, PTPN13, PCGF5, USP37, LGI1, SIGLEC10, PHF6, ITGA6, SELENOI, ATAD5, ADAL, MZT1, DNA2, and PAWR.

According to some embodiments, the at least one significant gene provided in Table 3 is selected from DLX2 and SIM1.

According to some embodiments, the at least one significant gene provided in Table 4 is selected from: MAFB, DRGX, ADAMTSL2, FRMPD1, POU4F1, COL8A2, INMT, CDKN1C, NNMT, SKOR2, NPR2, CXCL8, PSMB9, CEMIP, KLHL35, PSMB8, PIRT, TMEM176B, VLDLR, INHBB, ACOT1, COL15A1, TNFRSF14, TBC1D2, PENK, TRAF1, APOL2, TRPV2, ASPN, FAM20C, BDKRB2, TLX3, TMEM176A, CPNE5, GALNT14, THBS2, PLEKHD1, TSHZ3, ELN, PLCH2, NTNG2, KCNA1, TAF1C, LGALS3BP, IRF2BPL, COLEC11, ADAMTS15, ITPRIP, ADAMTSL1, CABP7, CACNA1H, CPNE9, GFRA2, ABCC6, FNDC5, SLC2A1, CCER2, CPA4, PIEZO2, PLD5, HS6ST1, TMEM163, PSD4, EYA2, PADI2, EGFLAM, C1S, PALM, FGF1, PRSS33, C1R, TLR6, PHOX2B, TLX1, OPTN, TAP1, PTGER2, P4HA3, PLAC9, NFIX, TREM1, KCNJ5, COL6A1, ADAMTS8, GLIS2, HES6, ALDOC, FMOD, FBLN5, USP18, CHST8, LRFN5, LOX, NKX3-2, USH1C, ZNF575, OPRK1, SECTM1, SAMD9L, HCN1, CXCL6, OPRM1, TAP2, ARHGEF28, GPBAR1, IAH1, KHDC1, PARP10, OLFML2B, PODN, ARL17B, SYNC, PRPH, TRMT9B, KDM4B, NDUFA4L2, CCDC183, RBP1, PTGDS, JOSD2, AQP6, CXCL2, KIF26A, C5orf63, CCDC187, EFEMP2, SUN2, SAMD9, POLR2J3, RAB42, RBMS3, SST, OGFR, PRCD, RPH3A, COL1A1, IGFBP5, HOXB5, TMC3, TF, MX2, SH3TC2, LOXL1, OTOG, MAB21L2, SLC38A3, CD151, MGP, RSAD2, PXDNL, DYRK1B, MCC, MKX, SUSD1, ADAMTS4, IL17RC, ZFPM1, EPHB3, SLC17A7, ISLR, LURAP1L, GAA, HMX1, DHRS3, ARHGAP23, S100B, HS3ST2, TRIM8, VSTM2B, SMPD1, SLC4A4, LYPD1, TMEM175, and PLPP4.

According to some embodiments, the at least one significant gene provided in Table 4 is selected from ELN.

According to some embodiments, the biomarker is selected from a group consisting of pre-synaptic puncta perimeter length, pre- and post-synaptic colocalized puncta number, density of post-synaptic puncta, dendritic spine length, dendrite length and expression of at least one significant gene provided in either Table 5 or Table 6.

According to some embodiments, the biomarker is selected from a group consisting of expression of at least one significant gene provided in either Table 5 or Table 6.

According to some embodiments, the at least one significant gene provided in Table 5 is selected from: CXCL11, PTPRQ, COX16, RSAD2, LLPH, TSTD2, HS3ST5, CHMP4A, PSD3, ARL17B, FGF1, INMT, LHFPL3, SCN9A, MINDY3, ZFP69B, and ZNF221.

According to some embodiments, the at least one significant gene provided in Table 6 is selected from: LIN37, NFKBID, TCF7, DUSP23, TENT5B, UGT3A2, CCDC51, CTNS, PYCARD, ABHD4, TEKT3, SMPDL3B, KLC3, PNKP, SPNS1, FAM117A, PPL, ZNF425, MT2A, PPP1R1B, CKS1B, LGR6, ART5, ADRA2B, ZNF394, ETV5, VWA2, CDC42BPG, TRAF3IP2, TXNRD2, RAB43, APOE, TYW1B, TOM1, GPR89A, HAUS8, TNNI3, TJP3, RNASEK, MACROD1, DDX55, MAP4K1, MADCAM1, NMRK2, RARRES2, GABRD, CTSD, FBXO2, MT1X, LRRC2, SLC45A2, KLHL21, RILPL1, PSMB10, LHPP, RABEP2, and LARGE2.

According to some embodiments, the upregulation of dendritic spine length is upregulation of dendritic spine length in a spine type selected from mushroom spines and thin spines.

According to some embodiments, the therapeutic agent comprises a psychiatric drug.

According to some embodiments, the therapeutic agent is selected from Bupropion, Mirtazapine, Nortriptyline and Citalopram.

According to some embodiments, the therapeutic agent is Bupropion.

According to some embodiments, the method of the invention further comprises providing a personalized treatment protocol for the subject based on the suitability of the subject to be treated with the therapeutic agent.

According to some embodiments, the method of the invention further comprises administering the therapeutic agent to the subject based on the suitability of the subject to be treated with the therapeutic agent.

According to some embodiments, the neuron is a cortical neuron.

According to some embodiments, the cortical neuron is a frontal cortical neuron.

According to some embodiments, the neuronal cell is derived from an induced pluripotent stem cell (iPSC) derived from a non-neuronal cell from the subject.

According to some embodiments, the non-neuronal cell is a blood cell.

According to some embodiments, the blood cell is a peripheral blood mononuclear cell (PBMC).

According to some embodiments, the PBMC is a lymphoblast.

According to some embodiments, the subject comprises a human or other mammal.

According to some embodiments, the assessing comprises measuring expression of the biomarker in the neuronal cell.

According to some embodiments, the expression is RNA expression, protein expression or both.

According to some embodiments, the expression is RNA expression, and the assessing comprises RNA sequencing, RNA microarray analysis, PCR or microscopy analysis.

According to some embodiments, data obtained from the neuronal cell is used alone or combined with the subject's clinical, genetic or biological background to determine suitability of the subject to be treated by the therapeutic.

According to some embodiments, data obtained from the neuronal cell is used alone or combined with the subject's clinical, genetic or biological background to provide the personalized treatment protocol.

According to some embodiments, the subject suffers from a psychiatric disorder treatable by Bupropion.

According to some embodiments, the psychiatric disorder comprises major depression, unipolar depression or both.

According to some embodiments, the psychiatric disorder comprises major depression.

According to some embodiments, the pre-synaptic puncta are defined by expression of synapsin.

According to some embodiments, the post-synaptic puncta are defined by expression of PSD95.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
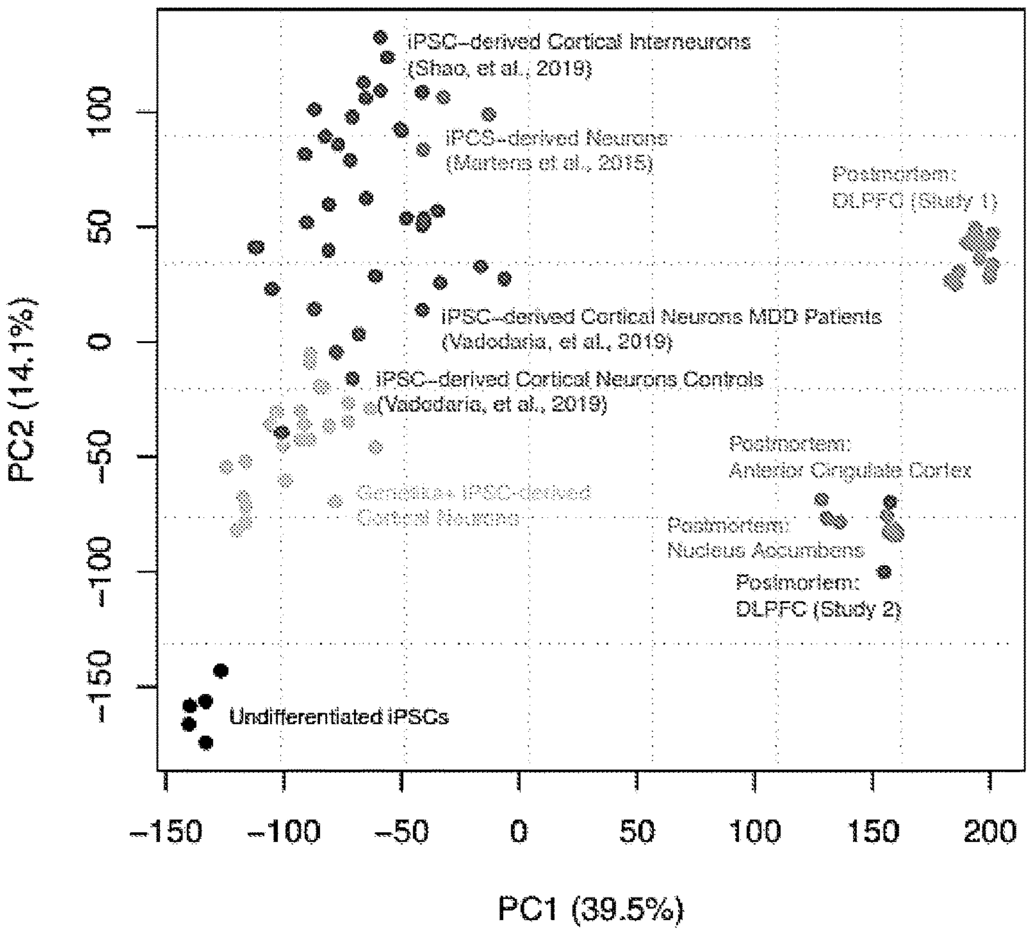
FIG. 1. Gene expression principal component analysis (PCA) of differentiated cells, brain tissues and undifferentiated pluripotent stem cells. Induced pluripotent stem cell (iPSC)—derived cortical neurons compared with other differentiated neurons from iPSCs (iPSC-derived cortical interneurons, iPSC-derived neurons, iPSC-derived cortical neurons from major depressive disorder (MDD) patients and control iPSC-derived cortical neurons), postmortem brain tissues (Dorsolateral prefrontal cortex (DLPFC), Anterior Cingulate Cortex and Nucleus Accumbens) and undifferentiated-iPSCs.

The present invention, in some embodiments, provides methods of determining the suitability of a subject for treatment with a therapeutic agent. Methods of providing a personalized treatment protocol based on suitability of a subject to be treated with a therapeutic agent are also provided, as are methods of treating those subjects who are suitable.

The present invention is based on the surprising finding that there are significant differences in neuronal morphology and gene expression between induced neurons derived from non-neuronal cells from patients suffering from major depression who respond to standard treatments and those who do not. Reproducible differences were detectable both at baseline and after treatment and can be used as biomarkers to determine suitability of a subject to be treated with a psychiatric drug. Surprisingly, many of the markers were common between several of the drugs tested.

By a first aspect, there is provided a method of determining suitability of a subject to be treated with a therapeutic agent, the method comprising:

a) providing a neuronal cell derived from a non-neuronal cell from the subject; and b) assessing the neuronal cell for at least one biomarker; wherein expression of the biomarker above or below a predetermined threshold indicates suitability of the subject to be treated with the therapeutic agent;

thereby determining suitability of the subject to be treated with the therapeutic.

By another aspect, there is provided a method of determining suitability of a subject to be treated with a therapeutic agent, comprising:

a) providing a neuronal cell derived from a non-neuronal cell from the subject;

b) administering the therapeutic agent to the neuronal cell; and c) assessing the neuronal cell for at least one biomarker, wherein expression of the biomarker above or below a predetermined threshold indicates suitability of the subject to be treated with the therapeutic agent;

thereby determining suitability of the subject to be treated with the therapeutic.

By another aspect, there is provided a method of determining suitability of a subject to be treated with a therapeutic agent, comprising:

a) providing a neuronal cell derived from a non-neuronal cell from the subject;

b) assessing the neuronal cell for at least one biomarker;

c) administering the therapeutic agent to the neuronal cell; and d) assessing the therapeutic agent's effect on the biomarker, wherein downregulation or upregulation of the biomarker indicates suitability of the subject to be treated with the therapeutic agent;

thereby determining suitability of a subject to be treated with a therapeutic.

In some embodiments, the subject is a mammal. In some embodiments, the subject is a human. In some embodiments, the subject suffers from a psychiatric disorder. In some embodiments, the subject suffers from a mood disorder. In some embodiments, the subject suffers from depression. In some embodiments, the psychiatric disorder is depression. In some embodiments, the depression is major depression. In some embodiments, the depression is unipolar depression. In some embodiments, the depression is persistent depressive disorder. In some embodiments, the subject suffers from major depression and unipolar depression. In some embodiments, the subject suffers from persistent depressive disorder. In some embodiments, the depression is seasonal affective disorder. In some embodiments, the depression is psychotic depression. In some embodiments, the depression is postpartum depression. In some embodiments, the depression is dysphoric disorder. In some embodiments, the depression is atypical depression. In some embodiments, the subject suffers from a disease treatable by a psychiatric drug. In some embodiments, the subject suffers from a disease treatable by Bupropion. In some embodiments, the subject suffers from a disease treatable by Citalopram. In some embodiments, the subject suffers from a disease treatable by Mirtazapine. In some embodiments, the subject suffers from a disease treatable by Nortriptyline. In some embodiments, the subject suffers from more than one type of psychiatric disorder. In some embodiments, the subject is a smoker. In some embodiments, the subject is a smoker in need of smoking cessation. In some embodiments, the subject is in the process of smoking cessation. In some embodiments, the subject is considering a therapeutic agent for smoking cessation.

In some embodiments, the subject is naïve to treatment. In some embodiments, the subject has not been treated with a therapeutic agent for a psychiatric disorder. In some embodiments, the subject has not been treated with a psychiatric drug. In some embodiments, the subject has not been treated with the therapeutic agent. In some embodiments, the therapeutic agent is a therapeutic agent for major depression. In some embodiments, the subject has not been treated with Bupropion. In some embodiments, the subject is naïve to treatment with Bupropion and derivatives or generics thereof. In some embodiments, the subject has not been treated with Nortriptyline. In some embodiments, the subject is naïve to treatment with Nortriptyline and derivatives or generics thereof. In some embodiments, the subject has not been treated with Citalopram. In some embodiments, the subject is naïve to treatment with Citalopram and derivatives or generics thereof. In some embodiments, the subject has not been treated with Mirtazapine. In some embodiments, the subject is naïve to treatment with Mirtazapine and derivatives or generics thereof. In some embodiments, the subject is naïve to treatment with an antidepressant. In some embodiments, the subject is naïve to treatment with a norepinephrine-dopamine reuptake inhibitor (NDRI). In some embodiments, the subject is naïve to treatment with a nicotine receptor antagonist.

In some embodiments, the subject has previously received treatment for a psychiatric disorder. In some embodiments, treatment comprises providing the therapeutic agent. In some embodiments, the treatment is a treatment that did not comprise the therapeutic agent. In some embodiments, the treatment is a first line treatment. In some embodiments, the first line treatment is a selective serotonin reuptake inhibitor (SSRI). In some embodiments, the SSRI is Citalopram. In some embodiments, the SSRI is Mirtazapine. In some embodiments, the first line treatment is a norepinephrine-dopamine reuptake inhibitor (NDRI). In some embodiments, the NDRI is Bupropion. In some embodiments, the first line treatment is a tricyclic antidepressant (TCA). In some embodiments, the TCA is Nortriptyline. In some embodiments, the first line treatment is a tetracyclic antidepressant. In some embodiments, the tetracyclic antidepressant is Mirtazapine. In some embodiments, the subject has previously received the therapeutic agent. In some embodiments, the subject has discontinued treatment. In some embodiments, the subject is a known responder to the therapeutic agent. In some embodiments, the subject is a known responder to Bupropion. In some embodiments, the subject is a known responder to Citalopram. In some embodiments, the subject is a known responder to Mirtazapine. In some embodiments, the subject is a known responder to Nortriptyline. In some embodiments, the subject is a known non-responder to the therapeutic agent. In some embodiments, the subject is a known non-responder to Bupropion. In some embodiments, the subject is a known non-responder to Citalopram. In some embodiments, the subject is a known non-responder to Mirtazapine. In some embodiments, the subject is a known non-responder to Nortriptyline.

As used herein, the terms "treated" or "treatment" of a disease, disorder, or condition encompass alleviation of at least one symptom thereof, a reduction in the severity thereof, or inhibition of the progression thereof. Treatment need not mean that the disease, disorder, or condition is totally cured. To be an effective treatment, a useful composition herein needs only to reduce the severity of a disease, disorder, or condition, reduce the severity of symptoms associated therewith, or provide improvement to a patient or subject's quality of life. Suitability for treatment need not mean that a subject will be cured by the treatment, or even that treatment will successfully alleviate at least one symptom. In some embodiments, being suitable for treatment indicates the subject is more likely than not to respond positively to the treatment or for the treatment to be effective. In some embodiments, being suitable for treatment indicates the subject is likely to respond positively to the treatment or for the treatment to be effective. In some embodiments, treatment is with the therapeutic agent alone. In some embodiments, treatment is a combination treatment that includes the therapeutic agent.

In some embodiments, the therapeutic agent is a psychiatric drug. In some embodiments, the therapeutic agent is a therapeutic that treats the subject's psychiatric disorder. In some embodiments, the therapeutic agent is an antidepressant. In some embodiments, the therapeutic agent is a treatment for depression.

In some embodiments, the antidepressant is an atypical antidepressant. In some embodiments, the therapeutic agent is a nicotine receptor antagonist. In some embodiments, the antidepressant is a nicotine receptor antagonist. In some embodiments, the antidepressant is an NDRI. In some embodiments, the therapeutic agent is an NDRI. In some embodiments, the antidepressant is a tetracyclic antidepressant. In some embodiments, the antidepressant is a tricyclic antidepressant. In some embodiments, the antidepressant is an S SRI.

In some embodiments, the NDRI is Bupropion. In some embodiments, the therapeutic agent is Bupropion. Bupropion is a biological therapeutic (biologic) with the formula 3-Chloro-N-tert-butyl-β-keto-α-methylphenethylamin, which is the same as 3-Chloro-N-tert-butyl-β-ketoamphetamine. Bupropion is commercially available and is sold under the name Wellbutrin, and Zyban among others. In some embodiments, the therapeutic agent is Bupropion, an equivalent of Bupropion, a derivative of Bupropion or a generic of Bupropion. In some embodiments, the therapeutic agent is an aminoketone. In some embodiments, suitability to be treated with Bupropion is suitability to be treated with an NDRI.

In some embodiments, the tetracyclic antidepressant is Mirtazapine. In some embodiments, the therapeutic agent is Mirtazapine. Mirtazapine is a biological therapeutic (biologic) with the formula 1,2,3,4,10,14b-Hexahydro-2-methylpyrazino[2,1-a]pyrido [2,3-c][2]benzazepine. Mirtazapine is commercially available as Remeron and others. In some embodiments, the therapeutic agent is Mirtazapine, an equivalent of Mirtazapine, a derivative of Mirtazapine or a generic of Mirtazapine. In some embodiments, the antidepressant is an atypical antidepressant. In some embodiments, suitability to be treated with Mirtazapine is suitability to be treated with a tetracyclic antidepressant. In some embodiments, suitability to be treated with Mirtazapine is suitability to be treated with an atypical antidepressant.

In some embodiments, the tricyclic antidepressant is Nortriptyline. In some embodiments, the therapeutic agent is Nortriptyline. Nortriptyline is a biological therapeutic (biologic) with the formula 1-Propanamine, 3-(10,11-dihydro-5H-dibenzo[a,d]cyclohepten-5-ylidene)-N-methyl-. Nortriptyline is commercially available as Pamelor and others. In some embodiments, the therapeutic agent is Nortriptyline, an equivalent of Nortriptyline, a derivative of Nortriptyline or a generic of Nortriptyline. In some embodiments, suitability to be treated with Nortriptyline is suitability to be treated with a tricyclic antidepressant.

In some embodiments, the SSRI is Citalopram. In some embodiments, the SSRI is Mirtazapine. In some embodiments, the therapeutic agent is Citalopram. Citalopram is a biological therapeutic (biologic) with the formula 1-[3-(Dimethylamino)-propyl]-1-(p-fluorophenyl)-5-phthalancarbonitrile. Citalopram is commercially available as Celexa and others. In some embodiments, the therapeutic agent is Citalopram, an equivalent of Citalopram, a derivative of Citalopram or a generic of Citalopram. In some embodiments, Citalopram is a racemic form of Citalopram. In some embodiments, suitability to be treated with Citalopram is suitability to be treated with an SSRI.

In some embodiments, the therapeutic agent is selected from Mirtazapine, Nortriptyline and Citalopram. In some embodiments, the therapeutic agent is selected from Bupropion, Mirtazapine, Nortriptyline and Citalopram. In some embodiments, the therapeutic agent is selected from Bupropion and Mirtazapine. In some embodiments, the therapeutic agent is selected from Bupropion and Nortriptyline. In some embodiments, the therapeutic agent is selected from Bupropion and Citalopram. In some embodiments, the therapeutic agent is selected from Bupropion, Nortriptyline and Citalopram. In some embodiments, the therapeutic agent is selected from Bupropion, Mirtazapine and Citalopram. In some embodiments, the therapeutic agent is selected from Bupropion, Mirtazapine and Nortriptyline. In some embodiments, the therapeutic agent is a tetracyclic or tricyclic antidepressant. In some embodiments, the therapeutic agent blocks a serotonin receptor. In some embodiments, the therapeutic agent blocks an adrenergic receptor. In some embodiments, the therapeutic agent is a selective serotonin reuptake inhibitor (SSRI). In some embodiments, the therapeutic agent is a serotonin and norepinephrine reuptake inhibitor (SNRI). In some embodiments, the therapeutic agent is a serotonin antagonist and reuptake inhibitor (SARI). In some embodiments, the therapeutic agent is a monoamine oxidase inhibitor (MOI). In some embodiments, the therapeutic agent is a combination of any of the agents listed herein.

In some embodiments, the method further comprises providing the non-neuronal cell from a subject. In some embodiments, the method further comprises receiving the non-neuronal cell from a subject. The term "non-neuronal cell" as used herein refers to a cell that is not a neuron. In some embodiments, the providing comprises withdrawing a non-neuronal cell from the subject. In some embodiments, the providing comprises providing a bodily fluid from the subject and isolating the non-neuronal cell. Bodily fluids include for example, blood, plasma, urine, lymph, stool, saliva, semen, and breast milk. In some embodiments, the non-neuronal cell is a blood cell.

In some embodiments, the non-neuronal cell is a peripheral blood mononuclear cell (PBMC). In some embodiments, the PBMC is a lymphoblast. In some embodiments, the non-neuronal cell is a lymphocyte. In some embodiments, the non-neuronal cell is a T cell. In some embodiments, the non-neuronal cell is a peripheral blood T cell. In some embodiments, the non-neuronal cell is a B cell. In some embodiments, the non-neuronal cell is an NK cell. In some embodiments, the non-neuronal cell is a monocyte. In some embodiments, the non-neuronal cell is a macrophage. In some embodiments, the non-neuronal cell is a cell from a lymphoblastoid cell line (LCL). In some embodiments, the non-neuronal cell is a cell from a hematopoietic stem cell (HSC). In some embodiments, the non-neuronal cell is a cell expressing the surface marker CD34 and/or CD45. In some embodiments, an HSC expresses the surface marker CD34 and/or CD45. In some embodiments, an HSC expresses CD34. In some embodiments, an HSC expressed CD45. In some embodiments, an HSC expresses CD34 and CD45. In some embodiments, the non-neuronal cell is a stem cell. In some embodiments, the non-neuronal cell is not a stem cell. In some embodiments, the stem cell is a mesenchymal stem cell (MSC). In some embodiments, the stem cell is a neuronal stem cell. In some embodiments, the stem cell is a neuronal progenitor cell. In some embodiments, the non-neuronal cell is a primary cell. In some embodiments, the non-neuronal cell is a fibroblast. In some embodiments, the non-neuronal cell is a peripheral blood mononuclear cell (PBMC). In some embodiments, the non-neuronal cell is an astrocyte. In some embodiments, the non-neuronal cell is a urine or urine-derived cell. In some embodiments, the non-neuronal cell is a cell that is reprogrammed to an induced pluripotent stem cell (iPSC). In some embodiments, the non-neuronal cell is a cell that is dedifferentiated to an iPSC. In some embodiments, the non-neuronal cell is a cell that does not naturally differentiate into a neuron. In some embodiments, the non-neuronal cell is a cell that does not differentiate into a neuron in a subject.

In some embodiments, the providing further comprises converting the non-neuronal cell into an iPSC. In some embodiments, the providing further comprises inducing the non-neuronal cell into an iPSC. In some embodiments, the providing further comprises differentiating the iPSC into the neuronal cell. In some embodiments, the providing further comprises transdifferentiating the non-neuronal cell to the neuronal cell. In some embodiments, the providing is performed in vitro. In some embodiments, the providing is performed in culture. In some embodiments, the method is performed in vitro. In some embodiments, the method is performed in culture. In some embodiments, the method is an in vitro method. In some embodiments, the method is an ex vivo method.

In some embodiments, the neuronal cell is a neuron. In some embodiments, the neuronal cell is a neuron-like cell. In some embodiments, the neuronal cell is an induced neuronal cell. In some embodiments, the neuronal cell is not a naturally occurring neuronal cell. In some embodiments, the neuronal cell is not a primary cell. In some embodiments, the neuronal cell is not a cell extracted from the subject. In some embodiments, the neuronal cell is produced in vitro. In some embodiments, the neuronal cell is produced in culture. In some embodiments, the neuronal cell is derived in vitro and/or in culture.

The term "derived" as used herein refers to conversion to a neuronal cell using any one of the suitable means known to one skilled in the art. In some embodiments, the conversion is a non-natural conversion. In some embodiments, the derivation is performed in vitro. In some embodiments, the neuronal cell is derived from an iPSC of the subject. In some embodiments, the iPSC is derived from a PBMC of the subject. In some embodiments, the iPSC is derived from a lymphocyte of the subject. Methods of generation of iPSCs from somatic cells, primary cells and cells of a cell line are all known in the art. Any such method may be employed. An exemplary method of iPSC generation is provided herein. In some embodiments, the method of generating the iPSC is the method provided herein below. Methods of differentiation of iPSCs into neurons or neuron-like cells are well known in the art, and any such method may be employed. An exemplary method of iPSC differentiation into neurons is provided herein. In some embodiments, the method of differentiating iPSCs into neurons is the method provided herein. Methods of transdifferentiating somatic cells into neurons are well known in the art and any such method may be employed. In some embodiments, the method of transdifferentiation is a method of transdifferentiating T cells to neurons. In some embodiments, the method is the method provided in Tanabe et al., 2018 "Transdifferentiation of human adult peripheral blood T cells into neurons" herein incorporated by reference in its entirety. In some embodiments, the method of transdifferentiation is a method of transdifferentiating a hematopoietic stem cell (HSC) to a neuron. In some embodiments, the method of transdifferentiation is the method provided in Lee et al., 2015 "Single Transcription Factor Conversion of Human Blood Fate to NPCs with CNS and PNS Developmental Capacity" herein incorporated by reference in its entirety. In some embodiments the method of transdifferentiation is the method provided in Sheng, et al., 2018 "A stably self-renewing adult blood-derived induced neural stem cell exhibiting patternability and epigenetic rejuvenation" herein incorporated by reference in its entirety.

The term "neuronal cell" as used herein refers to a neuron derived from any of the suitable means known to one skilled in the art. In some embodiments, the neuronal cell is derived from iPSCs. In some embodiments, the neuronal cell is derived from iPSCs derived from a non-neuronal cell from a subject. In some embodiments, the neuronal cell is a cortical neuron. In some embodiments, the cortical neuron is a frontal cortical neuron. In some embodiments, the neuronal cell is derived directly from T cells.

The term "assessing" as used herein refers to any method of determining the presence and/or level of expression of a biomarker using any one of the suitable means known to one skilled in the art. In some embodiments, assessing comprises measuring expression of the biomarker in a neuronal cell. In some embodiments, assessing comprises assessing RNA expression, morphological assessment or both. In some embodiments, expression is RNA expression, protein expression or both. In some embodiments, expression is RNA expression. In some embodiments, expression is protein expression. In some embodiments, assessment of RNA expression comprises RNA sequencing, RNA microarray analysis or PCR. In some embodiments, assessing comprises RNA sequencing, RNA microarray, PCR, or histological examination. In some embodiments, assessing comprises histological examination. In some embodiments, assessing comprises analysis of synaptic morphology. In some embodiments, assessing comprises analysis of synapse number. In some embodiments, assessing comprises post-synaptic marker analysis. In some embodiments, assessing comprises pre-synaptic marker analysis. In some embodiments, assessing comprises an analysis of gene expression. In some embodiments, assessing comprises extraction of RNA, sequencing and analysis RNA expression.

In some embodiments, assessing comprises RNA extraction from the neuronal cell. In some embodiments, assessing comprises protein extraction from the neuronal cell. In some embodiments, assessing comprises RNA isolation. In some embodiments, RNA isolation comprises mRNA isolation. In some embodiments, RNA isolation comprises total RNA isolation. In some embodiments, assessing comprises sequencing the RNA. In some embodiments, the sequencing is deep sequencing. In some embodiments, the sequencing is next generation sequencing. In some embodiments, the sequencing is transcriptome sequencing. Methods of sequencing and specifically RNAseq are well known in the art and any such method may be employed. In some embodiments, the assessing comprises analysis of the sequencing results. In some embodiments, the assessing comprises analysis of RNA expression. In some embodiments, the assessing comprises generation of expression levels or expression values for genes in the neuronal cell.

The term "biomarker" as used herein refers to a feature of a neuronal cell that indicates suitability or unsuitability of a subject to be treated with a therapeutic agent. In some embodiments, the biomarker is a gene. In some embodiments, the biomarker is a gene's expression. In some embodiments, the biomarker is a gene whose expression or change in expression is indicative of a subject's suitability or unsuitability to be treated with a therapeutic agent. In some embodiments, the biomarker is a morphological feature of the neuronal cell. In some embodiments, a change in expression is upregulation. In some embodiments, upregulation is an increase in expression. In some embodiments, a change in expression is downregulation. In some embodiments, downregulation is a decrease in expression.

In some embodiments, the at least one biomarker is a plurality of biomarkers. In some embodiments, the at least one biomarker is at least 2, 3, 4, 5, 6, 7, 8, 9 or 10 biomarkers. Each possibility represents a separate embodiment of the invention. In some embodiments, the at least one biomarker is a combination of biomarkers. In some embodiments, the at least one biomarker is a panel of biomarkers. In some embodiments, at least one biomarker is 2 biomarkers. In some embodiments, at least one biomarker is 3 biomarkers. In some embodiments, at least one biomarker is 4 biomarkers. In some embodiments, at least one biomarker is 5 biomarkers. In some embodiments, at least one biomarker is 6 biomarkers. In some embodiments, at least one biomarker is 7 biomarkers. In some embodiments, at least one biomarker is 8 biomarkers. In some embodiments, at least one biomarker is 9 biomarkers. In some embodiments, at least one biomarker is 10 biomarkers.

In some embodiments, the biomarker is a gene whose expression level at baseline indicates suitability of a subject to be treated with a therapeutic agent. In some embodiments, the biomarker is a gene whose expression level at baseline is different between cells derived from responders and non-responders. In some embodiments, the difference is a statistically significant difference. In some embodiments, the biomarker is a gene whose expression above a predetermined threshold at baseline indicates suitability of a subject to be treated with a therapeutic agent. In some embodiments, the biomarker is a gene from Table 1. In some embodiments, a gene from Table 1 is a biomarker whose expression above a predetermined threshold at baseline indicates suitability of a subject to be treated with a therapeutic agent. In some embodiments, the biomarker is a gene whose expression below a predetermined threshold at baseline indicates suitability of a subject to be treated with a therapeutic agent. In some embodiments, the biomarker is a gene from Table 2. In some embodiments, a gene from Table 2 is a biomarker whose expression below a predetermined threshold at baseline indicates suitability of a subject to be treated with a therapeutic agent. In some embodiments, the biomarker is a gene provided in either Table 1 or Table 2.

In some embodiments, a significant gene in Table 1 is a biomarker. In some embodiments, a significant gene from Table 1 is a gene selected from NPY2R, MMS22L, CASP8AP2, BRIP1, SIM1, DHFR, RBL1, MGAM, WNT8B, APAF1, MAP2K6, BLM, LBR, CALCR, ZWILCH, LONRF3, CIP2A, SMC2, C4orf46, DLX2, EIF1AX, LRRC40, LRRC8B, MCM10, TIGAR, ALG10, VGLL3, ZNF730, SLC25A24, RTKN2, BUB3, DNA2, TFAM, PCLAF, TAF7L, OSBPL11, GNB4, UTP20, MCM8, ATAD5, EXO1, CENPE, NUCKS1, FBXO5, SYCP2L, NUP50, RASA2, KNL1, SRSF1, SLC25A13, RIT2, FEZF1, KIF11, PRKDC, CHEK1, DLX1, CENPI, KIF18A, NUP155, CHML, HAUS6, TRA2B, PHF6, QSER1, ZNF678, FAM135A, PDYN, EXOC6, VMA21, CKAP2, CENPQ, DEPDC1B, XKR9, HOOK3, SNRNP48, TMPO, LCLAT1, VPS13A, RRM2, DTL, PAQR3, TAF9B, CTDSPL2, ZNF260, ZPLD1, APIS, DCLRE1A, ANGEL2, MPHOSPH6, PIGW, AGPS, FANCB, SIKE1, GPC3, LRRN3, SFRP4, ZNF347, CYP26A1, TRNT1, PCDH19, WASF3, ATAD2, C5orf34, STK38L, ME2, MELK, PDS5A, CENPF, CDC7, COMMD2, PCNA, MTBP, ZMYM4, SPIN4, TAF1A, MRPL19, BCLAF3, NUP107, RNGTT, CBX5, RBBP8, CNOT6, CDH6, TOP2A, SMC4, EX005, MCM4, PTPN13, MAPK1IP1L, SUV39H2, DMRTA1, DSCC1, ERCC8, NDC1, ASPM, RADX, LRRC3B, SELENOI, NEIL3, FANCI, USP14, TYW3, C18orf54, FKBP5, XRN2, MGA, FANCM, HELLS, ITGA6, NCAPG, CNTNAP2, ZNF66, XRCC2, ANLN, C9orf40, NUDT21, HNRNPA3, ADAL, RBM12, H2AFV, CREB1, FXN, ARHGAP11A, CDCA2, NBN, TARDBP, SMARCAD1, BDP1, and SRBD1. In some embodiments, the biomarker is at least one significant gene from Table 1. In some embodiments, the biomarker is at least two significant gene from Table 1. In some embodiments, the biomarker is at least three significant gene from Table 1. In some embodiments, the biomarker is at least four significant gene from Table 1. In some embodiments, the biomarker is at least five significant gene from Table 1. In some embodiments, the biomarker is at least six significant gene from Table 1. In some embodiments, the biomarker is at least seven significant gene from Table 1. In some embodiments, the biomarker is at least eight significant gene from Table 1. In some embodiments, the biomarker is at least nine significant gene from Table 1. In some embodiments, the biomarker is at least ten significant gene from Table 1.

In some embodiments, the gene is selected from FEZF1, RIT2, XKR9, and DLX1. In some embodiments, the gene is selected from FEZF1, RIT2, XKR9, and DLX1 and upregulation at baseline, or expression above a predetermined threshold, is indicative that a subject is suitable to be treated by Mirtazapine. In some embodiments, the gene is selected from FEZF1, RIT2, XKR9, and DLX1 and upregulation at baseline, or expression above a predetermined threshold, is indicative that a subject is suitable to be treated by Bupropion. In some embodiments, the gene is selected from FEZF1, RIT2, XKR9, and DLX1 and upregulation at baseline, or expression above a predetermined threshold, is indicative that a subject is suitable to be treated by Bupropion or Mirtazapine. In some embodiments, a gene selected from FEZF1, RIT2, XKR9, and DLX1 is FEZF1. In some embodiments, a gene selected from FEZF1, RIT2, XKR9, and DLX1 is RIT2. In some embodiments, a gene selected from FEZF1, RIT2, XKR9, and DLX1 is XKR9. In some embodiments, a gene selected from FEZF1, RIT2, XKR9, and DLX1 is DLX1.

In some embodiments, a significant gene in Table 2 is a biomarker. In some embodiments, a significant gene from Table 2 is a gene selected from LIN37, CYP27A1, GSTT2B, DRGX, SKOR2, COLEC11, TRIM47, KIAA1211L, COL8A2, PHOX2B, HSD3B7, SLPI, ADAMTSL2, GAA, CTSD, FTH1, HS6ST1, ALDOA, TAF1C, COL11A2, NPR2, OGFR, CEMIP, TNFRSF14, CXCL8, ELN, PENK, IRF2BPL, PSD4, USH1C, SLC45A2, RPS26, JOSD2, NCMAP, GATD3B, PLEKHD1, IL17RC, PTGER4, TOM1, GLIS2, ZNF835, EN2, PNPLA7, ADAMTS15, COL6A1, TSHZ3, TULP1, KCNF1, PI4 KB, NTNG1, PCSK9, TYRP1, PRSS33, JUNB, HOXB5, BDKRB2, F12, FRMPD1, TLX3, PADI2, RARA, TBC1D10B, STARD3, NAGA, SLC2A1, PIEZO2, APOL2, PGPEP1, COL9A2, KCNA1, ACAN, TRAF1, NNMT, ZBTB4, WBP2, FAM3A, EPHB3, LOX, PGM1, MAL, ZSWIM8, PSMB10, PPP6R1, TRIM8, AIFM2, PIGS, FAM163B, SLC38A3, CCER2, PLPP4, RABEP2, LOXL1, THBS2, DUSP1, CCDC187, P2RX2, NDRG1, ITPRIP, ACOT1, RARRES2, SST, TMEM72, LIMS2, PVALB, CHST8, NDUFA4L2, YIPF3, YPEL3, ISL2, FZD9, RPRM, CXCL6, GRAMD1A, PPM1M, PDZRN3, NTNG2, SSH3, ABCD1, PRCD, WFIKKN2, C1R, FGF10, NKX3-2, FSTL3, C9orf24, HOXB6, FBLN1, COL5A3, C1S, NCOR2, TMEM175, C20orf85, and AVIL. In some embodiments, the biomarker is at least one significant gene from Table 2. In some embodiments, the biomarker is at least two significant gene from Table 2. In some embodiments, the biomarker is at least three significant gene from Table 2. In some embodiments, the biomarker is at least four significant gene from Table 2. In some embodiments, the biomarker is at least five significant gene from Table 2. In some embodiments, the biomarker is at least six significant gene from Table 2. In some embodiments, the biomarker is at least seven significant gene from Table 2. In some embodiments, the biomarker is at least eight significant gene from Table 2. In some embodiments, the biomarker is at least nine significant gene from Table 2. In some embodiments, the biomarker is at least ten significant gene from Table 2.

In some embodiments, the gene is MFAP4. In some embodiments, the gene is MFAP4 and downregulation at baseline, or expression below a predetermined threshold, is indicative that a subject is suitable to be treated by Bupropion. In some embodiments, the gene is MFAP4 and downregulation at baseline, or expression below a predetermined threshold, is indicative that a subject is suitable to be treated by Mirtazapine. In some embodiments, the gene is MFAP4 and downregulation at baseline, or expression below a predetermined threshold, is indicative that a subject is suitable to be treated by Bupropion or Mirtazapine. In some embodiments, the gene is selected from MFAP4, ELN and EYA2. In some embodiments, the gene is selected from MFAP4, ELN and EYA2 and downregulation at baseline, or expression below a predetermined threshold, is indicative that a subject is suitable to be treated by Bupropion. In some embodiments, the gene is selected from MFAP4, ELN and EYA2 and downregulation at baseline, or expression below a predetermined threshold, is indicative that a subject is suitable to be treated by Mirtazapine. In some embodiments, the gene is selected from MFAP4, ELN and EYA2 and downregulation at baseline, or expression below a predetermined threshold, is indicative that a subject is suitable to be treated by Bupropion or Mirtazapine.

In some embodiments, the gene is selected from ELN and EYA2. In some embodiments, the gene is selected from ELN and EYA2 and downregulation at baseline, or expression below a predetermined threshold, is indicative that a subject is suitable to be treated by Bupropion. In some embodiments, the gene is selected from ELN and EYA2 and downregulation at baseline, or expression below a predetermined threshold, is indicative that a subject is suitable to be treated by Mirtazapine. In some embodiments, the gene is selected from ELN and EYA2 and downregulation at baseline, or expression below a predetermined threshold, is indicative that a subject is suitable to be treated by Bupropion or Mirtazapine. In some embodiments, a gene selected from ELN and EYA2 is ELN. In some embodiments, a gene selected from ELN and EYA2 is EYAs.

In some embodiments, the predetermined threshold is expression in non-responders. In some embodiments, the predetermined threshold is average expression in non-responders. In some embodiments, the predetermined threshold is expression in non-responders before treatment. In some embodiments, the predetermined threshold is average expression in non-responders before treatment. In some embodiments, the predetermined threshold is expression in non-responders after treatment. In some embodiments, the predetermined threshold is average expression in non-responders after treatment. In some embodiments, the predetermined threshold is expression in untreated neurons. In some embodiments, the predetermined threshold is average expression in untreated neurons. In some embodiments, untreated neurons are derived from responders. In some embodiments, the predetermined threshold is expression in responders before treatment. In some embodiments, the predetermined threshold is average expression in responders before treatment. In some embodiments, before treatment is without treatment. In some embodiments, before treatment is treatment with a control. In some embodiments, untreated neurons are neurons treated with a control. In some embodiments, the control is buffer. In some embodiments, the control is PBS.

In some embodiments, the biomarker is a gene whose expression level is different in cells derived from responders and non-responders after treatment with a therapeutic agent. In some embodiments, the biomarker is a gene whose expression above a predetermined threshold after treatment indicates suitability of a subject to be treated with a therapeutic agent. In some embodiments, the biomarker is a gene from Table 3. In some embodiments, a gene from Table 3 is a biomarker whose expression above a predetermined threshold after treatment indicates suitability of a subject to be treated with a therapeutic agent. In some embodiments, the biomarker is a gene whose expression below a predetermined threshold after treatment indicates suitability to be treated with a therapeutic agent. In some embodiments, the biomarker is a gene from Table 4. In some embodiments, a gene from Table 4 is a biomarker whose expression below a predetermined threshold after treatment indicates suitability of a subject to be treated with a therapeutic agent. In some embodiments, the biomarker is a gene provided in either Table 3 or Table 4. In some embodiments, the genes in Table 3 or Table 4 are biomarkers for suitability to be treated with Bupropion. In some embodiments, the genes in Table 3 or Table 4 are biomarkers for suitability to be treated with a NDRI.

In some embodiments, a significant gene in Table 3 is a biomarker. In some embodiments, a significant gene from Table 3 is a gene selected from SLC25A13, SPIN4, SLC25A17, SIM1, NPY2R, ZC3H13, WNT8B, F8, TIGAR, DMRTA1, ZWILCH, WNT10B, GPC3, ZBTB24, NOS2, EIF1AX, HLA-DMA, CHML, DHFR, OSBPL11, MCUR1, CDH6, TFAM, SNRNP48, MEIOC, BAG4, STK38L, HESX1, LRRC8B, MGA, FREM2, SFRP4, TSGA10IP, MDN1, MCM4, CCDC150, HAUS6, TNFRSF13C, PPAT, SLC7A11, ARHGEF26, S100A13, FBXO22, SIKE1, ANKRD27, NFKBID, RNGTT, POU5F1B, PRKDC, MGME1, TXNRD1, SMG1, DLX2, WWP1, SYCP2L, ZNF347, PTPN13, PCGF5, USP37, LGI1, SIGLEC10, PHF6, ITGA6, SELENOI, ATAD5, ADAL, MZT1, DNA2, and PAWR. In some embodiments, the biomarker is at least one significant gene from Table 3. In some embodiments, the biomarker is at least two significant gene from Table 3. In some embodiments, the biomarker is at least three significant gene from Table 3. In some embodiments, the biomarker is at least four significant gene from Table 3. In some embodiments, the biomarker is at least five significant gene from Table 3. In some embodiments, the biomarker is at least six significant gene from Table 3. In some embodiments, the biomarker is at least seven significant gene from Table 3. In some embodiments, the biomarker is at least eight significant gene from Table 3. In some embodiments, the biomarker is at least nine significant gene from Table 3. In some embodiments, the biomarker is at least ten significant gene from Table 3.

In some embodiments, the gene is selected from TGIF1, SLC47A1, FOSL1, SLC2A3, and PROCR. In some embodiments, the gene is selected from TGIF1, SLC47A1, FOSL1, SLC2A3, and PROCR and upregulation after treatment, or expression above a predetermined threshold, is indicative that a subject is suitable to be treated by Mirtazapine. In some embodiments, the gene is selected from TGIF1, SLC47A1, FOSL1, SLC2A3, and PROCR and upregulation after treatment, or expression above a predetermined threshold, is indicative that a subject is suitable to be treated by Bupropion. In some embodiments, the gene is selected from TGIF1, SLC47A1, FOSL1, SLC2A3, and PROCR and upregulation after treatment, or expression above a predetermined threshold, is indicative that a subject is suitable to be treated by Bupropion or Mirtazapine. In some embodiments, a gene selected from TGIF1, SLC47A1, FOSL1, SLC2A3, and PROCR is TGIF1. In some embodiments, a gene selected from TGIF1, SLC47A1, FOSL1, SLC2A3, and PROCR is SLC47A1. In some embodiments, a gene selected from TGIF1, SLC47A1, FOSL1, SLC2A3, and PROCR is FOSL1. In some embodiments, a gene selected from TGIF1, SLC47A1, FOSL1, SLC2A3, and PROCR is SLC2A3. In some embodiments, a gene selected from TGIF1, SLC47A1, FOSL1, SLC2A3, and PROCR is PROCR.

In some embodiments, the gene is selected from DLX2, SIM1, FOSL1 and PROCR. In some embodiments, the gene is selected from DLX2, SIM1, FOSL1 and PROCR and upregulation after treatment, or expression above a predetermined threshold, is indicative that a subject is suitable to be treated by Mirtazapine. In some embodiments, the gene is selected from DLX2, SIM1, FOSL1 and PROCR and upregulation after treatment, or expression above a predetermined threshold, is indicative that a subject is suitable to be treated by Bupropion. In some embodiments, the gene is selected from DLX2, SIM1, FOSL1 and PROCR and upregulation after treatment, or expression above a predetermined threshold, is indicative that a subject is suitable to be treated by Bupropion or Mirtazapine. In some embodiments, a gene selected from DLX2, SIM1, FOSL1 and PROCR is DLX2. In some embodiments, a gene selected from DLX2, SIM1, FOSL1 and PROCR is SIM1. In some embodiments, a gene selected from DLX2, SIM1, FOSL1 and PROCR is FOSL1. In some embodiments, a gene selected from DLX2, SIM1, FOSL1 and PROCR is PROCR.

In some embodiments, the gene is selected from DLX2, and SIM1. In some embodiments, the gene is selected from DLX2, and SIM1 and upregulation after treatment, or expression above a predetermined threshold, is indicative that a subject is suitable to be treated by Mirtazapine. In some embodiments, the gene is selected from DLX2, and SIM1 and upregulation after treatment, or expression above a predetermined threshold, is indicative that a subject is suitable to be treated by Bupropion. In some embodiments, the gene is selected from DLX2, and SIM1 and upregulation after treatment, or expression above a predetermined threshold, is indicative that a subject is suitable to be treated by Bupropion or Mirtazapine. In some embodiments, a gene selected from DLX2, and SIM1 is DLX2. In some embodiments, a gene selected from DLX2, and SIM1 is SIM1.

In some embodiments, the gene is selected from DLX2, SIM1, TGIF1, SLC47A1, FOSL1, SLC2A3, and PROCR. In some embodiments, the gene is selected from DLX2, TGIF1, SLC47A1, FOSL1, SLC2A3, and PROCR and upregulation after treatment, or expression above a predetermined threshold, is indicative that a subject is suitable to be treated by Mirtazapine. In some embodiments, the gene is selected from DLX2, SIM1, TGIF1, SLC47A1, FOSL1, SLC2A3, and PROCR and upregulation after treatment, or expression above a predetermined threshold, is indicative that a subject is suitable to be treated by Bupropion. In some embodiments, the gene is selected from DLX2, SIM1, TGIF1, SLC47A1, FOSL1, SLC2A3, and PROCR and upregulation after treatment, or expression above a predetermined threshold, is indicative that a subject is suitable to be treated by Bupropion or Mirtazapine.

In some embodiments, the gene is COL17A1. In some embodiments, the gene is COL17A1 and upregulation after treatment, or expression above a predetermined threshold, is indicative that a subject is suitable to be treated by Citalopram. In some embodiments, the gene is COL17A1 and upregulation after treatment, or expression above a predetermined threshold, is indicative that a subject is suitable to be treated by Bupropion. In some embodiments, the gene is COL17A1 and upregulation after treatment, or expression above a predetermined threshold, is indicative that a subject is suitable to be treated by Bupropion or Citalopram.

In some embodiments, a significant gene in Table 4 is a biomarker. In some embodiments, a significant gene from Table 4 is a gene selected from MAFB, DRGX, ADAMTSL2, FRMPD1, POU4F1, COL8A2, INMT, CDKN1C, NNMT, SKOR2, NPR2, CXCL8, PSMB9, CEMIP, KLHL35, PSMB8, PIRT, TMEM176B, VLDLR, INHBB, ACOT1, COL15A1, TNFRSF14, TBC1D2, PENK, TRAF1, APOL2, TRPV2, ASPN, FAM20C, BDKRB2, TLX3, TMEM176A, CPNE5, GALNT14, THBS2, PLEKHD1, TSHZ3, ELN, PLCH2, NTNG2, KCNA1, TAF1C, LGALS3BP, IRF2BPL, COLEC11, ADAMTS15, ITPRIP, ADAMTSL1, CABP7, CACNA1H, CPNE9, GFRA2, ABCC6, FNDC5, SLC2A1, CCER2, CPA4, PIEZO2, PLD5, HS6ST1, TMEM163, PSD4, EYA2, PADI2, EGFLAM, C1S, PALM, FGF1, PRSS33, C1R, TLR6, PHOX2B, TLX1, OPTN, TAP1, PTGER2, P4HA3, PLAC9, NFIX, TREM1, KCNJ5, COL6A1, ADAMTS8, GLIS2, HES6, ALDOC, FMOD, FBLN5, USP18, CHST8, LRFN5, LOX, NKX3-2, USH1C, ZNF575, OPRK1, SECTM1, SAMD9L, HCN1, CXCL6, OPRM1, TAP2, ARHGEF28, GPBAR1, IAH1, KHDC1, PARP10, OLFML2B, PODN, ARL17B, SYNC, PRPH, TRMT9B, KDM4B, NDUFA4L2, CCDC183, RBP1, PTGDS, JOSD2, AQP6, CXCL2, KIF26A, C5orf63, CCDC187, EFEMP2, SUN2, SAMD9, POLR2J3, RAB42, RBMS3, SST, OGFR, PRCD, RPH3A, COL1A1, IGFBP5, HOXB5, TMC3, TF, MX2, SH3TC2, LOXL1, OTOG, MAB21L2, SLC38A3, CD151, MGP, RSAD2, PXDNL, DYRK1B, MCC, MKX, SUSD1, ADAMTS4, IL17RC, ZFPM1, EPHB3, SLC17A7, ISLR, LURAP1L, GAA, HMX1, DHRS3, ARHGAP23, S100B, HS3ST2, TRIM8, VSTM2B, SMPD1, SLC4A4, LYPD1, TMEM175, and PLPP4. In some embodiments, the biomarker is at least one significant gene from Table 4. In some embodiments, the biomarker is at least two significant gene from Table 4. In some embodiments, the biomarker is at least three significant gene from Table 4. In some embodiments, the biomarker is at least four significant gene from Table 4. In some embodiments, the biomarker is at least five significant gene from Table 4. In some embodiments, the biomarker is at least six significant gene from Table 4. In some embodiments, the biomarker is at least seven significant gene from Table 4. In some embodiments, the biomarker is at least eight significant gene from Table 4. In some embodiments, the biomarker is at least nine significant gene from Table 4. In some embodiments, the biomarker is at least ten significant gene from Table 4.

In some embodiments, the gene is ELN. In some embodiments, the gene is ELN and downregulation after treatment, or expression below a predetermined threshold, is indicative that a subject is suitable to be treated by Mirtazapine. In some embodiments, the gene is ELN and downregulation after treatment, or expression below a predetermined threshold, is indicative that a subject is suitable to be treated by Bupropion. In some embodiments. In some embodiments, the gene is ELN and downregulation after treatment, or expression below a predetermined threshold, is indicative that a subject is suitable to be treated by Bupropion or Mirtazapine.

In some embodiments, the gene is selected from GRIN2B, RIT2, MTSS1, HPCAL4, PEG3, GCK, ADGRG1, GRIK2, ATAT1, NEGR1, CELF3, GAD2, and TMEM151B. In some embodiments, the gene is selected from GRIN2B, RIT2, MTSS1, HPCAL4, PEG3, GCK, ADGRG1, GRIK2, ATAT1, NEGR1, CELF3, GAD2, and TMEM151B and downregulation after treatment, or expression below a predetermined threshold, is indicative that a subject is suitable to be treated by Mirtazapine. In some embodiments, the gene is selected from GRIN2B, RIT2, MTSS1, HPCAL4, PEG3, GCK, ADGRG1, GRIK2, ATAT1, NEGR1, CELF3, GAD2, and TMEM151B and downregulation after treatment, or expression below a predetermined threshold, is indicative that a subject is suitable to be treated by Bupropion. In some embodiments. In some embodiments, the gene is selected from GRIN2B, RIT2, MTSS1, HPCAL4, PEG3, GCK, ADGRG1, GRIK2, ATAT1, NEGR1, CELF3, GAD2, and TMEM151B and downregulation after treatment, or expression below a predetermined threshold, is indicative that a subject is suitable to be treated by Bupropion or Mirtazapine. In some embodiments, a gene selected from GRIN2B, RIT2, MTSS1, HPCAL4, PEG3, GCK, ADGRG1, GRIK2, ATAT1, NEGR1, CELF3, GAD2, and TMEM151B is GRIN2B. In some embodiments, a gene selected from GRIN2B, RIT2, MTSS1, HPCAL4, PEG3, GCK, ADGRG1, GRIK2, ATAT1, NEGR1, CELF3, GAD2, and TMEM151B is RIT2. In some embodiments, a gene selected from GRIN2B, RIT2, MTSS1, HPCAL4, PEG3, GCK, ADGRG1, GRIK2, ATAT1, NEGR1, CELF3, GAD2, and TMEM151B is MTSS1. In some embodiments, a gene selected from GRIN2B, RIT2, MTSS1, HPCAL4, PEG3, GCK, ADGRG1, GRIK2, ATAT1, NEGR1, CELF3, GAD2, and TMEM151B is HPCAL4. In some embodiments, a gene selected from GRIN2B, RIT2, MTSS1, HPCAL4, PEG3, GCK, ADGRG1, GRIK2, ATAT1, NEGR1, CELF3, GAD2, and TMEM151B is PEG3. In some embodiments, a gene selected from GRIN2B, RIT2, MTSS1, HPCAL4, PEG3, GCK, ADGRG1, GRIK2, ATAT1, NEGR1, CELF3, GAD2, and TMEM151B is GCK. In some embodiments, a gene selected from GRIN2B, RIT2, MTSS1, HPCAL4, PEG3, GCK, ADGRG1, GRIK2, ATAT1, NEGR1, CELF3, GAD2, and TMEM151B is ADGRG1. In some embodiments, a gene selected from GRIN2B, RIT2, MTSS1, HPCAL4, PEG3, GCK, ADGRG1, GRIK2, ATAT1, NEGR1, CELF3, GAD2, and TMEM151B is GRIK2. In some embodiments, a gene selected from GRIN2B, RIT2, MTSS1, HPCAL4, PEG3, GCK, ADGRG1, GRIK2, ATAT1, NEGR1, CELF3, GAD2, and TMEM151B is ATAT1. In some embodiments, a gene selected from GRIN2B, RIT2, MTSS1, HPCAL4, PEG3, GCK, ADGRG1, GRIK2, ATAT1, NEGR1, CELF3, GAD2, and TMEM151B is NEGR1. In some embodiments, a gene selected from GRIN2B, RIT2, MTSS1, HPCAL4, PEG3, GCK, ADGRG1, GRIK2, ATAT1, NEGR1, CELF3, GAD2, and TMEM151B is CELF3. In some embodiments, a gene selected from GRIN2B, RIT2, MTSS1, HPCAL4, PEG3, GCK, ADGRG1, GRIK2, ATAT1, NEGR1, CELF3, GAD2, and TMEM151B is GAD2. In some embodiments, a gene selected from GRIN2B, RIT2, MTSS1, HPCAL4, PEG3, GCK, ADGRG1, GRIK2, ATAT1, NEGR1, CELF3, GAD2, and TMEM151B is TMEM151B.

In some embodiments, the gene is selected from ELN, GRIN2B, RIT2, MTSS1, HPCAL4, PEG3, GCK, ADGRG1, GRIK2, ATAT1, NEGR1, CELF3, GAD2, and TMEM151B. In some embodiments, the gene is selected from ELN, GRIN2B, RIT2, MTSS1, HPCAL4, PEG3, GCK, ADGRG1, GRIK2, ATAT1, NEGR1, CELF3, GAD2, and TMEM151B and downregulation after treatment, or expression below a predetermined threshold, is indicative that a subject is suitable to be treated by Mirtazapine. In some embodiments, the gene is selected from ELN, GRIN2B, RIT2, MTSS1, HPCAL4, PEG3, GCK, ADGRG1, GRIK2, ATAT1, NEGR1, CELF3, GAD2, and TMEM151B and downregulation after treatment, or expression below a predetermined threshold, is indicative that a subject is suitable to be treated by Bupropion. In some embodiments. In some embodiments, the gene is selected from ELN, GRIN2B, RIT2, MTSS1, HPCAL4, PEG3, GCK, ADGRG1, GRIK2, ATAT1, NEGR1, CELF3, GAD2, and TMEM151B and downregulation after treatment, or expression below a predetermined threshold, is indicative that a subject is suitable to be treated by Bupropion or Mirtazapine.

In some embodiments, the gene is selected from NR1I3, MYH3, DES, SLCO2B1, and SRL. In some embodiments, the gene is selected from NR1I3, MYH3, DES, SLCO2B1, and SRL and downregulation after treatment, or expression below a predetermined threshold, is indicative that a subject is suitable to be treated by Citalopram. In some embodiments, the gene is selected from NR1I3, MYH3, DES, SLCO2B1, and SRL and downregulation after treatment, or expression below a predetermined threshold, is indicative that a subject is suitable to be treated by Bupropion. In some embodiments. In some embodiments, the gene is selected from NR1I3, MYH3, DES, SLCO2B1, and SRL and downregulation after treatment, or expression below a predetermined threshold, is indicative that a subject is suitable to be treated by Bupropion or Citalopram. In some embodiments, a gene selected from NR1I3, MYH3, DES, SLCO2B1, and SRL is NR1I3. In some embodiments, a gene selected from NR1I3, MYH3, DES, SLCO2B1, and SRL is MYH3. In some embodiments, a gene selected from NR1I3, MYH3, DES, SLCO2B1, and SRL is DES. In some embodiments, a gene selected from NR1I3, MYH3, DES, SLCO2B1, and SRL is SLCO2B1. In some embodiments, a gene selected from NR1I3, MYH3, DES, SLCO2B1, and SRL is SRL.

In some embodiments, the biomarker is a gene whose expression level is different before and after treatment in cells derived from responders. In some embodiments, the biomarker is a gene whose upregulation after treatment indicates suitability to be treated with a therapeutic agent. In some embodiments, the biomarker is a gene from Table 5. In some embodiments, the biomarker is a gene from Table 5 and upregulation after treatment indicates suitability to be treated with a therapeutic agent. In some embodiments, the biomarker is a gene whose downregulation after treatment indicates suitability to be treated with a therapeutic agent. In some embodiments, the biomarker is a gene from Table 6. In some embodiments, the biomarker is a gene from Table 6 and downregulation after treatment indicates suitability to be treated with a therapeutic agent. In some embodiments, the genes in Table 5 or Table 6 are biomarkers for suitability to be treated with Bupropion. In some embodiments, the genes in Table 5 or Table 6 are biomarkers for suitability to be treated with an NDRI.

In some embodiments, a significant gene in Table 5 is a biomarker. In some embodiments, a significant gene from Table 5 is a gene selected from CXCL11, PTPRQ, COX16, RSAD2, LLPH, TSTD2, HS3ST5, CHMP4A, PSD3, ARL17B, FGF1, INMT, LHFPL3, SCN9A, MINDY3, ZFP69B, and ZNF221. In some embodiments, the biomarker is at least one significant gene from Table 5. In some embodiments, the biomarker is at least two significant gene from Table 5. In some embodiments, the biomarker is at least three significant gene from Table 5. In some embodiments, the biomarker is at least four significant gene from Table 5. In some embodiments, the biomarker is at least five significant gene from Table 5. In some embodiments, the biomarker is at least six significant gene from Table 5. In some embodiments, the biomarker is at least seven significant gene from Table 5. In some embodiments, the biomarker is at least eight significant gene from Table 5. In some embodiments, the biomarker is at least nine significant gene from Table 5. In some embodiments, the biomarker is at least ten significant gene from Table 5.

In some embodiments, a significant gene in Table 6 is a biomarker. In some embodiments, a significant gene from Table 6 is a gene selected from LIN37, NFKBID, TCF7, DUSP23, TENT5B, UGT3A2, CCDC51, CTNS, PYCARD, ABHD4, TEKT3, SMPDL3B, KLC3, PNKP, SPNS1, FAM117A, PPL, ZNF425, MT2A, PPP1R1B, CKS1B, LGR6, ART5, ADRA2B, ZNF394, ETV5, VWA2, CDC42BPG, TRAF3IP2, TXNRD2, RAB43, APOE, TYW1B, TOM1, GPR89A, HAUS8, TNNI3, TJP3, RNASEK, MACROD1, DDX55, MAP4K1, MADCAM1, NMRK2, RARRES2, GABRD, CTSD, FBXO2, MT1X, LRRC2, SLC45A2, KLHL21, RILPL1, PSMB10, LHPP, RABEP2, and LARGE2. In some embodiments, the biomarker is at least one significant gene from Table 6. In some embodiments, the biomarker is at least two significant gene from Table 6. In some embodiments, the biomarker is at least three significant gene from Table 6. In some embodiments, the biomarker is at least four significant gene from Table 6. In some embodiments, the biomarker is at least five significant gene from Table 6. In some embodiments, the biomarker is at least six significant gene from Table 6. In some embodiments, the biomarker is at least seven significant gene from Table 6. In some embodiments, the biomarker is at least eight significant gene from Table 6. In some embodiments, the biomarker is at least nine significant gene from Table 6. In some embodiments, the biomarker is at least ten significant gene from Table 6.

In some embodiments, the biomarker is a morphological feature of a neuronal cell indicating suitability of a subject to be treated with a therapeutic agent. In some embodiments, the biomarker is a change in a morphological feature of a neuronal cell indicating suitability of a subject to be treated with a therapeutic agent. In some embodiments, the morphological feature is selected from synapse number, synapse density, synapse colocalization, synapse perimeter length, dendrite length, dendritic spine length and a combination thereof. In some embodiments, the biomarker is a change in a morphological feature of a neuronal cell indicating suitability of a subject to be treated with a therapeutic agent. In some embodiments, the morphological feature is selected from dendritic spine type, synapse number, synapse density, synapse colocalization, synapse perimeter length, dendrite length, dendritic spine length, dendritic branching and a combination thereof. In some embodiments, the morphological feature is selected from synapse number, synapse density, synapse colocalization, synapse perimeter length, dendrite length, dendritic spine length, and a combination thereof. In some embodiments, the morphological feature is dendritic spine type. In some embodiments, the dendritic spine type is selected from thin, mushroom, filopodia, stubby, and branched. In some embodiments, the morphological feature is synapse number. In some embodiments, the morphological feature is synapse density. In some embodiments, the morphological feature is synapse colocalization. In some embodiments, the morphological feature is synapse perimeter length. In some embodiments, the morphological feature is dendrite length. In some embodiments, the morphological feature is dendritic spine length. In some embodiments, the morphological feature is dendritic spine length in a specific dendritic spine type. In some embodiments, the dendritic spine type is mushroom spines. In some embodiments, the dendritic spine type is stubby spines. In some embodiments, the dendritic spine type is filopodia spines. In some embodiments, the dendritic spine type is thin spines. In some embodiments, the morphological feature is dendritic branching. In some embodiments, dendritic branching is measured by the number of dendritic branches. In some embodiments, the morphological feature is a combination of the above.

Measuring morphological features of cells is well known in the art and can be performed using routine microscopy techniques. In some embodiments, measuring a morphological feature comprises analysis with a microscope. In some embodiments, the microscope is a confocal microscope. In some embodiments, the microscope is a light microscope. In some embodiments, the analysis comprises counting the morphological feature. In some embodiments, the analysis comprises measuring the length of the morphological feature. In some embodiments, the analysis comprises measuring the perimeter of the morphological feature.

In some embodiments, the biomarker is the length of the perimeter of post-synaptic puncta and indicative of suitability of a subject to be treated with a therapeutic agent. In some embodiments, baseline post-synaptic puncta perimeter length below a predetermined threshold is indicative of suitability to be treated. In some embodiments, the biomarker is post-synaptic puncta perimeter length. In some embodiments, post-synaptic puncta perimeter length after treatment below a threshold is indicative of suitability to be treated. Post-synaptic puncta can be identified by any maker of post-synaptic neurons known in the art. Examples of post-synaptic markers include, but are not limited to PSD95, Homer1, PSD93, Shank, GLUR1 and NR1. In some embodiments, the post-synaptic marker is PSD95. In some embodiments, perimeter of post-synaptic puncta is indicative of suitability to be treated with Bupropion. In some embodiments, perimeter of post-synaptic puncta is indicative of suitability to be treated with an NDRI.

In some embodiments, the biomarker is the length of the perimeter of pre-synaptic puncta and indicative of suitability of a subject to be treated with a therapeutic agent. In some embodiments, baseline pre-synaptic puncta perimeter length below a predetermined threshold is indicative of suitability to be treated. In some embodiments, the biomarker is pre-synaptic puncta perimeter length. In some embodiments, decrease in pre-synaptic puncta perimeter length after treatment is indicative of unsuitability to be treated. Pre-synaptic puncta can be identified by any maker of pre-synaptic neurons known in the art. Examples of pre-synaptic markers include, but are not limited to synapsin, synaptophysin, Bassoon, and synaptobrevin. In some embodiments, the pre-synaptic marker is synapsin. In some embodiments, perimeter of pre-synaptic puncta is indicative of suitability to be treated with Bupropion. In some embodiments, perimeter of pre-synaptic puncta is indicative of suitability to be treated with an NDRI.

In some embodiments, the biomarker is a change in a post-synaptic marker and indicative of a subject's suitability to be treated with a therapeutic agent. In some embodiments, the biomarker is the number of post-synaptic marker positive puncta and indicative of a subject's suitability to be treated with a therapeutic agent. In some embodiments, the biomarker is the density of post-synaptic marker positive puncta and indicative of a subject's suitability to be treated with a therapeutic agent. In some embodiments, the post-synaptic marker is PSD95. In some embodiments, the biomarker is the number of post-synaptic neurons and indicative of a subject's suitability to be treated with a therapeutic agent. In some embodiments, the biomarker is the number of post-synaptic neurons. In some embodiments, the biomarker is the number of post-synaptic puncta. In some embodiments, the number is the density. In some embodiments, post-synaptic puncta or neurons are determined by the presence of PSD95. In some embodiments, the biomarker is the density of post-synaptic neurons. In some embodiments, the biomarker is the density of post-synaptic puncta. In some embodiments, the biomarker is the number of post-synaptic puncta per micrometer after treatment. In some embodiments, the biomarker is the distance between post-synaptic puncta. In some embodiments, the biomarker is the distance between post-synaptic puncta after treatment. In some embodiments, a number of post-synaptic puncta per micrometer above a predetermined threshold is indicative of suitability to be treated. In some embodiments, distance between post-synaptic puncta below a predetermined threshold is indicative of suitability to be treated. In some embodiments, density of post-synaptic puncta above a predetermined threshold is indicative of suitability to be treated. In some embodiments, an increase in the number of post-synaptic puncta per micrometer after treatment is indicative of suitability to be treated. In some embodiments, a decrease in the distance between post-synaptic puncta is indicative of suitability to be treated. In some embodiments, a number of post-synaptic puncta above a predetermined threshold is indicative of suitability to be treated. In some embodiments, an increase in the number of post-synaptic puncta after treatment is indicative of suitability to be treated. In some embodiments, density or post-synaptic puncta is indicative of suitability to be treated by an antidepressant. In some embodiments, density or post-synaptic puncta is indicative of suitability to be treated by Bupropion. In some embodiments, density or post-synaptic puncta is indicative of suitability to be treated by Nortriptyline. In some embodiments, density or post-synaptic puncta is indicative of suitability to be treated by an antidepressant selected from Bupropion and Nortriptyline. In some embodiments, density or post-synaptic puncta is indicative of suitability to be treated by a NDRI. In some embodiments, density or post-synaptic puncta is indicative of suitability to be treated by a tricyclic antidepressant.

In some embodiments, the biomarker is a change in a pre-synaptic marker and indicative of a subject's suitability to be treated with a therapeutic agent. In some embodiments, the biomarker is the number of pre-synaptic marker positive puncta and indicative of a subject's suitability to be treated with a therapeutic agent. In some embodiments, the pre-synaptic marker is synapsin. In some embodiments, the biomarker is the number of pre-synaptic neurons and indicative of a subject's suitability to be treated with a therapeutic agent. In some embodiments, the biomarker is the number of pre-synaptic neurons. In some embodiments, the biomarker is the number of pre-synaptic puncta. In some embodiments, pre-synaptic puncta or neurons are determined by the presence of synapsin. In some embodiments, the biomarker is the density of pre-synaptic neurons. In some embodiments, the biomarker is the density of pos-synaptic puncta. In some embodiments, the biomarker is the number of pre-synaptic puncta per micrometer after treatment. In some embodiments, a number of pre-synaptic puncta per micrometer above a predetermined threshold is indicative of suitability to be treated. In some embodiments, a number of pre-synaptic puncta per micrometer at baseline above a predetermined threshold is indicative of suitability to be treated. In some embodiments, a number of pre-synaptic puncta per micrometer after treatment above a predetermined threshold is indicative of suitability to be treated. In some embodiments, an increase in the number of pre-synaptic puncta per micrometer after treatment is indicative of suitability to be treated. In some embodiments, a number of pre-synaptic puncta above a predetermined threshold is indicative of suitability to be treated. In some embodiments, a number of pre-synaptic puncta at baseline above a predetermined threshold is indicative of suitability to be treated. In some embodiments, a number of pre-synaptic puncta after treatment above a predetermined threshold is indicative of suitability to be treated. In some embodiments, an increase in the number of pre-synaptic puncta after treatment is indicative of suitability to be treated. In some embodiments, the pre-synaptic marker is indicative of suitability to be treated by Bupropion. In some embodiments, the pre-synaptic marker is indicative of suitability to be treated by and NDRI.

In some embodiments, the biomarker is a number of intact synapses. In some embodiments, the biomarker is a number of puncta with colocalization of pre- and post-synaptic neurons. In some embodiments, the biomarker is a number of puncta with colocalization of pre- and post-synaptic markers. In some embodiments, the biomarker is the density of puncta with colocalization of pre- and post-synaptic markers. In some embodiments, a number of puncta with colocalization of pre- and post-synaptic marker at baseline is indicative of suitability to be treated. In some embodiments, a number of puncta with colocalization of pre- and post-synaptic markers after treatment is indicative of suitability to be treated. In some embodiments, a number of puncta with colocalization of pre- and post-synaptic markers above a predetermined threshold is indicative of suitability to be treated. In some embodiments, a number of puncta with colocalization of pre- and post-synaptic markers after treatment above a predetermined threshold is indicative of suitability to be treated. In some embodiments, an increase in the number of puncta with colocalization of pre- and post-synaptic markers is indicative of suitability to be treated. In some embodiments, an increase in the number of puncta with colocalization of pre- and post-synaptic markers after treatment is indicative of suitability to be treated. In some embodiments, an increase in the number of puncta with colocalization of pre- and post-synaptic markers by more than a predetermined threshold is indicative of suitability to be treated. In some embodiments, an increase in the number of puncta with colocalization of pre- and post-synaptic markers by more than a predetermined threshold after treatment is indicative of suitability to be treated. In some embodiments, colocalization of pre- and post-synaptic marker is indicative of suitability to be treated by Bupropion. In some embodiments, colocalization of pre- and post-synaptic marker is indicative of suitability to be treated by an NDRI. In some embodiments, colocalization of pre- and post-synaptic marker is indicative of suitability to be treated by Nortriptyline. In some embodiments, colocalization of pre- and post-synaptic marker is indicative of suitability to be treated by a tricyclic antidepressant.

In some embodiments, the biomarker is dendritic arborization. In some embodiments, dendritic arborization comprises dendritic branching. In some embodiments, the biomarker is dendritic branching. In some embodiments, dendritic arborization comprises dendrite length. In some embodiments, dendrite length is average dendrite length. In some embodiments, dendritic arborization comprises dendritic spine length. In some embodiments, dendritic arborization comprises average dendritic spine length. In some embodiments, baseline dendritic length below a predetermined threshold indicates a subject is suitable for treatment. In some embodiments, dendritic length after treatment below a predetermined threshold is indicative of suitability to be treated. In some embodiments, a decrease in dendritic length after treatment is indicative of suitability to be treated.

In some embodiments, the biomarker is the length of a dendritic spine and indicates suitability of a subject to be treated with a therapeutic agent. In some embodiments, the biomarker is dendritic spine length. In some embodiments, a dendritic spine length at baseline below a predetermined threshold is indicative of suitability to be treated. In some embodiments, a dendritic spine length after treatment above a predetermined threshold is indicative of suitability to be treated. In some embodiments, an increase in dendritic spine length indicates a suitability to be treated. In some embodiments, an increase in dendritic spine length in a specific spine type indicates a suitability to be treated. In some embodiments, a decrease in dendritic spine length indicates an unsuitability to be treated. In some embodiments, the dendritic spine type is mushroom spines. In some embodiments, the dendritic spine type is stubby spines. In some embodiments, the dendritic spine type is filopodia spines. In some embodiments, the dendritic spine type is thin spines. In some embodiments, longer dendritic length of mushroom spines is indicative of suitability to be treated. In some embodiments, longer dendritic length of mushroom spines after treatment is indicative of suitability to be treated. In some embodiments, longer dendritic length of stubby spines is indicative of suitability to be treated. In some embodiments, longer dendritic length of stubby spines after treatment is indicative of suitability to be treated. In some embodiments, longer dendritic length of thin spines is indicative of suitability to be treated. In some embodiments, longer dendritic length of thin spines after treatment is indicative of suitability to be treated. In some embodiments, dendritic spine length is indicative of suitability to be treated by Bupropion. In some embodiments, dendritic spine length is indicative of suitability to be treated by and NDRI. In some embodiments, dendritic spine length is indicative of suitability to be treated by Nortriptyline. In some embodiments, dendritic spine length is indicative of suitability to be treated by a tricyclic antidepressant.

In some embodiments, the biomarker is a number of thin spines and indicates suitability of a subject to be treated with a therapeutic agent. In some embodiments, the biomarker is the density of thin spines and indicates suitability of a subject to be treated with a therapeutic agent. In some embodiments, the biomarker is the percentage of thin spines and indicates suitability of a subject to be treated with a therapeutic agent. In some embodiments, the biomarker is the percentage of all spines that are thin spines and indicates suitability of a subject to be treated with a therapeutic agent. In some embodiments, the biomarker is density of thin spines. In some embodiments, the biomarker is number of thin spines. In some embodiments, the biomarker is percentage of thin spines. In some embodiments, the biomarker is percentage of all spines that are thin spines. In some embodiments, a number of thin spines above a predetermined threshold indicates the subject is suitable for treatment. In some embodiments, a density of thin spines above a predetermined threshold indicates the subject is suitable for treatment. In some embodiments, a percentage of thin spines above a predetermined threshold indicates the subject is suitable for treatment. In some embodiments, a number of thin spines after treatment indicates the subject is suitable for treatment. In some embodiments, a density of thin spines after treatment indicates the subject is suitable for treatment. In some embodiments, a percentage of thin spines after treatment indicates the subject is suitable for treatment. In some embodiments, a number of thin spines after treatment above a predetermined threshold indicates the subject is suitable for treatment. In some embodiments, a density of thin spines after treatment above a predetermined threshold indicates the subject is suitable for treatment. In some embodiments, a percentage of thin spines after treatment above a predetermined threshold indicates the subject is suitable for treatment. In some embodiments, the abundance of thin spines is indicative of suitability to be treated by Nortriptyline. In some embodiments, the abundance of thin spines is indicative of suitability to be treated by a tricyclic antidepressant. In some embodiments, abundance is number present. In some embodiments, abundance is density. In some embodiments, abundance is percentage.

As used herein, the terms "downregulation" and "decrease" are synonymous and used interchangeably. As used herein, the terms "upregulation" and "increase" are synonymous and are used interchangeably. In some embodiments, the decrease or increase is a statistically significant decrease or increase. In some embodiments, the decrease or increase is a decrease or increase of at least a threshold amount. In some embodiments, the statistically significant increase/decrease and/or the threshold increase/decrease are determined by examining a panel of cells derived from known responders and non-responders to the therapeutic agent and determining the threshold value for a change in expression that is statistically significant. This type of statistical analysis is routine in the art and can be performed by a skilled artisan with access to RNA expression data from the samples.

In some embodiments, the predetermined threshold is a statistically significant threshold. In some embodiments, the threshold is an expression level that correctly identifies subjects suitable for treatment. In some embodiments, correctly identifying comprises a correct identification of at least 60, 70, 75, 80, 85, 90, 95, 97, 99 or 100% of the subjects. Each possibility represents a separate embodiment of the invention. In some embodiments, correctly identifying comprises a false positive rate of at most 30, 25, 20, 15, 10, 7, 5, 3, 2, 1 or 0%. Each possibility represents a separate embodiment of the invention.

In some embodiments, the method further comprises providing a personalized treatment protocol for the subject. In some embodiments, the personalized treatment protocol is provided for a subject based on the suitability of the subject to be treated with a therapeutic agent. In some embodiments, the personalized treatment protocol is based on biomarker detection. In some embodiments, the personalized treatment protocol is based on repeating a method of the invention with a second therapeutic agent. In some embodiments, the personalized treatment protocol is based on performance of the method of the invention with a plurality of therapeutic agents, wherein each agent is tested separately, or in combination. In some embodiments, at least 1, 2, 3, 4, 5, 6, 7, 8, 9, or 10 therapeutic agents are tested by a method of the invention. Each possibility represents a separate embodiment of the invention. The term "protocol" as used herein refers to a detailed treatment plan. In some embodiments, the personalized treatment protocol is based on a ranking of the effectiveness of various therapeutic agents. In some embodiments, the treatment plan is an order in which each therapeutic agent should be tried.

In some embodiments, a therapeutic agent is administered to a subject based on the suitability of the subject to be treated with the therapeutic agent. In some embodiments, the method further comprises administering the therapeutic agent to a suitable subject. In some embodiments, the method further comprises not administering the therapeutic agent to an unsuitable subject. In some embodiments, the method further comprises administering an alternative treatment to an unsuitable subject. In some embodiments, an alternative treatment is an alternative therapeutic. In some embodiments, an alternative therapeutic is a therapeutic with a different method of action from the tested therapeutic.

The term "administered", as used herein, refers to any method which, in sound medical practice, delivers a composition containing an active agent to a subject in such a manner as to provide a therapeutic effect. One aspect of the present subject matter provides for oral administration of a therapeutically effective amount of a composition of the present subject matter to a patient in need thereof. Other suitable routes of administration can include parenteral, subcutaneous, intravenous, intramuscular, or intraperitoneal. The dosage administered will be dependent upon the age, health, and weight of the recipient, kind of concurrent treatment, if any, frequency of treatment, and the nature of the effect desired. In some embodiments, administration is based on biomarker detection.

In some embodiments, data obtained from a neuronal cell is used alone to determine suitability of a subject to be treated with a therapeutic agent. In some embodiments, data obtained from a neuronal cell is combined with other data to determine suitability of a subject to be treated with a therapeutic agent. In some embodiments, the other data comprises the subject's clinical, genetic or biological background or a combination thereof.

In some embodiments, data obtained from a neuronal cell is used alone to provide a personalized treatment protocol. In some embodiments, data obtained from a neuronal cell is combined with other data to provide a personalized treatment protocol. In some embodiments, the other data comprises a subject's clinical, genetic or biological background or a combination thereof.

As used herein, the term "about" when combined with a value refers to plus and minus 10% of the reference value. For example, a length of about 1000 nanometers (nm) refers to a length of 1000 nm+−100 nm.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Various embodiments and aspects of the present invention as delineated hereinabove and as claimed in the claims section below find experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Buchwalow and Böcker "Immunohistochemistry: Basics and Methods"; (2010); Ausubel et al., "Current Protocols in Molecular Biology", John Wiley and Sons, Baltimore, Maryland (1989); "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; Lanza and Atala "Essentials of Stem Cell Biology Book", 3rd Edition (2014); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); "RNA-seq Data Analysis: A Practical Approach", Korpelainen et al., (2014); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Strategies for Protein Purification and Characterization—A Laboratory Course Manual" CSHL Press (1996); all of which are incorporated by reference. Other general references are provided throughout this document.

Materials and Methods

LCL maintenance and reprogramming into iPSCs—Lymphoblastoid cell lines (LCLs) obtained from patients were cultured in T25 cell culture flasks at 37° C., 5% CO2. Cells were maintained in LCL media composed of RPMI 1640 with fetal bovine serum (FBS) (10%), 1 mM L-glutamine, 50 U/ml penicillin and 50 μg/ml streptomycin. Cells were observed under a light microscope and passaged in accordance with the pH of the media (indicated by media color).

Patient iPSCs reprograming was carried out using the Cytotune 2.0 Sendai reprogramming kit according to the manual. On the day of transduction (day 0), cells were transferred to a 15 ml conical tube and an additional washing step was performed to collect remaining adherent cells. $2.5\times10^5$ cells were resuspended in 1 ml of LCL media containing the Sendai virus particles. Infected cells were then transferred to one well of a 12-well plate. The plate was spun at 1000 g for 90 minutes and then placed at 37° C., 5% CO2. After six hours, 1 ml of fresh LCL media was added to the well. At day 1, cells were collected and resuspended in fresh LCL media to remove remaining virus particles and transferred back to the 12-well plate. On day 3, cells were collected and resuspended in LCL and ReproTeSR media (1:1, 2 ml total) and plated in a 6-well ESC-qualified Matrigel coated plate. The plate was spun down and placed at 37° C., 5% CO2. On day 4, 1 ml of ReproTeSR was added to the well. From day 5 to day 9, 75% of the media were replaced every other day by removing 1.5 ml of culture media and adding 1.5 ml of complete ReproTeSR media. Once small colonies emerged (days 9-12), media was changed daily with 1.5 ml of complete ReproTeSR media. Once colony confluency reached 25%, media was changed to mTeSR1 and from thereon changed daily.

PBMC isolation and reprogramming into iPSCs—EDTA-coated tubes containing 4.5 mL of patient blood were used to isolate PBMCs. Briefly, blood was transferred to Uni-Sep+U04 tubes and centrifuged for 20 minutes at 1000 g. The lymphocyte interface was collected and transferred into a sterile 15 mL conical centrifuge tube, and volume was brought to 13 mL by adding sterile PBS. Cells were centrifuged for 15 minutes at 250 g and resuspended in 1 mL of sterile PBS to perform cell count. Cells were spun down again and resuspended in 2 mL of expansion medium (QBSF-60 with the addition of 100 μg/ml Primocin; 50 U/ml penicillin; 50 μg/ml streptomycin; ascorbic acid 50 μg/mL; SCF 50 ng/mL; IL-3 10 ng/mL; EPO 2 U/mL; IGF-1 40 ng/mL; Dexamethasone 1 μM) and transferred to 1 well of a 12 well dish, incubated overnight at 37° C., 5% CO2. Remaining cells were centrifuged at 300 g for 10 minutes and frozen 1-2x10^6 cells/vial in freezing medium containing 90% FBS and 10% DMSO.

Six days prior to infection using Sendai virus, Primocin was removed from the culture media. Media from three days before infection was tested for *mycoplasma*. On the day of transduction (day 0), cells were transferred to a 15 ml conical tube and an additional washing step was performed to collect remaining adherent cells. Cells were counted and $2.5\times10^5$ were resuspended in 1 ml of expansion media (without Primocin), containing 10 μl of each of the Sendai virus particles. Infected cells were then transferred to one well of a 12-well plate. The plate was centrifuged at 1300 g for 90 minutes and then placed at 37° C., 5% CO2. After 6-8 hours, 1 ml of expansion medium was added to the well, and the cells were incubated overnight at 37° C., 5% CO2. On day 1, cells were collected and resuspended in fresh expansion medium to remove remaining virus particles and transferred back to a 12-well plate.

Two days following induction (day 3), cells were collected and resuspended in in expansion media and ReproTeSR media (1:1, 2 ml total) and plated in a 6-well plate coated with ESC-qualified Matrigel. Plates were spun down and placed back at 37° C., 5% CO2. On day 4, 1 ml of ReproTeSR was added to the cells. From day 5 to day 9, 75% of the media were replaced every other day by removing 1.5 ml of culture media and adding 1.5 ml of complete ReproTeSR media. Once small colonies emerged (day 9-12), 2 ml of complete ReproTeSR media was replaced daily. Once colony confluency reached 25%, culture media was replaced daily with complete mTesR1 media supplemented with 50 U/ml penicillin and 50 μg/ml streptomycin.

iPSC maintenance—iPSCs were plated in an ESC-qualified Matrigel coated 6-well plate or 10 $cm^2$ dish. For cell passaging, all reagents were prewarmed, media was removed from iPSCs, cells were rinsed once with PBS and incubated 3-4 minutes at 37° C. with Accutase. Colony detachment was verified under the microscope. DMEM was gently added to the well and cells were resuspended in the required volume of compete mTesR1. Once a confluency of 70%-80% was reached, cells were passaged at a ratio of 1:6 to 1:10.

iPSC differentiation into neurons—iPSCs were seeded at a density of $3\times10^6$ cells/well on a hESC-qualified Matrigel pre-coated 6-well plate and incubated at 37° C., 5% CO2 overnight. Differentiation was initiated the following day (day 0) after verifying that 100% confluency was reached. Differentiation media was added daily according to the following order: Q1 (day 0-1), Q2 (day 2-3), Q3 (day 4-5), Q4 (day 6-7), Q5 (day 8), Q6 (day 9,11,13), Q7 (day 15 onward) similar to a previously published protocol developed by for rapid differentiation to cortical neurons. The components of the described media, Q1-7, are provided in Appendix 1. Cells were assessed for differentiation efficiency and cell death on a daily basis. On day 9, differentiated neurons were re-plated on either 96-well plates (destined for staining) or 12-well plates (destined for RNA extraction) that were coated with 15 μg/mL Poly-ornithine diluted in PBS (overnight incubation at 37° C.), followed by 1 μg/mL Laminin and 2 μg/mL Fibronectin diluted in PBS (overnight incubation at 37° C.): Neurons were first rinsed with pre-warmed PBS and 1 ml/well of Accutase was added for 35 minutes at 37° C., 5% CO2. DNAseI (0.5 mg/mL) was then added for 10 additional minutes. 3 ml of pre-warmed Neurobasal media was added to each well and neurons were gently collected using a 5 ml stripette. Wells were then verified for the presence of any remaining neurons. Neurons were spun down and resuspended in Q6 media. Neurons were seeded at a density of 150,000 cells/$cm^2$ placed back at 37° C. Following four hours of incubation, media was changed to Q6 media (150 μl per 96-well and 1 ml per 12-well). Principle component analysis shows these iPSC-derived cortical neurons cluster together with other iPSC-derived cortical neurons and separately from undifferentiated iPSCs (FIG. 1).

Drug testing—Neurons were treated with either Bupropion (10 Citalopram (10 Mirtazapine (5 μM) or Nortriptyline (5 μM) (antidepressant drugs) at day 28 and day 32 following differentiation or with Q7 media without any drug as a control.

Cell staining and imaging analysis—Neurons were fixed with 4% paraformaldehyde solution at day 35. Following fixation, antigen blocking and cell permeabilization were performed using 10% horse serum, 0.2% Triton X-10 and 0.5% bovine serum albumin (BSA) in PBS for 15 minutes at room temperature. Primary antibodies were incubated in the above-described blocking solution for one hour at room temperature. For dendritic arborization analysis, pre/post-synaptic markers and colocalization analysis; α-Syn, PSD95 and MAP2 primary antibodies were used. Following washes, fluorophore-coupled secondary antibodies were incubated in the blocking solution for 1 hour at room temperature. The cells were counter-stained with 4',6-diamidino-2-phenylindole (DAPI) for nuclei detection for 15 minutes at room temperature followed by washes with PBS. Imaging was performed using Nikon Spinning Disk Confocal microscope. For imaging of pre- and post-synaptic markers, images were acquired with a 100× objective in z-stacks. For dendritic arborization analysis, images were acquired with a 20× objective in z-stacks. For imaging of dendritic spines, during culture treatment described in materials and methods, cells were infected at Day 20 with human syn-GFP or mKate virus and stained for GFP or mKate. Cells were fixed as described at day 35 and stained with antibodies against GFP or mKate respectively. Images were acquired using the Nikon Confocal Alit with a 60× objective and a 2× digital zoom in z-stacks and using the Nikon spinning disk Microscope with a 100× objective in z-stacks. Neuronal and synaptic morphology was assessed using the Neurolucida software, pre- and post-synaptic marker analysis was performed using CellProfiler and total dendritic length was measured using Fiji software.

RNA extraction and sequencing analysis—Total RNA was extracted using either NucleoSpin RNA XS (Macherey-Nagel) kit or RNeasy Micro Kit (Qiagen), according to manufacturer's instructions. RNA sequencing libraries were prepared using KAPA Stranded mRNA-Seq Kit with Illumina Truseq adapters according to manufacturer's instructions and were sequenced on Illumina NextSeq 500 to generate 75 bp single-end reads. RNA-sequencing samples were aligned to the GRCh38 reference genome using STAR aligner. TMM normalization of RNA read counts and differential gene expression analysis were carried out using edgeR.

Example 1: Gene Expression is Significantly Different at Baseline Between Responder and Non-Responder Patients with Major Depression LCLs were obtained from each of 20 subjects with major depression, 8 of which were known responders to the depression drug Bupropion and 12 of which were known non-responders. Cells were reprogrammed into iPSCs, following which iPSCs were differentiated into frontal cortical neuronal cells (see Materials and Methods). This was confirmed by immunofluorescence staining for MAP2, BRN2 and TBR1. At 28 days post differentiation the induced neurons were treated with 10 μM Bupropion or with a vehicle control. Another dose of drug or control was also administered at day 32. At day 35 neurons were either fixed for histological examination or isolated for RNA extraction.

Total RNA extracted from neurons was used for next generation sequencing to generate a full transcriptome. Analysis of the RNA sequencing data of cells derived from responders as compared to non-responders who received only vehicle control showed highly significant differences in basal expression in these induced neurons. Out of over 60,000 genes probed, 169 genes were found to be significantly ($p<0.01$) upregulated in responders at baseline. These genes are presented in Table 1. Many other genes were also found to be upregulated although not significantly so, some of which are presented in the table. Of the genes probed, 133 were found to be significantly (p<0.01) downregulated in responders at baseline. These genes are presented in Table 2. Many other genes were also found to be downregulated although not significantly so, some of which are presented in the table. Genes with statistically significant differences in expression are summarized in Tables 1 and 2. These genes represent markers of responders and non-responders at baseline.

TABLE 1

Upregulated genes in Bupropion responders at baseline.

| gene_ID | logFC | PValue | gene_ID | logFC | PValue |
|---|---|---|---|---|---|
| NPY2R | 1.995838 | 1.52656E−05 | SFRP4 | 1.792496 | 0.005654653 |
| MMS22L | 0.681086 | 0.000176516 | ZNF347 | 0.384899 | 0.005880313 |
| CASP8AP2 | 0.493962 | 0.000340086 | CYP26A1 | 1.055481 | 0.00588195 |
| BRIP1 | 0.661394 | 0.000413568 | TRNT1 | 0.365285 | 0.005914443 |
| SIM1 | 2.065989 | 0.000445284 | PCDH19 | 0.926512 | 0.005915944 |
| DHFR | 0.689456 | 0.000513231 | WASF3 | 0.635662 | 0.00594432 |
| RBL1 | 0.484263 | 0.000925031 | ATAD2 | 0.372513 | 0.006160969 |
| MGAM | 1.884353 | 0.001094355 | C5orf34 | 0.611699 | 0.006222907 |
| WNT8B | 1.682629 | 0.001111733 | STK38L | 0.423183 | 0.0063231 |
| APAF1 | 0.336171 | 0.001143757 | ME2 | 0.289485 | 0.006325581 |
| MAP2K6 | 0.663809 | 0.001212566 | MELK | 0.445136 | 0.006370098 |
| BLM | 0.635229 | 0.001400454 | PDS5A | 0.288463 | 0.006553422 |
| LBR | 0.451466 | 0.00140348 | CENPF | 0.572189 | 0.006619477 |
| CALCR | 2.091052 | 0.001428212 | CDC7 | 0.577187 | 0.006645563 |
| ZWILCH | 0.480205 | 0.001457904 | COMMD2 | 0.260433 | 0.006663273 |
| LONRF3 | 0.580532 | 0.001555861 | PCNA | 0.409138 | 0.006698332 |
| CIP2A | 0.562719 | 0.001598462 | MTBP | 0.508434 | 0.006711937 |
| SMC2 | 0.405727 | 0.001611163 | ZMYM4 | 0.279315 | 0.006752204 |
| C4orf46 | 0.455222 | 0.001621566 | SPIN4 | 0.439381 | 0.006800683 |
| DLX2 | 1.113071 | 0.001659403 | TAF1A | 0.466972 | 0.006805819 |
| EIF1AX | 0.651357 | 0.001663009 | MRPL19 | 0.363736 | 0.006934311 |
| LRRC40 | 0.456566 | 0.001694612 | BCLAF3 | 0.539191 | 0.006953095 |
| LRRC8B | 0.521235 | 0.001719881 | NUP107 | 0.405826 | 0.00697656 |
| MCM10 | 0.573876 | 0.001764044 | RNGTT | 0.35247 | 0.007022061 |
| TIGAR | 0.556292 | 0.001786788 | CBX5 | 0.388855 | 0.007053381 |
| ALG1O | 0.553978 | 0.001797418 | RBBP8 | 0.402077 | 0.007075463 |
| VGLL3 | 1.759455 | 0.001854376 | CNOT6 | 0.320512 | 0.007078378 |
| ZNF730 | 0.728922 | 0.001871277 | CDH6 | 0.862441 | 0.007182616 |
| SLC25A24 | 0.515229 | 0.001926499 | TOP2A | 0.472202 | 0.007196894 |
| RTKN2 | 0.682606 | 0.001978766 | SMC4 | 0.51077 | 0.007284407 |
| BUB3 | 0.345522 | 0.002019068 | EXOC5 | 0.413793 | 0.007339786 |
| DNA2 | 0.589803 | 0.002061882 | MCM4 | 0.528007 | 0.007439985 |
| TFAM | 0.512251 | 0.00215052 | PTPN13 | 0.569446 | 0.007560691 |
| PCLAF | 0.680874 | 0.002172839 | MAPK1IP1L | 0.265398 | 0.007616466 |
| TAF7L | 0.884174 | 0.002245966 | SUV39H2 | 0.405502 | 0.007617521 |
| OSBPL11 | 0.383581 | 0.002275044 | DMRTA1 | 0.760985 | 0.007672194 |
| GNB4 | 0.494974 | 0.002362252 | DSCC1 | 0.618761 | 0.007674819 |
| UTP2O | 0.410807 | 0.002552822 | ERCC8 | 0.318449 | 0.007734398 |
| MCM8 | 0.432117 | 0.002638137 | NDC1 | 0.469885 | 0.007791736 |
| ATAD5 | 0.563866 | 0.002648124 | ASPM | 0.568415 | 0.007836257 |
| EXO1 | 0.577471 | 0.002685861 | RADX | 0.601446 | 0.007974887 |
| CENPE | 0.63957 | 0.00274001 | LRRC3B | 1.136583 | 0.00797934 |
| NUCKS1 | 0.363432 | 0.002914464 | SELENOI | 0.424978 | 0.008020883 |
| FBXO5 | 0.493674 | 0.003037385 | NEIL3 | 0.575341 | 0.008102515 |
| SYCP2L | 0.700777 | 0.003063233 | FANCI | 0.49565 | 0.008102939 |
| NUP50 | 0.325618 | 0.003064573 | USP14 | 0.308774 | 0.008190665 |
| RASA2 | 0.420206 | 0.003089127 | TYW3 | 0.500797 | 0.00821329 |
| KNL1 | 0.540418 | 0.003176926 | C18orf54 | 0.625966 | 0.008240224 |
| SRSF1 | 0.525268 | 0.003236758 | FKBP5 | 0.437851 | 0.00826129 |
| SLC25A13 | 0.347075 | 0.003278079 | XRN2 | 0.262759 | 0.008339463 |
| **RIT2** | **1.948619** | **0.003289637** | MGA | 0.318189 | 0.008381778 |
| **FEZF1** | **1.943635** | **0.003418821** | FANCM | 0.437426 | 0.008508391 |
| KIF11 | 0.52952 | 0.003425333 | HELLS | 0.536587 | 0.008518593 |
| PRKDC | 0.464834 | 0.003611973 | ITGA6 | 0.514895 | 0.00880829 |
| CHEK1 | 0.533829 | 0.003677045 | NCAPG | 0.573337 | 0.008821852 |
| **DLX1** | **1.234215** | **0.003699948** | CNTNAP2 | 0.864305 | 0.008825823 |
| CENPI | 0.577782 | 0.003738625 | ZNF66 | 0.540488 | 0.008856771 |
| KIF18A | 0.595703 | 0.003746273 | XRCC2 | 0.569677 | 0.00890091 |
| NUP155 | 0.396587 | 0.003812628 | ANLN | 0.486805 | 0.008918978 |
| CHML | 0.553136 | 0.003825544 | C9orf40 | 0.365856 | 0.009007555 |
| HAUS6 | 0.559495 | 0.003830926 | NUDT21 | 0.361521 | 0.009009175 |
| TRA2B | 0.313036 | 0.003914129 | HNRNPA3 | 0.342399 | 0.009027638 |
| PHF6 | 0.542214 | 0.003947286 | ADAL | 0.347055 | 0.009100345 |
| QSER1 | 0.434118 | 0.004150753 | RBM12 | 0.286508 | 0.00915094 |
| ZNF678 | 0.572342 | 0.004168394 | H2AFV | 0.308806 | 0.009323169 |
| FAM135A | 0.452707 | 0.004276383 | CREB1 | 0.370078 | 0.009343782 |
| PDYN | 1.81834 | 0.004281207 | FXN | 0.367146 | 0.009397712 |
| EXOC6 | 0.471739 | 0.004304828 | ARHGAP11A | 0.483093 | 0.009404897 |
| VMA21 | 0.441177 | 0.004380791 | CDCA2 | 0.526297 | 0.009439655 |

TABLE 1-continued

Upregulated genes in Bupropion responders at baseline.

| gene_ID | logFC | PValue | gene_ID | logFC | PValue |
|---|---|---|---|---|---|
| CKAP2 | 0.492936 | 0.004411248 | NBN | 0.333027 | 0.009488942 |
| CENPQ | 0.549954 | 0.004525967 | TARDBP | 0.284115 | 0.009513136 |
| DEPDC1B | 0.607375 | 0.004605609 | SMARCAD1 | 0.380042 | 0.009591561 |
| **XKR9** | **1.473644** | **0.004633403** | BDP1 | 0.328376 | 0.009675219 |
| HOOK3 | 0.310552 | 0.004755552 | SRBD1 | 0.302954 | 0.009758778 |
| SNRNP48 | 0.444493 | 0.004766026 | PYGL | 0.85769036 | NS |
| TMPO | 0.352767 | 0.004819704 | DHRS2 | 3.27081644 | NS |
| LCLAT1 | 0.347385 | 0.004833136 | SLC25A15 | 0.6664626 | NS |
| VPS13A | 0.445948 | 0.004841943 | SERPINE1 | 2.01897547 | NS |
| RRM2 | 0.513488 | 0.004848611 | RAD51AP1 | 1.08543949 | NS |
| DTL | 0.548236 | 0.004929914 | GTF2H3 | 0.82279644 | NS |
| PAQR3 | 0.544012 | 0.004996283 | CRYZ | 1.04356265 | NS |
| TAF9B | 0.431903 | 0.005042849 | MSX2 | 1.68696916 | NS |
| CTDSPL2 | 0.407891 | 0.005056583 | STK26 | 1.07177897 | NS |
| ZNF260 | 0.37756 | 0.005149516 | KRT7 | 2.62944997 | NS |
| ZPLD1 | 1.60317 | 0.005162357 | CPM | 1.47046756 | NS |
| API5 | 0.361495 | 0.005209993 | ANKRD1 | 2.7118685 | NS |
| DCLRE1A | 0.374892 | 0.005240725 | HNMT | 1.87744597 | NS |
| ANGEL2 | 0.359571 | 0.005258733 | NOSTRIN | 1.16903244 | NS |
| MPHOSPH6 | 0.39729 | 0.005289907 | RPL22L1 | 1.14134565 | NS |
| PIGW | 0.521224 | 0.005393886 | WEE1 | 1.12963116 | NS |
| AGPS | 0.335345 | 0.005505614 | WNT10B | 1.72876765 | NS |
| FANCB | 0.669344 | 0.005600224 | CDK1 | 0.98505156 | NS |
| SIKE1 | 0.378579 | 0.005609341 | TGIF1 | 0.83714504 | NS |
| GPC3 | 1.125263 | 0.005620789 | RCSD1 | 1.83305443 | NS |
| LRRN3 | 0.894794 | 0.005630487 | | | |

NS = not significant.

TABLE 2

Downregulated genes in Bupropion responders at baseline.

| gene_ID | logFC | PValue | gene_ID | logFC | PValue |
|---|---|---|---|---|---|
| LIN37 | −0.83463527 | 1.58E−05 | PTPRH | −1.5981917 | NS |
| CYP27A1 | −0.971204861 | 9.35E−05 | KIF3C | −1.1176378 | NS |
| GSTT2B | −2.024592332 | 0.000101639 | GNAO1 | −1.0902439 | NS |
| DRGX | −3.408437847 | 0.000128748 | PHACTR3 | −1.3725486 | NS |
| SKOR2 | −2.915968608 | 0.000227078 | RPH3A | −1.8962702 | NS |
| COLEC11 | −1.409028354 | 0.000530139 | CHGB | −1.1964357 | NS |
| TRIM47 | −1.22555841 | 0.000558985 | PCBP4 | −1.383851 | NS |
| KIAA1211L | −0.987298171 | 0.00064873 | CABP7 | −1.6673275 | NS |
| COL8A2 | −2.851723005 | 0.000768596 | CHGA | −1.5257655 | NS |
| PHOX2B | −2.349239193 | 0.000774909 | CHRNA4 | −1.6950075 | NS |
| HSD3B7 | −0.633428235 | 0.000791337 | EEF1A2 | −1.7051081 | NS |
| SLPI | −1.949062461 | 0.000818838 | MAP1LC3A | −1.7684792 | NS |
| ADAMTSL2 | −1.82212044 | 0.001119049 | CELF4 | −1.6021634 | NS |
| GAA | −0.525996644 | 0.001129515 | SYP | −1.756952 | NS |
| CTSD | −0.616673022 | 0.001158912 | NDRG4 | −1.2132202 | NS |
| FTH1 | −0.479793154 | 0.001315809 | SMPD3 | −1.4053113 | NS |
| HS6ST1 | −0.578497676 | 0.001323203 | AP3B2 | −1.3037131 | NS |
| ALDOA | −0.997099516 | 0.001365832 | SCG3 | −1.1798938 | NS |
| TAF1C | −0.35186832 | 0.001417817 | STMN2 | −1.2112173 | NS |
| COL11A2 | −2.068331651 | 0.001539325 | OLFM2 | −1.0180329 | NS |
| NPR2 | −0.465370175 | 0.001617001 | SHD | −1.9163689 | NS |
| OGFR | −0.417692783 | 0.001629319 | ATP1A3 | −1.389564 | NS |
| CEMIP | −1.975237424 | 0.001687903 | MAST1 | −1.2330061 | NS |
| TNFRSF14 | −1.024745112 | 0.001689525 | RAB3A | −1.3330419 | NS |
| CXCL8 | −2.618826584 | 0.001728164 | TMEM176B | −1.7279671 | NS |
| **ELN** | **−2.198297007** | **0.001751291** | GCK | −1.9333876 | NS |
| PENK | −2.167380003 | 0.001839601 | CLIP2 | −0.9245722 | NS |
| IRF2BPL | −0.440591275 | 0.001983196 | LHX3 | −1.6952348 | NS |
| PSD4 | −0.926475022 | 0.001995875 | APBA1 | −1.5554321 | NS |
| USH1C | −2.145557527 | 0.002087568 | SPOCK2 | −1.8538553 | NS |
| SLC45A2 | −1.875601902 | 0.002116069 | RUNDC3A | −1.79638 | NS |
| RPS26 | −0.820487416 | 0.00218564 | SEPTIN4 | −1.8127917 | NS |
| JOSD2 | −0.876477381 | 0.002296952 | MYH3 | −4.0592617 | NS |
| NCMAP | −1.751696831 | 0.002520165 | PHACTR1 | −1.2779233 | NS |
| GATD3B | −1.078051119 | 0.002536152 | PCDHB6 | −1.3439441 | NS |
| PLEKHD1 | −2.895214129 | 0.002563536 | KIF21B | −1.155966 | NS |
| IL17RC | −0.636986661 | 0.00260942 | IQSEC3 | −1.5082125 | NS |
| PTGER4 | −1.037226809 | 0.002626726 | GDAP1L1 | −1.3726982 | NS |
| TOM1 | −0.42318917 | 0.002882473 | PCSK2 | −1.8429153 | NS |

TABLE 2-continued

Downregulated genes in Bupropion responders at baseline.

| gene_ID | logFC | PValue | gene_ID | logFC | PValue |
|---|---|---|---|---|---|
| GLIS2 | −0.56687813 | 0.002890718 | CDKN2D | −1.5106214 | NS |
| ZNF835 | −1.109540012 | 0.002899624 | CBFA2T3 | −1.1987412 | NS |
| EN2 | −2.610467429 | 0.002994558 | DPP6 | −1.1185239 | NS |
| PNPLA7 | −0.579207719 | 0.003152243 | HRC | −1.89314 | NS |
| ADAMTS15 | −1.656393037 | 0.003178426 | OLFM1 | −1.0532752 | NS |
| COL6A1 | −0.65136599 | 0.003187923 | C1QL1 | −2.214601 | NS |
| TSHZ3 | −0.935533971 | 0.003316015 | SNAP25 | −1.2601435 | NS |
| TULP1 | −1.393266661 | 0.003399395 | VSTM2L | −1.2584541 | NS |
| KCNF1 | −1.345221459 | 0.003426881 | GPR12 | −1.7131655 | NS |
| PI4KB | −0.307977086 | 0.00345173 | DUSP26 | −1.7559457 | NS |
| NTNG1 | −1.40768918 | 0.003612785 | CTIF | −0.8711746 | NS |
| PCSK9 | −1.59321973 | 0.003739483 | GSTM3 | −1.1354324 | NS |
| TYRP1 | −1.901415609 | 0.003739704 | FAIM2 | −1.928831 | NS |
| PRSS33 | −1.451823451 | 0.003872949 | STXBP1 | −1.0447548 | NS |
| JUNB | −0.693108732 | 0.003928882 | GABBR2 | −2.0991372 | NS |
| HOXB5 | −2.911870672 | 0.003982387 | HCRTR2 | −2.0802332 | NS |
| BDKRB2 | −1.34307208 | 0.004016778 | CHRNA1 | −2.5221499 | NS |
| F12 | −1.097727879 | 0.004072961 | PPFIA2 | −1.7067009 | NS |
| FRMPD1 | −1.716640156 | 0.004106561 | IGLON5 | −1.0660015 | NS |
| TLX3 | −1.416276829 | 0.004136719 | C1orf216 | −1.3032338 | NS |
| PADI2 | −1.365266243 | 0.004482951 | RXRG | −1.9541111 | NS |
| RARA | −0.551878023 | 0.004602085 | NYAP2 | −2.3508983 | NS |
| TBC1D10B | −0.420299005 | 0.00462224 | VWA5B2 | −1.2872069 | NS |
| STARD3 | −0.301518828 | 0.004647756 | GLRA1 | −2.0957278 | NS |
| NAGA | −0.38431277 | 0.004739005 | CPLX2 | −1.620614 | NS |
| SLC2A1 | −0.664039761 | 0.00474993 | FAM50B | −1.9907634 | NS |
| PIEZO2 | −2.289780723 | 0.004809842 | PSD2 | −1.390633 | NS |
| APOL2 | −0.620805009 | 0.004864544 | ZC3HAV1L | −2.0744465 | NS |
| PGPEP1 | −0.474829928 | 0.004870454 | SNTG1 | −1.6112363 | NS |
| COL9A2 | −1.337276252 | 0.005088692 | KLHL35 | −1.7221399 | NS |
| KCNA1 | −2.813897354 | 0.005131084 | NCAM1 | −1.1803345 | NS |
| ACAN | −2.649209077 | 0.005153574 | DRD2 | −1.6931075 | NS |
| TRAF1 | −0.681696872 | 0.005181532 | PLCH2 | −1.7970772 | NS |
| NNMT | −1.790536135 | 0.005230365 | KIRREL3 | −1.3705589 | NS |
| ZBTB4 | −0.288120165 | 0.005251277 | TLCD3B | −1.4720048 | NS |
| WBP2 | −0.352247729 | 0.005251429 | NRSN1 | −1.670967 | NS |
| FAM3A | −0.415658247 | 0.005281938 | PID1 | −1.2648796 | NS |
| EPHB3 | −0.603133323 | 0.005306825 | RAB6B | −1.1756552 | NS |
| LOX | −1.775805206 | 0.005491298 | GOLGA7B | −1.7182543 | NS |
| PGM1 | −0.539725651 | 0.005643454 | HK1 | −0.6144725 | NS |
| MAL | −1.29545847 | 0.005680127 | LRFN2 | −1.8437396 | NS |
| ZSWIM8 | −0.351068672 | 0.005689666 | LHFPL4 | −1.3098641 | NS |
| PSMB10 | −0.654014034 | 0.005716891 | HTR5A | −2.9050766 | NS |
| PPP6R1 | −0.299393188 | 0.00592835 | GDPD5 | −1.2585563 | NS |
| TRIM8 | −0.337538901 | 0.005982688 | DMTN | −1.5878241 | NS |
| AIFM2 | −0.501076073 | 0.005985862 | CELF3 | −1.2731362 | NS |
| PIGS | −0.289191753 | 0.005996369 | FNDC5 | −1.1604994 | NS |
| FAM163B | −1.457953245 | 0.006055248 | SPTBN4 | −1.209669 | NS |
| SLC38A3 | −0.956348712 | 0.00613338 | CYGB | −2.1376574 | NS |
| CCER2 | −0.846589213 | 0.006192607 | GNG3 | −1.6634985 | NS |
| PLPP4 | −1.113587557 | 0.006344101 | CADM3 | −1.6923089 | NS |
| RABEP2 | −0.479699454 | 0.006358648 | IGSF8 | −0.9417186 | NS |
| LOXL1 | −0.79916752 | 0.006384898 | ANKRD30BL | −3.4924606 | NS |
| THBS2 | −1.447385506 | 0.00649616 | BSN | −1.4913216 | NS |
| DUSP1 | −0.516799871 | 0.006528923 | TMEM246 | −0.9880525 | NS |
| CCDC187 | −1.039317443 | 0.006714835 | RET | −1.4571604 | NS |
| P2RX2 | −1.409493893 | 0.006753338 | SCN3B | −1.4861381 | NS |
| NDRG1 | −0.803262468 | 0.006900161 | **MFAP4** | **−1.7103437** | **NS** |
| ITPRIP | −0.566053127 | 0.006933532 | CACNG2 | −1.5767711 | NS |
| ACOT1 | −1.230565556 | 0.006939079 | ELFN2 | −1.1072255 | NS |
| RARRES2 | −0.832241492 | 0.006977185 | NYAP1 | −1.1945135 | NS |
| SST | −1.422178723 | 0.007029788 | ISLR2 | −2.5179004 | NS |
| TMEM72 | −1.3948826 | 0.007080352 | RBFOX3 | −1.4904974 | NS |
| LIMS2 | −0.87341 | 0.007090177 | ATCAY | −0.9625278 | NS |
| PVALB | −0.962008548 | 0.007174661 | HID1 | −1.1249396 | NS |
| CHST8 | −1.173357371 | 0.007554824 | NSG1 | −1.4918865 | NS |
| NDUFA4L2 | −1.176572559 | 0.007677006 | CPLX1 | −1.607027 | NS |
| YIPF3 | −0.339893332 | 0.007708159 | B3GALNT1 | −1.7622438 | NS |
| YPEL3 | −0.556901104 | 0.007881535 | NSG2 | −1.6861637 | NS |
| ISL2 | −1.708645793 | 0.008040611 | ADRA1B | −2.1814736 | NS |
| FZD9 | −1.418778505 | 0.008088576 | VSTM2A | −1.841389 | NS |
| RPRM | −0.820068968 | 0.008096222 | ZNF439 | −1.6801973 | NS |
| CXCL6 | −2.447734288 | 0.008184286 | TPPP | −1.1273995 | NS |
| GRAMD1A | −0.35096488 | 0.008191444 | CDK5R2 | −1.6968922 | NS |
| PPM1M | −0.524914114 | 0.008193112 | ARPP21 | −3.2516561 | NS |
| PDZRN3 | −0.480782245 | 0.008198389 | ABLIM3 | −1.8254536 | NS |

TABLE 2-continued

Downregulated genes in Bupropion responders at baseline.

| gene_ID | logFC | PValue | gene_ID | logFC | PValue |
|---|---|---|---|---|---|
| NTNG2 | −0.897996446 | 0.008326572 | SNCG | −1.8080526 | NS |
| SSH3 | −0.636209633 | 0.008552645 | GALNTL6 | −1.714333 | NS |
| ABCD1 | −0.511066303 | 0.008609674 | DES | −4.1259035 | NS |
| PRCD | −1.172421225 | 0.008620304 | CHST1 | −1.7885106 | NS |
| WFIKKN2 | −1.617608628 | 0.008726938 | DIRAS1 | −1.5752376 | NS |
| C1R | −1.225330723 | 0.00873127 | GRIN1 | −1.777319 | NS |
| FGF1O | −1.948427447 | 0.008736542 | ZDHHC22 | −1.4682857 | NS |
| NKX3-2 | −1.576848249 | 0.008796786 | NHLH2 | −2.2409746 | NS |
| FSTL3 | −0.595619533 | 0.008837764 | SRRM3 | −1.3468336 | NS |
| C9orf24 | −1.771428956 | 0.008949724 | TMEM151B | −1.401715 | NS |
| HOXB6 | −2.878981331 | 0.00903666 | TSPYL5 | −1.6544731 | NS |
| FBLN1 | −0.880323853 | 0.009060196 | KCNIP1 | −1.628142 | NS |
| COL5A3 | −1.323220098 | 0.009193021 | NXPH4 | −1.9342798 | NS |
| C1S | −1.470993883 | 0.0095732 | PNMA3 | −1.2828749 | NS |
| NCOR2 | −0.390481081 | 0.009734474 | CNTN2 | −2.3193604 | NS |
| TMEM175 | −0.45545138 | 0.009773178 | DUSP8 | −1.1894592 | NS |
| C20orf85 | −2.117856532 | 0.009820937 | SEPTIN5 | −1.7582018 | NS |
| AVIL | −1.398189948 | 0.009828089 | ROBO2 | −1.2128547 | NS |
| TMEM176A | −1.7183722 | NS | SLC24A3 | −1.5608084 | NS |
| MPO | −2.7360823 | NS | C11orf87 | −2.3108183 | NS |
| SYN1 | −1.4929341 | NS | MAPT | −1.7790856 | NS |
| MAPK8IP2 | −1.4060605 | NS | PCDHB13 | −1.1099582 | NS |
| DPF1 | −1.2308988 | NS | C11orf96 | −2.1980324 | NS |
| SYT7 | −1.5304708 | NS | PRKAR1B | −1.4683284 | NS |
| STMN4 | −1.4987267 | NS | INSYN2A | −1.6273084 | NS |
| ANK1 | −1.6466189 | NS | MYT1 | −1.2408215 | NS |
| DKK3 | −1.1828996 | NS | ELAVL3 | −1.3033335 | NS |
| PTPRN | −1.2574406 | NS | SLC6A17 | −2.2689528 | NS |
| F7 | −1.5216312 | NS | MYH6 | −4.3461579 | NS |
| PSD | −1.204125 | NS | RPS6KL1 | −1.0354232 | NS |
| **EYA2** | **−1.6104164** | **NS** | CACNA1E | −1.61821 | NS |
| SNAP91 | −1.3029427 | NS | GRIN3A | −1.8987633 | NS |
| CACNB1 | −1.1881595 | NS | RUSC2 | −1.03533 | NS |
| PPP2R5B | −1.1406622 | NS | L1CAM | −1.10693 | NS |
| EPHA8 | −1.5965835 | NS | TCEAL6 | −2.1466109 | NS |
| ASIC4 | −1.6973721 | NS | DPF3 | −1.2434603 | NS |
| SIDT1 | −2.3564621 | NS | VAMP2 | −0.7802821 | NS |
| FRY | −1.186502 | NS | PCDHGA3 | −2.6379574 | NS |
| SNCB | −1.7765496 | NS | XKR7 | −1.2249728 | NS |
| ACTL6B | −1.6962024 | NS | SCRT1 | −1.5018862 | NS |
| | | | MAGIX | −1.6761572 | NS |

NS = not significant.

Next, expression analysis was performed on the cells after they were treated with 10 μm Bupropion. Analysis of the RNA sequencing data of cells derived from responders as compared to non-responders who received Bupropion showed highly significant differences in gene expression in these treated induced neurons. Out of over 60,000 genes probed, 69 genes were found to be significantly ($p \leq 0.01$) upregulated in responders after treatment. These genes are presented in Table 3. Many other genes were also found to be upregulated although not significantly so, some of which are presented in the table. Of the genes probed, 174 were found to be significantly ($p \leq 0.01$) downregulated in responders at baseline. These genes are presented in Table 4. Many other genes were also found to be downregulated although not significantly so, some of which are presented in the table. Genes with statistically significant differences in expression are summarized in Tables 3 and 4. These genes represent markers of responders and non-responders after treatment.

TABLE 3

Upregulated genes in Bupropion responders after treatment.

| gene_ID | logFC | PValue | gene_ID | logFC | PValue |
|---|---|---|---|---|---|
| SLC25A13 | 0.328487 | 0.000586497 | FBXO5 | 0.75326911 | NS |
| SPIN4 | 0.483754 | 0.000691347 | TTK | 0.81998063 | NS |
| SLC25A17 | 0.361053 | 0.000772502 | MAN2A1 | 0.83161184 | NS |
| **SIM1** | **2.052485** | **0.000789115** | CENPA | 1.02464334 | NS |
| NPY2R | 1.653128 | 0.000854358 | EFHD1 | 0.87202765 | NS |
| ZC3H13 | 0.282723 | 0.001220654 | HDAC1 | 0.49909189 | NS |
| WNT8B | 1.790311 | 0.001572476 | CRYZ | 1.04356265 | NS |
| F8 | 0.460831 | 0.001587371 | PRDX6 | 0.58976106 | NS |
| TIGAR | 0.496516 | 0.00169901 | KIF14 | 0.7995344 | NS |
| DMRTA1 | 0.857991 | 0.001822604 | SPP1 | 1.21525164 | NS |
| ZWILCH | 0.416368 | 0.001845966 | FGF23 | 1.46791297 | NS |
| WNT10B | 1.076655 | 0.001884597 | CSF3R | 2.81007912 | NS |

TABLE 3-continued

Upregulated genes in Bupropion responders after treatment.

| gene_ID | logFC | PValue | gene_ID | logFC | PValue |
|---|---|---|---|---|---|
| GPC3 | 1.256885 | 0.001946855 | MSX2 | 1.68696916 | NS |
| ZBTB24 | 0.402098 | 0.002144186 | KIAA1217 | 0.88747054 | NS |
| NOS2 | 1.462099 | 0.002659987 | NPPB | 1.67114968 | NS |
| EIF1AX | 0.549336 | 0.002722522 | PLAU | 2.30172829 | NS |
| HLA-DMA | 0.918506 | 0.002791198 | ADGRE5 | 0.94316713 | NS |
| CHML | 0.488751 | 0.002967093 | STIL | 0.75901545 | NS |
| DHFR | 0.598669 | 0.003015659 | CKS2 | 0.77783248 | NS |
| OSBPL11 | 0.33936 | 0.003077115 | RREB1 | 0.51157019 | NS |
| MCUR1 | 0.242134 | 0.003611256 | RUNX2 | 0.89236652 | NS |
| CDH6 | 0.922417 | 0.003624102 | DLGAP5 | 0.83039071 | NS |
| TFAM | 0.458335 | 0.003747152 | CHTF18 | 0.43564921 | NS |
| SNRNP48 | 0.437122 | 0.003818734 | SEM1 | 0.50192287 | NS |
| MEIOC | 0.717225 | 0.003916453 | HAT1 | 0.75469537 | NS |
| BAG4 | 0.407105 | 0.004097541 | EGLN3 | 1.21552024 | NS |
| STK38L | 0.387022 | 0.004283219 | SGO1 | 0.82063995 | NS |
| HESX1 | 0.820718 | 0.004286599 | CNN1 | 0.87961344 | NS |
| LRRC8B | 0.422296 | 0.004477538 | EDA2R | 0.56900852 | NS |
| MGA | 0.306367 | 0.004669531 | TOP2A | 0.72009742 | NS |
| FREM2 | 0.865016 | 0.004862781 | MATN3 | 0.96178082 | NS |
| SFRP4 | 1.737285 | 0.005101803 | AP3B1 | 0.76139436 | NS |
| TSGA10IP | 0.859501 | 0.005151484 | TMTC1 | 1.15551464 | NS |
| MDN1 | 0.416677 | 0.005175817 | SWAP70 | 0.88688637 | NS |
| MCM4 | 0.529459 | 0.005611791 | NGF | 0.79280535 | NS |
| CCDC150 | 0.604222 | 0.005635164 | LRP4 | 1.05074262 | NS |
| HAUS6 | 0.50253 | 0.00566251 | STK26 | 1.07177897 | NS |
| TNFRSF13C | 0.521823 | 0.005665523 | SPOCD1 | 1.3304662 | NS |
| PPAT | 0.466864 | 0.005870069 | DSG3 | 2.29715419 | NS |
| SLC7A11 | 0.607471 | 0.006087571 | EPHA7 | 1.59182623 | NS |
| ARHGEF26 | 0.46329 | 0.006249295 | MDM2 | 0.67882914 | NS |
| S100A13 | 0.740446 | 0.006298311 | LAMC1 | 0.8643569 | NS |
| FBXO22 | 0.295676 | 0.006321152 | KIF23 | 0.71142018 | NS |
| SIKE1 | 0.301346 | 0.006499152 | KIF11 | 0.78631555 | NS |
| ANKRD27 | 0.303528 | 0.006758856 | KIF20B | 0.82510335 | NS |
| NFKBID | 0.445229 | 0.006794013 | ZGRF1 | 0.91205604 | NS |
| RNGTT | 0.311446 | 0.00690078 | DUSP6 | 0.92894993 | NS |
| POU5F1B | 0.972857 | 0.006908381 | DIAPH3 | 0.93625213 | NS |
| PRKDC | 0.396303 | 0.006929424 | TPM1 | 0.78566491 | NS |
| MGME1 | 0.436793 | 0.006953317 | TAF4B | 0.95824208 | NS |
| TXNRD1 | 0.311193 | 0.007127612 | **SLC47A1** | **2.056315** | **NS** |
| SMG1 | 0.279569 | 0.00725679 | PADI1 | 0.9658985 | NS |
| **DLX2** | **0.941203** | **0.007633383** | KIF2C | 0.69888074 | NS |
| WWP1 | 0.307303 | 0.00763843 | CD53 | 1.71191534 | NS |
| SYCP2L | 0.59726 | 0.007642233 | NUF2 | 0.72142576 | NS |
| ZNF347 | 0.36476 | 0.007882897 | HHIPL2 | 1.36774443 | NS |
| PTPN13 | 0.564499 | 0.007887711 | CDCA7 | 0.94901185 | NS |
| PCGF5 | 0.605567 | 0.007990398 | LPP | 0.75209066 | NS |
| USP37 | 0.29381 | 0.008520966 | MUC4 | 0.87048984 | NS |
| LGI1 | 0.97929 | 0.008530127 | USP53 | 0.82619283 | NS |
| SIGLEC10 | 0.806722 | 0.008599058 | LIX1 | 1.55637169 | NS |
| PHF6 | 0.468553 | 0.008915326 | VWDE | 1.17642718 | NS |
| ITGA6 | 0.520803 | 0.008957409 | ANKRD1 | 2.7118685 | NS |
| SELENOI | 0.336032 | 0.009027208 | ESAM | 1.6884806 | NS |
| ATAD5 | 0.544224 | 0.009115714 | HNMT | 1.87744597 | NS |
| ADAL | 0.30072 | 0.009231976 | WWC2 | 0.70832299 | NS |
| MZT1 | 0.48869 | 0.009867732 | ARL11 | 0.81888843 | NS |
| DNA2 | 0.543113 | 0.009882605 | CENPH | 0.82777189 | NS |
| PAWR | 0.477084 | 0.00994623 | RBMS1 | 0.78606352 | NS |
| PLXND1 | 1.36202331 | NS | IMPACT | 0.73148226 | NS |
| TNFRSF12A | 0.74492192 | NS | EME1 | 0.7814274 | NS |
| MGST1 | 0.93543185 | NS | ADAMTSL3 | 1.41335686 | NS |
| ANLN | 0.91099883 | NS | WNT9B | 0.59722193 | NS |
| DEPDC1 | 1.00478145 | NS | NOSTRIN | 1.16903244 | NS |
| FAS | 1.07907428 | NS | RPL22L1 | 1.14134565 | NS |
| SPDL1 | 0.7492105 | NS | ADAMTS9 | 0.9659166 | NS |
| ZIC2 | 0.7767142 | NS | HMGB2 | 0.59533361 | NS |
| DSG2 | 0.74600678 | NS | MAD2L1 | 0.83734967 | NS |
| USP28 | 0.498871 | NS | ITGA2 | 0.682154 | NS |
| RRM2B | 0.78671495 | NS | ANKRD33B | 0.80157277 | NS |
| POLQ | 0.74942866 | NS | FNDC1 | 0.96665228 | NS |
| NDC1 | 0.81881027 | NS | CHMP4C | 0.67727315 | NS |
| **SLC2A3** | **1.3579057** | **NS** | MELK | 0.84902521 | NS |
| YBX3 | 0.51647494 | NS | WEE1 | 1.12963116 | NS |
| TM7SF3 | 0.56274321 | NS | C18orf54 | 0.73279735 | NS |
| TRAM2 | 0.54168147 | NS | NEMP1 | 0.79099196 | NS |
| **COL17A1** | **1.83236118** | **NS** | STX3 | 0.50170437 | NS |
| PRR11 | 0.60886648 | NS | INPP5D | 1.20760939 | NS |

TABLE 3-continued

| Upregulated genes in Bupropion responders after treatment. | | | | | |
|---|---|---|---|---|---|
| gene_ID | logFC | PValue | gene_ID | logFC | PValue |
| ARHGAP10 | 1.24009226 | NS | PGM2 | 0.87868371 | NS |
| HMMR | 0.99390237 | NS | BUB1 | 0.6383916 | NS |
| NUP37 | 0.75917948 | NS | MT1E | 0.1751245 | NS |
| SESN1 | 0.72377601 | NS | CDK1 | 0.98505156 | NS |
| NDC80 | 0.82905836 | NS | KRT8 | 1.26031426 | NS |
| XPO1 | 0.73960344 | NS | TRIAP1 | 0.73434124 | NS |
| BAX | 0.47735996 | NS | LRRC15 | 0.65322466 | NS |
| L2HGDH | 0.75419421 | NS | MTBP | 0.78033723 | NS |
| CDV3 | 0.74815665 | NS | FUT10 | 0.6404183 | NS |
| NLRP1 | 1.23505746 | NS | DCP2 | 0.77022064 | NS |
| ORC6 | 0.80188344 | NS | CKS1B | 0.58694387 | NS |
| DSP | 1.32742125 | NS | DAG1 | 0.53388713 | NS |
| PYGL | 0.85769036 | NS | TNFRSF10D | 0.84632703 | NS |
| GNPNAT1 | 1.05993861 | NS | UBE2C | 0.56922915 | NS |
| VRK1 | 0.72288129 | NS | **FOSL1** | **1.136922** | **NS** |
| DHRS2 | 3.27081644 | NS | NUPR1 | 1.74522868 | NS |
| **PROCR** | **1.39300542** | **NS** | FOXL1 | 1.19122894 | NS |
| AMMECR1 | 0.71730875 | NS | **TGIF1** | **0.83714504** | **NS** |
| PPP1R13L | 0.81594486 | NS | ANKRD18A | 1.15487234 | NS |
| TFPI2 | 1.36688703 | NS | S1PR5 | 1.90564207 | NS |
| DLX5 | 2.13818143 | NS | CHEK2 | 0.76686062 | NS |
| HIBADH | 0.57248539 | NS | IQGAP3 | 0.66916167 | NS |
| CPVL | 0.85550638 | NS | RPS27L | 0.7458729 | NS |
| SERPINE1 | 2.01897547 | NS | SEPTIN10 | 0.7235792 | NS |
| PTGR1 | 0.68236839 | NS | SELENOV | 0.81352637 | NS |
| DNMBP | 0.53228298 | NS | FAM72B | 0.93178787 | NS |
| ERLIN1 | 0.59453939 | NS | FAM72A | 1.12273269 | NS |
| DLX4 | 1.48514986 | NS | SFT2D1 | 0.64874827 | NS |
| PMP22 | 1.52531207 | NS | ARHGAP11A | 0.71205278 | NS |
| SEPSECS | 0.72537033 | NS | CENPW | 0.79560212 | NS |
| KRT18 | 1.59649956 | NS | MICB | 0.94739292 | NS |
| LTA4H | 0.649367 | NS | HACD2 | 0.83890933 | NS |
| ELK3 | 0.93775003 | NS | ARHGAP19 | 0.58645392 | NS |
| RAD51AP1 | 1.08543949 | NS | SLC22A31 | 0.96252658 | NS |
| GTF2H3 | 0.82279644 | NS | EXOC3L2 | 1.01166764 | NS |

NS = not significant.

TABLE 4

| Downregulated genes in Bupropion responders after treatment. | | | | | |
|---|---|---|---|---|---|
| gene_ID | logFC | PValue | gene_ID | logFC | PValue |
| MAFB | −0.573024624 | 1.55E−05 | CRB1 | −1.690572492 | NS |
| DRGX | −4.337217844 | 2.39E−05 | RAB33A | −1.510086828 | NS |
| ADAMTSL2 | −1.832914042 | 3.52E−05 | APC | −0.915993156 | NS |
| FRMPD1 | −2.303366026 | 6.85E−05 | DTX1 | −1.203941612 | NS |
| POU4F1 | −1.727870006 | 0.000108607 | ADGRB3 | −1.496091558 | NS |
| COL8A2 | −2.755469913 | 0.000167983 | AGAP2 | −1.343384599 | NS |
| INMT | −1.061092279 | 0.000169256 | FAIM2 | −1.922644531 | NS |
| CDKN1C | −0.621085667 | 0.000206971 | KIAA0513 | −1.005381985 | NS |
| NNMT | −2.325733973 | 0.000256804 | NACAD | −0.832880839 | NS |
| SKOR2 | −2.986384048 | 0.000304321 | ALPK3 | −1.224415382 | NS |
| NPR2 | −0.594235239 | 0.000307443 | SCN2A | −1.840548008 | NS |
| CXCL8 | −3.085581981 | 0.00031293 | SCN7A | −1.457197151 | NS |
| PSMB9 | −1.681718849 | 0.000316083 | BINI | −0.852234974 | NS |
| CEMIP | −2.321168022 | 0.000337422 | **GAD2** | **−1.45953518** | **NS** |
| KLHL35 | −1.143847463 | 0.000348702 | STXBP1 | −1.033129715 | NS |
| PSMB8 | −1.140228835 | 0.000367532 | GABBR2 | −2.25060374 | NS |
| PIRT | −3.199410827 | 0.000405385 | SIT1 | −1.926617403 | NS |
| TMEM176B | −1.184130098 | 0.000418984 | SLC22A23 | −1.147826638 | NS |
| VLDLR | −0.402359831 | 0.000491224 | TUBB2B | −0.758342411 | NS |
| INHBB | −1.747831536 | 0.000500595 | **ATAT1** | **−0.818850728** | **NS** |
| ACOT1 | −1.405501135 | 0.000507062 | **SLCO2B1** | **−1.491255084** | **NS** |
| COL15A1 | −2.223610628 | 0.000566553 | SLCO5A1 | −1.211388271 | NS |
| TNFRSF14 | −1.090829738 | 0.000566636 | ARHGAP20 | −2.009716649 | NS |
| TBC1D2 | −0.69583693 | 0.000808338 | PARP6 | −0.680981987 | NS |
| PENK | −1.976591936 | 0.000868734 | CYP1B1 | −1.631405254 | NS |
| TRAF1 | −0.927428011 | 0.000870565 | RBP4 | −2.210470015 | NS |
| APOL2 | −0.645243505 | 0.000934715 | CHRNA1 | −2.489690359 | NS |
| TRPV2 | −1.59437893 | 0.000937509 | PCDH10 | −1.014765311 | NS |
| ASPN | −3.694690477 | 0.000989483 | RASGEF1B | −1.168086421 | NS |
| FAM20C | −0.692284041 | 0.001032595 | SHISAL1 | −1.497514166 | NS |

TABLE 4-continued

Downregulated genes in Bupropion responders after treatment.

| gene_ID | logFC | PValue | gene_ID | logFC | PValue |
|---|---|---|---|---|---|
| BDKRB2 | −1.47467279 | 0.001038477 | CLSTN3 | −0.816085609 | NS |
| TLX3 | −1.593329615 | 0.001087314 | SLC38A4 | −1.272795254 | NS |
| TMEM176A | −1.203130073 | 0.00110869 | PPFIA2 | −1.898436727 | NS |
| CPNE5 | −0.937025977 | 0.001131093 | TMEM132B | −1.025425246 | NS |
| GALNT14 | −1.1521397 | 0.001198807 | FAM222A | −1.164083235 | NS |
| THBS2 | −1.69985117 | 0.001204372 | REM2 | −1.185707372 | NS |
| PLEKHD1 | −3.282551358 | 0.001236811 | NOVAI | −0.975434381 | NS |
| TSHZ3 | −1.108612518 | 0.001290682 | RTN1 | −1.455719155 | NS |
| **ELN** | **−2.048415618** | **0.001306528** | SYT16 | −1.633041244 | NS |
| PLCH2 | −1.05101995 | 0.001314959 | DISP2 | −1.757478091 | NS |
| NTNG2 | −1.160924768 | 0.001333939 | SCAPER | −0.760554685 | NS |
| KCNA1 | −3.416045615 | 0.001347562 | ST8SIA2 | −1.15337438 | NS |
| TAF1C | −0.387014397 | 0.001364985 | RHBDL3 | −1.324682508 | NS |
| LGALS3BP | −0.960224062 | 0.001644859 | RNF165 | −0.955580059 | NS |
| IRF2BPL | −0.383545779 | 0.001647165 | LMTK3 | −0.914808056 | NS |
| COLEC11 | −1.562748911 | 0.0017684 | EVI5L | −0.971363879 | NS |
| ADAMTS15 | −1.743150785 | 0.00179822 | IGLON5 | −0.986877017 | NS |
| ITPRIP | −0.593129692 | 0.001833687 | C1orf216 | −1.465209797 | NS |
| ADAMTSL1 | −1.460054226 | 0.001932053 | RXRG | −1.775889495 | NS |
| CABP7 | −1.060298022 | 0.001983788 | **NR1I3** | **−1.277961239** | **NS** |
| CACNA1H | −0.513673108 | 0.002004753 | ANKRD53 | −1.517417371 | NS |
| CPNE9 | −1.359718259 | 0.00200726 | THSD7B | −1.554746029 | NS |
| GFRA2 | −1.546459113 | 0.002024486 | SCN1A | −1.947325398 | NS |
| ABCC6 | −0.546072442 | 0.002145021 | NYAP2 | −2.578279522 | NS |
| FNDC5 | −0.700823467 | 0.002312173 | RETREG2 | −0.571689418 | NS |
| SLC2A1 | −0.636165972 | 0.002367374 | 38047 | −1.193046575 | NS |
| CCER2 | −0.843121253 | 0.002369173 | TAGLN3 | −1.002486385 | NS |
| CPA4 | −2.790519005 | 0.002376375 | VWA5B2 | −1.110864152 | NS |
| PIEZO2 | −2.463541027 | 0.002415317 | ANK2 | −0.959036182 | NS |
| PLD5 | −1.908740337 | 0.00246255 | RNF175 | −1.628175574 | NS |
| HS6ST1 | −0.626416788 | 0.002527506 | GLRA3 | −3.119369859 | NS |
| TMEM163 | −1.065020476 | 0.002590516 | PIK3R1 | −0.978260063 | NS |
| PSD4 | −0.723387548 | 0.002666339 | ARHGAP26 | −0.762877706 | NS |
| EYA2 | −0.955034377 | 0.002669894 | GLRA1 | −2.173897095 | NS |
| PADI2 | −1.485367768 | 0.002782759 | CPLX2 | −1.646733477 | NS |
| EGFLAM | −1.797587952 | 0.002791772 | GFOD1 | −1.120061506 | NS |
| C1S | −1.548496883 | 0.002832624 | PSD2 | −1.446549583 | NS |
| PALM | −0.581020971 | 0.002866432 | LRRTM2 | −1.58701254 | NS |
| FGF1 | −1.363959437 | 0.002927162 | TTBK1 | −1.373754659 | NS |
| PRSS33 | −1.593282101 | 0.002946276 | FAXC | −0.955630695 | NS |
| C1R | −1.320196358 | 0.003024875 | GABRR1 | −2.903633541 | NS |
| TLR6 | −1.137838194 | 0.003034909 | ZC3HAV1L | −2.185517813 | NS |
| PHOX2B | −2.192205799 | 0.003064021 | ARHGAP36 | −2.568525945 | NS |
| TLX1 | −2.76363854 | 0.003099829 | SNTG1 | −2.047719341 | NS |
| OPTN | −0.43999612 | 0.003101205 | PLPPR1 | −1.558878257 | NS |
| TAP1 | −0.836903464 | 0.003169967 | CACNA1B | −1.2529322 | NS |
| PTGER2 | −2.590492836 | 0.003177539 | RGR | −2.072269043 | NS |
| P4HA3 | −2.238550412 | 0.003237692 | INA | −1.425399176 | NS |
| PLAC9 | −1.585336087 | 0.003286224 | LRRC4C | −1.522783822 | NS |
| NFIX | −2.44573403 | 0.003354582 | NCAM1 | −1.369755694 | NS |
| TREM1 | −2.481175576 | 0.003363263 | DRD2 | −1.595450005 | NS |
| KCNJ5 | −1.027952732 | 0.003406744 | KIRREL3 | −1.338061923 | NS |
| COL6A1 | −0.563917613 | 0.003446868 | KIAA1755 | −1.808695628 | NS |
| ADAMTS8 | −1.65766048 | 0.003512201 | TLCD3B | −1.430675576 | NS |
| GLIS2 | −0.502534678 | 0.003609696 | PCDH15 | −1.629114283 | NS |
| HES6 | −1.039914764 | 0.003625369 | KLHL1 | −2.101834009 | NS |
| ALDOC | −0.663546782 | 0.003675199 | ADRA2A | −1.411163237 | NS |
| FMOD | −2.269364357 | 0.003756194 | GPR158 | −1.27007445 | NS |
| FBLN5 | −1.917772487 | 0.003925506 | THRB | −2.356877591 | NS |
| USP18 | −0.96589225 | 0.004000742 | ANK3 | −1.261605746 | NS |
| CHST8 | −1.473656388 | 0.004005855 | AKAP6 | −1.215479017 | NS |
| LRFN5 | −0.681563843 | 0.004122913 | NPAS3 | −1.401588088 | NS |
| LOX | −1.554766783 | 0.004172853 | VPS26B | −0.624476896 | NS |
| NKX3-2 | −1.634587622 | 0.004188875 | AKR1C2 | −1.477683615 | NS |
| USH1C | −1.857858794 | 0.004308534 | DPYSL4 | −1.082146772 | NS |
| ZNF575 | −0.869998847 | 0.004316746 | MFSD6 | −1.111879591 | NS |
| OPRK1 | −0.939006016 | 0.004337355 | SERP2 | −1.448912074 | NS |
| SECTM1 | −1.069869119 | 0.004443792 | TMEM132D | −1.359867541 | NS |
| SAMD9L | −1.953577928 | 0.004510947 | TMEM178A | −0.903968323 | NS |
| HCN1 | −2.181119125 | 0.004534901 | **RIT2** | **−2.318059955** | **NS** |
| CXCL6 | −2.411938234 | 0.00460025 | GRIA4 | −1.26297542 | NS |
| OPRM1 | −1.984706816 | 0.004674667 | IFIT5 | −0.821816133 | NS |
| TAP2 | −0.806837036 | 0.004722183 | PRDM8 | −2.418353564 | NS |
| ARHGEF28 | −0.915963889 | 0.004836125 | RAB3C | −1.236298239 | NS |
| GPBAR1 | −0.913069026 | 0.004939674 | STK32B | −1.643517084 | NS |
| IAH1 | −0.789040529 | 0.004967977 | NRSN1 | −1.718039941 | NS |

TABLE 4-continued

Downregulated genes in Bupropion responders after treatment.

| gene_ID | logFC | PValue | gene_ID | logFC | PValue |
|---|---|---|---|---|---|
| KHDC1 | −0.772420791 | 0.004985529 | JAKMIP1 | −1.737282869 | NS |
| PARP10 | −1.040961406 | 0.005013636 | LGI2 | −1.252576092 | NS |
| OLFML2B | −1.029959311 | 0.005039268 | PTPRR | −1.516869094 | NS |
| PODN | −1.120122201 | 0.00505786 | CMIP | −0.639084427 | NS |
| ARL17B | −1.231950372 | 0.005098155 | PID1 | −1.454771491 | NS |
| SYNC | −1.687667321 | 0.00513563 | LG14 | −0.984467947 | NS |
| PRPH | −2.032740671 | 0.005284955 | AK5 | −1.456171215 | NS |
| TRMT9B | −0.688829648 | 0.005366906 | ANKH | −0.926868755 | NS |
| KDM4B | −0.330993764 | 0.005368772 | CDH12 | −2.030448195 | NS |
| NDUFA4L2 | −0.837868013 | 0.005382771 | PITPNC1 | −0.829810573 | NS |
| CCDC183 | −0.528097958 | 0.005485907 | GPR26 | −2.221075482 | NS |
| RBP1 | −0.667570987 | 0.005514761 | NCAM2 | −1.14739491 | NS |
| PTGDS | −1.612431202 | 0.005544717 | RAB6B | −1.224872134 | NS |
| JOSD2 | −0.73769816 | 0.00557294 | CA10 | −2.575752641 | NS |
| AQP6 | −1.137166698 | 0.005619342 | PTPRN2 | −1.271563027 | NS |
| CXCL2 | −1.782811426 | 0.005707885 | GOLGA7B | −1.853930265 | NS |
| KIF26A | −0.513483997 | 0.005757223 | FMN2 | −1.148002424 | NS |
| C5orf63 | −1.210844529 | 0.005824737 | LSM11 | −0.728179952 | NS |
| CCDC187 | −1.023370696 | 0.005870079 | KIF5A | −1.285140029 | NS |
| EFEMP2 | −0.792873312 | 0.005888544 | TSPAN7 | −1.098074476 | NS |
| SUN2 | −0.452337569 | 0.00589147 | PPP2R2B | −1.116330875 | NS |
| SAMD9 | −1.373244724 | 0.006040705 | KCNS2 | −2.976246689 | NS |
| POLR2J3 | −0.756019192 | 0.0060949 | HK1 | −0.552801149 | NS |
| RAB42 | −0.509279467 | 0.00612535 | LRFN2 | −1.644530009 | NS |
| RBMS3 | −0.806510012 | 0.006194261 | LHFPL4 | −1.280343546 | NS |
| SST | −1.012460435 | 0.006214901 | NMNAT2 | −1.044108431 | NS |
| OGFR | −0.317950795 | 0.006310173 | HTR5A | −2.979555362 | NS |
| PRCD | −1.031673632 | 0.00633761 | KCNJ6 | −1.811246912 | NS |
| RPH3A | −2.056639896 | 0.00636063 | MX1 | −1.291319835 | NS |
| COL1A1 | −1.88035816 | 0.006513279 | MRAS | −0.569764555 | NS |
| IGFBP5 | −0.981410885 | 0.006569504 | GDPD5 | −1.244964327 | NS |
| HOXB5 | −2.738880562 | 0.00666893 | NPM2 | −1.674273327 | NS |
| TMC3 | −2.021086073 | 0.006804918 | FGF17 | −1.634787192 | NS |
| TF | −1.257356601 | 0.006895285 | DMTN | −1.522477593 | NS |
| MX2 | −1.617535809 | 0.006919571 | SV2A | −0.93412637 | NS |
| SH3TC2 | −1.43743859 | 0.007101561 | **CELF3** | **−1.259829309** | **NS** |
| LOXL1 | −0.623555046 | 0.007167666 | FAM131B | −0.896182798 | NS |
| OTOG | −1.855244844 | 0.007286077 | SLC37A1 | −1.051641027 | NS |
| MAB21L2 | −0.932913811 | 0.00729079 | GPSM1 | −0.732973313 | NS |
| SLC38A3 | −0.861261175 | 0.007299887 | SPTBN4 | −1.121819131 | NS |
| CD151 | −0.437659972 | 0.007445106 | BRSK1 | −0.753038603 | NS |
| MGP | −2.669798505 | 0.007481119 | CHRNB2 | −1.815061455 | NS |
| RSAD2 | −1.645645242 | 0.007500827 | CYGB | −1.896206832 | NS |
| PXDNL | −1.406115922 | 0.007514099 | ZNF385A | −0.879538418 | NS |
| DYRK1B | −0.398376549 | 0.007514132 | MPP3 | −1.028521674 | NS |
| MCC | −0.854824931 | 0.007527139 | SHANK1 | −1.29241419 | NS |
| MKX | −1.877935765 | 0.00762326 | TBC1D24 | −0.852665077 | NS |
| SUSD1 | −0.628996261 | 0.007680188 | GNG3 | −1.563310958 | NS |
| ADAMTS4 | −0.722972095 | 0.007766141 | ELAVL4 | −1.3261875 | NS |
| IL17RC | −0.533324362 | 0.007787886 | B3GALT2 | −1.68531254 | NS |
| ZFPM1 | −0.512684008 | 0.008042734 | NTNG1 | −1.192572963 | NS |
| EPHB3 | −0.495596069 | 0.008050054 | CADM3 | −1.659201615 | NS |
| SLC17A7 | −1.357798355 | 0.008463208 | KCNJ9 | −1.383387145 | NS |
| ISLR | −1.645900612 | 0.008656658 | IGSF8 | −0.661444077 | NS |
| LURAP1L | −1.086112724 | 0.00874452 | LRATD1 | −1.429072012 | NS |
| GAA | −0.485627813 | 0.008755046 | KCNJ3 | −1.979318224 | NS |
| HMX1 | −1.477835005 | 0.00876696 | FBXO41 | −0.970019217 | NS |
| DHRS3 | −1.126220703 | 0.008864175 | ANKRD30BL | −2.89697486 | NS |
| ARHGAP23 | −0.58905779 | 0.009014908 | SLC22A15 | −0.958868597 | NS |
| S100B | −1.743658806 | 0.009075659 | CCDC141 | −2.885795837 | NS |
| HS3ST2 | −1.227862292 | 0.009283316 | NFASC | −1.150383942 | NS |
| TRIM8 | −0.2802466 | 0.009319569 | CLASP2 | −0.753601826 | NS |
| VSTM2B | −1.078677419 | 0.009398834 | PPM1K | −0.707722765 | NS |
| SMPD1 | −0.583296872 | 0.009558124 | ABLIM2 | −1.304928839 | NS |
| SLC4A4 | −1.349852015 | 0.009680859 | BSN | −1.59894964 | NS |
| LYPD1 | −0.770299874 | 0.009841405 | WDR82 | −0.486156662 | NS |
| TMEM175 | −0.501561617 | 0.009911674 | ERAP2 | −2.320106379 | NS |
| PLPP4 | −0.998892523 | 0.009935781 | EBF1 | −1.335206766 | NS |
| HECW1 | −1.708649 | NS | **GRIK2** | **−1.099739217** | **NS** |
| DBNDD1 | −0.811722138 | NS | ANKRD55 | −1.878689551 | NS |
| MTMR7 | −1.10026502 | NS | ADCY1 | −1.308490266 | NS |
| SARM1 | −1.209289247 | NS | FAM219A | −0.850592406 | NS |
| ARHGAP33 | −0.950220692 | NS | DIRAS2 | −1.95215878 | NS |
| MPO | −2.162729959 | NS | TMEM246 | −1.159351809 | NS |
| CACNG3 | −1.336644466 | NS | WNK2 | −0.760837278 | NS |
| TAC1 | −1.10078422 | NS | PGM2L1 | −1.007813698 | NS |

TABLE 4-continued

| Downregulated genes in Bupropion responders after treatment. | | | | | |
|---|---|---|---|---|---|
| gene_ID | logFC | PValue | gene_ID | logFC | PValue |
| SYN1 | −1.542633621 | NS | PHYHIPL | −1.557976243 | NS |
| MAPK8IP2 | −1.460848486 | NS | RET | −1.421759508 | NS |
| RHOBTB2 | −0.731743121 | NS | IFI27 | −1.463073056 | NS |
| DPF1 | −1.340348407 | NS | KCNC2 | −2.212964388 | NS |
| SYT7 | −1.504775625 | NS | SCN3B | −1.721606417 | NS |
| SLC7A14 | −1.704824013 | NS | APBB1 | −0.819887962 | NS |
| STMN4 | −1.412870068 | NS | CHRFAM7A | −1.644507898 | NS |
| ISL1 | −2.074652904 | NS | TVP23A | −1.064279801 | NS |
| RUFY3 | −0.707189421 | NS | BMERB1 | −0.837315452 | NS |
| CNTN1 | −1.722361408 | NS | TERF2IP | −0.745470443 | NS |
| SYT13 | −1.443871576 | NS | CACNG2 | −1.666162171 | NS |
| INSRR | −1.555137638 | NS | ELFN2 | −1.112541388 | NS |
| ANK1 | −1.875441015 | NS | SCG5 | −1.072810725 | NS |
| LRRC7 | −1.643076748 | NS | NYAP1 | −0.984448671 | NS |
| ATP6V0A1 | −0.601179773 | NS | MAP1A | −1.103163518 | NS |
| TIMP2 | −0.878017617 | NS | MAPRE2 | −0.743185538 | NS |
| DKK3 | −1.052037792 | NS | SAMD14 | −1.111367153 | NS |
| SLC4A8 | −0.866775936 | NS | ISLR2 | −2.565034725 | NS |
| FSTL4 | −1.799941753 | NS | RBFOX3 | −1.57542596 | NS |
| PTPRN | −1.070700197 | NS | CACNB3 | −0.687826886 | NS |
| ATP9A | −1.421045511 | NS | ATCAY | −1.04722487 | NS |
| KCNH2 | −0.820983543 | NS | HID1 | −0.974952855 | NS |
| F7 | −1.608303299 | NS | CASKIN1 | −0.97812857 | NS |
| CAMK2B | −1.689089213 | NS | LGI3 | −2.434111193 | NS |
| PSD | −1.026530446 | NS | MYL1 | −4.411072154 | NS |
| LZTS1 | −1.331978185 | NS | NSG1 | −1.703972642 | NS |
| FAR2 | −1.383963078 | NS | FSTL5 | −1.624229385 | NS |
| SNAP91 | −1.604947609 | NS | CPLX1 | −1.466685199 | NS |
| CACNB1 | −1.260736456 | NS | VXN | −1.526909227 | NS |
| SYT1 | −1.058385474 | NS | CXCL11 | −2.54402559 | NS |
| ATP2B3 | −1.770749182 | NS | B3GALNT1 | −2.052116998 | NS |
| REEP1 | −1.550727539 | NS | GPRIN1 | −1.520923774 | NS |
| PPP2R5B | −1.051455139 | NS | SCN9A | −1.80303378 | NS |
| EPHA8 | −1.344953636 | NS | CTNND2 | −1.034139072 | NS |
| RPS6KA2 | −0.883051633 | NS | OTUD7A | −1.036396321 | NS |
| TRIB2 | −0.70771763 | NS | FRMPD4 | −2.129881586 | NS |
| ASIC4 | −1.719652267 | NS | NSG2 | −1.941611689 | NS |
| CRMP1 | −1.120796402 | NS | ADRA1B | −2.201790117 | NS |
| SIDTI | −2.102620607 | NS | DCLK2 | −1.476726455 | NS |
| CLCN4 | −0.816812318 | NS | VSTM2A | −1.971117166 | NS |
| FRY | −1.358591057 | NS | **MTSS1** | **−0.940594504** | **NS** |
| PPP2R2C | −1.734974459 | NS | TANC2 | −0.727779054 | NS |
| SNCB | −1.524121034 | NS | PKIA | −1.193918244 | NS |
| KCNQ2 | −1.052840498 | NS | ATP6V0E2 | −1.01131053 | NS |
| ADD2 | −0.795789573 | NS | ZNF439 | −2.200692988 | NS |
| KIFAP3 | −0.907098338 | NS | KCNK3 | −2.029993986 | NS |
| CAMSAP3 | −0.89317797 | NS | TPPP | −1.039724516 | NS |
| RAP1GAP | −0.71909464 | NS | CDK5R2 | −1.88099142 | NS |
| ACTL6B | −1.577300713 | NS | NHLH1 | −1.304646916 | NS |
| RBFOX1 | −1.575650673 | NS | FRMD5 | −0.787106902 | NS |
| ADCYAP1R1 | −1.153617915 | NS | SCG2 | −1.691014337 | NS |
| BRINP1 | −1.622823851 | NS | GAP43 | −1.304389799 | NS |
| TP53INP2 | −1.176876301 | NS | CALB2 | −1.647393106 | NS |
| RUNX1T1 | −1.916305695 | NS | **NEGR1** | **−1.829167126** | **NS** |
| RIMS1 | −1.830226932 | NS | RCAN2 | −1.601803802 | NS |
| PTPRH | −1.255007597 | NS | ARPP21 | −3.247478941 | NS |
| CDH7 | −1.610956284 | NS | ADCY5 | −1.298524909 | NS |
| SMAP2 | −0.819604847 | NS | ABLIM3 | −2.050378166 | NS |
| KIF3C | −1.294652944 | NS | SNCG | −1.395865965 | NS |
| WDR47 | −0.834302511 | NS | INSM1 | −1.182898397 | NS |
| PPEF1 | −1.590469301 | NS | KCNH6 | −1.966467576 | NS |
| GNAO1 | −1.181109578 | NS | NWD2 | −2.251073151 | NS |
| PHACTR3 | −1.43910966 | NS | GALNTL6 | −1.861468543 | NS |
| EPB41L1 | −0.913397561 | NS | SEZ6L2 | −0.776844639 | NS |
| PPP1R13B | −1.190875029 | NS | **DES** | **−2.4396046** | **NS** |
| CHGB | −1.245546314 | NS | CHST1 | −1.71140247 | NS |
| KCNH4 | −1.416882857 | NS | TP53I11 | −0.840746675 | NS |
| GMIP | −0.764952237 | NS | DPP10 | −1.13003611 | NS |
| NECAP1 | −0.604375648 | NS | TOM1L2 | −0.719871482 | NS |
| PCBP4 | −1.293165503 | NS | CREG2 | −1.282164896 | NS |
| PITPNM2 | −0.7259491 | NS | DIRAS1 | −1.659725116 | NS |
| RAPGEF4 | −1.421227958 | NS | KBTBD11 | −1.029509233 | NS |
| SLC17A6 | −2.069231474 | NS | RNF152 | −1.135332298 | NS |
| STX1B | −0.990723995 | NS | CDK5R1 | −1.375445609 | NS |
| CEP170B | −0.670263803 | NS | BASP1 | −0.860679113 | NS |
| MFNG | −1.262032661 | NS | WSB2 | −0.864444761 | NS |

TABLE 4-continued

| Downregulated genes in Bupropion responders after treatment. | | | | | |
|---|---|---|---|---|---|
| gene_ID | logFC | PValue | gene_ID | logFC | PValue |
| SEZ6L | −1.450319397 | NS | GRIN1 | −1.919282695 | NS |
| SEPTIN3 | −1.332531046 | NS | LY6H | −1.547495774 | NS |
| SYNGR1 | −0.827067413 | NS | DSCAML1 | −1.403743102 | NS |
| TRIM9 | −1.351773796 | NS | ZDHHC22 | −1.454985939 | NS |
| DAAM1 | −0.694496993 | NS | KCNA2 | −1.234832032 | NS |
| CHGA | −1.542750615 | NS | PPFIA3 | −0.735045291 | NS |
| SLC8A3 | −1.496484633 | NS | NAP1L5 | −0.871039853 | NS |
| DOK5 | −1.084709089 | NS | NHLH2 | −2.36269338 | NS |
| HRH3 | −1.315289377 | NS | SRRM3 | −1.175344129 | NS |
| NKAIN4 | −0.875279513 | NS | CCDC184 | −1.385199872 | NS |
| CHRNA4 | −1.718212208 | NS | ASB8 | −0.712735679 | NS |
| EEF1A2 | −1.422673834 | NS | AMER3 | −1.721654408 | NS |
| SNPH | −1.13422882 | NS | **TMEM151B** | **−1.463196557** | **NS** |
| PDYN | −1.612590436 | NS | SLITRK1 | −1.312114323 | NS |
| PAK5 | −1.628362311 | NS | CEP295NL | −1.321334342 | NS |
| MAP1LC3A | −1.5597872 | NS | TMEM151A | −1.522456782 | NS |
| CELF4 | −1.81241916 | NS | MKRN3 | −1.448120174 | NS |
| GLRA2 | −1.92947678 | NS | NRXN1 | −1.371980209 | NS |
| SYP | −1.709464287 | NS | TH | −1.664349021 | NS |
| PCSK1N | −1.45993447 | NS | GPR139 | −1.695141305 | NS |
| FGF14 | −1.149369293 | NS | TSPYL5 | −1.843324895 | NS |
| NDRG4 | −1.320062964 | NS | SSTR2 | −1.44861287 | NS |
| SMPD3 | −1.445342425 | NS | ZFP3 | −1.93279469 | NS |
| CORO2B | −1.199123995 | NS | CHRM2 | −2.119870567 | NS |
| HERC1 | −0.595273059 | NS | C4orf50 | −1.940117061 | NS |
| AP3B2 | −1.481706373 | NS | KCNIP1 | −1.501609458 | NS |
| SCG3 | −1.430909231 | NS | SHISAL2A | −1.160429027 | NS |
| EYA1 | −0.812826743 | NS | GABRG3 | −1.687088437 | NS |
| STMN2 | −1.405503934 | NS | NXPH4 | −1.744324618 | NS |
| OLFM2 | −1.001707202 | NS | MXRA7 | −0.642060701 | NS |
| APLP1 | −1.076437221 | NS | NTM | −1.350429874 | NS |
| ETFB | −1.045206161 | NS | GALNT9 | −1.689903613 | NS |
| ATP1A3 | −1.336189112 | NS | RGS7 | −1.689311635 | NS |
| PLPPR2 | −0.973986997 | NS | SPNS2 | −1.21106912 | NS |
| MAST1 | −1.275978069 | NS | CAMK1D | −0.951258548 | NS |
| RAB3A | −1.353761477 | NS | CSMD1 | −1.309908971 | NS |
| TMEM59L | −0.881860501 | NS | TMEM121B | −0.895751718 | NS |
| CADM4 | −0.674452998 | NS | TAFA1 | −2.192906556 | NS |
| RUNDC3B | −1.512387849 | NS | PNMA3 | −1.22134016 | NS |
| **GCK** | **−1.587356255** | **NS** | LRRC55 | −1.342107017 | NS |
| CLIP2 | −0.856032969 | NS | CLDN5 | −1.453094836 | NS |
| ELAVL2 | −0.918425018 | NS | CNTN2 | −2.494093051 | NS |
| NCS1 | −1.056483612 | NS | CEND1 | −1.294612595 | NS |
| APBA1 | −1.797324466 | NS | DUSP8 | −1.120482539 | NS |
| SH3GL2 | −1.666426184 | NS | SNN | −0.659110605 | NS |
| SPOCK2 | −2.031925514 | NS | RALYL | −2.285237366 | NS |
| DNAJC12 | −0.987401768 | NS | OSBP2 | −1.124845805 | NS |
| RUNDC3A | −1.678169516 | NS | ROBO2 | −1.39351866 | NS |
| SEPTIN4 | −1.512731787 | NS | SLC24A3 | −1.458129706 | NS |
| MTMR4 | −0.678532787 | NS | FLRT2 | −0.982089362 | NS |
| ASIC2 | −1.906526772 | NS | MANEAL | −1.301891932 | NS |
| **MYH3** | **−3.064466872** | **NS** | GPRIN3 | −1.516307763 | NS |
| NRXN2 | −1.351911452 | NS | FAM131C | −1.177204352 | NS |
| MADD | −0.739177659 | NS | SHC4 | −2.453382968 | NS |
| ELMOD1 | −1.395396128 | NS | **SRL** | **−1.710751408** | **NS** |
| OAS3 | −1.424153013 | NS | C11orf87 | −2.650466062 | NS |
| TBC1D30 | −1.541037732 | NS | CYP4X1 | −1.41397053 | NS |
| PHACTR1 | −1.246663978 | NS | GNG2 | −1.14775624 | NS |
| MDGA1 | −1.125611632 | NS | MYT1L | −2.032084319 | NS |
| SOBP | −0.912457321 | NS | CARMIL3 | −1.180812245 | NS |
| PCDHB6 | −1.420174397 | NS | MAPT | −1.894252952 | NS |
| PCDHB15 | −1.084879182 | NS | SLIT1 | −1.122370489 | NS |
| GRM6 | −1.370025912 | NS | PCDHB13 | −1.167548305 | NS |
| PODXL2 | −0.813566007 | NS | ERC2 | −0.975718121 | NS |
| PEX5L | −1.624859204 | NS | SHISA7 | −1.011391127 | NS |
| SLC4A3 | −1.274503402 | NS | C11orf95 | −0.652017772 | NS |
| APC2 | −1.569825162 | NS | PRKAR1B | −1.374317452 | NS |
| RTN4 | −0.675306193 | NS | SBK1 | −0.948657074 | NS |
| TACR1 | −1.665832741 | NS | JAKMIP3 | −0.927013444 | NS |
| QPCT | −1.040450208 | NS | FBLL1 | −1.49878319 | NS |
| PLCL1 | −1.270726637 | NS | NKAIN2 | −1.21247541 | NS |
| SLC1A4 | −1.382588205 | NS | VWC2 | −2.200514065 | NS |
| TNR | −2.582823125 | NS | FAM78B | −1.309319313 | NS |
| CHD5 | −1.435074018 | NS | INSYN2A | −1.913774634 | NS |
| DLGAP3 | −1.159358764 | NS | MSANTD1 | −1.341067332 | NS |
| DNAJC6 | −1.05661947 | NS | BTBD8 | −0.860463138 | NS |

TABLE 4-continued

Downregulated genes in Bupropion responders after treatment.

| gene_ID | logFC | PValue | gene_ID | logFC | PValue |
|---|---|---|---|---|---|
| KIF21B | −1.3360808 | NS | MAOA | −1.531005524 | NS |
| **HPCAL4** | **−1.488749573** | **NS** | PTPRT | −1.788539039 | NS |
| RIMS3 | −1.119098675 | NS | MYT1 | −1.296791657 | NS |
| PLPPR5 | −1.46673075 | NS | ZNF836 | −0.949448652 | NS |
| PLPPR4 | −2.082251585 | NS | GRM7 | −1.699339809 | NS |
| CHRNB4 | −1.48834376 | NS | ELAVL3 | −1.462914698 | NS |
| CRYGD | −3.452539712 | NS | ESRRG | −1.003014191 | NS |
| KLF7 | −0.877528149 | NS | AFAP1 | −0.758547013 | NS |
| CNR1 | −1.187086188 | NS | SLC30A10 | −1.879525589 | NS |
| SGIP1 | −1.239454627 | NS | CHRNG | −1.544708392 | NS |
| TRIM67 | −1.894297221 | NS | MVB12B | −1.106306871 | NS |
| ESRRB | −1.635356581 | NS | SLC6A17 | −2.433648708 | NS |
| BCL11A | −1.754987807 | NS | ADGRA1 | −1.373172017 | NS |
| IQSEC3 | −1.512916422 | NS | NOL4L | −0.737609084 | NS |
| MAPK8IP1 | −1.319759561 | NS | DACT3 | −0.903018543 | NS |
| SLITRK3 | −2.442803521 | NS | STMN3 | −1.144958616 | NS |
| ACVR2A | −0.607435554 | NS | MYH6 | −3.719672479 | NS |
| PTGFR | −2.026509755 | NS | DNM3 | −1.295360417 | NS |
| NXPH1 | −2.191338703 | NS | TMEM229B | −1.954937317 | NS |
| NEUROD4 | −1.412273161 | NS | RPS6KL1 | −1.019452207 | NS |
| GPR83 | −1.576322771 | NS | CACNA1E | −1.887984888 | NS |
| SLC12A5 | −1.631614291 | NS | **PEG3** | **−3.911713147** | **NS** |
| GDAP1L1 | −1.199699399 | NS | NTRK1 | −1.530266992 | NS |
| ATP8A1 | −1.064171276 | NS | ATL1 | −1.283560075 | NS |
| NDP | −2.195595223 | NS | TAFA2 | −1.303947821 | NS |
| SOX4 | −0.659162255 | NS | GRIN3A | −2.570461504 | NS |
| NRN1 | −0.95864031 | NS | SCAMP5 | −0.811287816 | NS |
| DOK4 | −0.829899665 | NS | RUSC2 | −0.99371396 | NS |
| RTN2 | −0.909901759 | NS | L1CAM | −1.210087819 | NS |
| NAPB | −1.050356155 | NS | GPRASP1 | −0.756176111 | NS |
| PCSK2 | −1.935505567 | NS | MAGEE1 | −0.84044562 | NS |
| ZNF436 | −0.852664294 | NS | SPRN | −1.245302248 | NS |
| MCF2L | −1.130244739 | NS | GDI1 | −0.592820544 | NS |
| TMEM35A | −1.273540644 | NS | TCEAL6 | −2.545961161 | NS |
| HIVEP3 | −1.261142498 | NS | MACO1 | −0.632447305 | NS |
| FBXL16 | −0.981588596 | NS | FAM155A | −0.658146564 | NS |
| GNAZ | −0.837899462 | NS | DISP3 | −1.132121705 | NS |
| ARHGAP22 | −2.022719878 | NS | PCDHA7 | −1.11142589 | NS |
| TMOD2 | −1.476671517 | NS | PCDHA5 | −1.075932224 | NS |
| DLL4 | −2.03847191 | NS | **ADGRG1** | **−0.70370797** | **NS** |
| CDKN2D | −1.37535975 | NS | INSYN1 | −1.208150868 | NS |
| SHC2 | −0.69331487 | NS | DPF3 | −1.334555455 | NS |
| SYT5 | −1.939768672 | NS | XKR4 | −1.301445493 | NS |
| CBFA2T3 | −1.14030916 | NS | SYT3 | −1.331689551 | NS |
| DPP6 | −1.174939755 | NS | ACKR1 | −1.506051499 | NS |
| NCAN | −1.327421809 | NS | MLLT11 | −1.038970933 | NS |
| KIF1A | −1.164752281 | NS | LBH | −0.800329912 | NS |
| UNC13A | −0.901820705 | NS | SOGA3 | −1.200187061 | NS |
| OLFM1 | −1.154100232 | NS | GNAT3 | −1.8743546 | NS |
| CALY | −1.348325725 | NS | UBE2QL1 | −1.574530217 | NS |
| MAP3K10 | −0.796456933 | NS | VAMP2 | −0.732724608 | NS |
| RGN | −1.436161252 | NS | PLXNA4 | −1.432421779 | NS |
| C1QL1 | −1.952433651 | NS | APOL6 | −1.251634334 | NS |
| GSE1 | −0.697313058 | NS | C14orf132 | −1.197944546 | NS |
| GALNT15 | −1.59164603 | NS | PNMA6A | −1.327922731 | NS |
| LANCL2 | −0.758187459 | NS | SMIM18 | −1.721049255 | NS |
| SNAP25 | −1.474913698 | NS | PCDHGA6 | −1.8707011 | NS |
| SYT11 | −0.768630905 | NS | TMEM179 | −1.493922905 | NS |
| VSTM2L | −1.007809194 | NS | FRRS1L | −1.312905869 | NS |
| SYT4 | −1.539750567 | NS | XKR7 | −1.25158674 | NS |
| ATP8A2 | −1.562531384 | NS | SCRT1 | −1.426655776 | NS |
| GPR12 | −2.093806234 | NS | PCDHGA4 | −1.156183752 | NS |
| TMCC2 | −0.919987328 | NS | SMIM22 | −1.921353421 | NS |
| DCLK1 | −1.159016346 | NS | MAGIX | −1.416531675 | NS |
| EPHB2 | −1.009283518 | NS | ANKRD34A | −1.242834616 | NS |
| NTS | −1.334957205 | NS | DOC2B | −2.03380502 | NS |
| DUSP26 | −1.670044532 | NS | **GRIN2B** | **−2.920742218** | **NS** |
| CTIF | −0.963756983 | NS | PIP4K2B | −0.616372816 | NS |
| GSTM3 | −1.177067826 | NS | NEFL | −0.855588326 | NS |
| KIDINS220 | −0.854170634 | NS | | | |

NS = not significant.

Lastly, expression levels in induced neurons that received Bupropion treatment were compared to those that received vehicle only, e.g., control neurons. Out of over 60,000 genes probed, 18 genes were found to be significantly (p≤0.05) upregulated in responders after treatment, but not upregulated in non-responders. These genes are presented in Table 5. Many other genes were also found to be upregulated although not significantly so, some of which are presented in the table. Of the genes probed, 57 were found to be significantly (p≤0.05) downregulated in responders after treatment, but not downregulated in non-responders. These genes are presented in Table 6. Many other genes were also found to be downregulated although not significantly so, some of which are presented in the table.

TABLE 5

Upregulated genes in Bupropion responders but not non-responders after treatment.

| gene_ID | logFC | PValue | gene_ID | logFC | PValue |
|---|---|---|---|---|---|
| CXCL11 | 1.358587498 | 0.005231725 | SCN9A | 0.652961085 | 0.044462789 |
| PTPRQ | 0.89002896 | 0.018081564 | MINDY3 | 0.190746779 | 0.044932218 |
| COX16 | 0.398519238 | 0.026606667 | ZFP69B | 0.256536317 | 0.046824204 |
| RSAD2 | 0.975293275 | 0.026606947 | ZNF221 | 0.325432655 | 0.049596306 |
| LLPH | 0.175810839 | 0.026874183 | CDK6 | 0.25785578 | NS |
| TSTD2 | 0.19321854 | 0.028984217 | MT2A | 1.37841779 | NS |
| HS3ST5 | 0.525093624 | 0.028999172 | GRPR | 0.62675507 | NS |
| CHMP4A | 0.393931682 | 0.031923817 | ESR2 | 0.48332454 | NS |
| PSD3 | 0.294728933 | 0.034363174 | PITX2 | 0.9302127 | NS |
| ARL17B | 0.448650167 | 0.037774775 | CA3 | 0.6571115 | NS |
| FGF1 | 0.744056318 | 0.040753088 | MT1E | 2.12307263 | NS |
| INMT | 0.815644259 | 0.04107423 | SEPTIN5 | 0.58766562 | NS |
| LHFPL3 | 0.845365303 | 0.041076888 | CORT | 0.64314357 | NS |

NS = not significant.

TABLE 6

Downregulated genes in Bupropion responders but not non-responders after treatment.

| gene_ID | logFC | PValue | gene_ID | logFC | PValue |
|---|---|---|---|---|---|
| LIN37 | −0.841149921 | 3.06E−05 | APOE | −0.475576768 | 0.036466348 |
| NFKBID | −0.604200688 | 0.003685448 | TYW1B | −0.283595463 | 0.037441749 |
| TCF7 | −0.390416754 | 0.005666754 | TOM1 | −0.22115371 | 0.039328923 |
| DUSP23 | −0.492702288 | 0.006214757 | GPR89A | −0.313527182 | 0.040776978 |
| TENT5B | −0.802098614 | 0.008132328 | HAUS8 | −0.337679425 | 0.040813288 |
| UGT3A2 | −0.488862067 | 0.009321582 | TNNI3 | −0.447253636 | 0.04085042 |
| CCDC51 | −0.244309464 | 0.012079592 | TJP3 | −0.428545974 | 0.041258334 |
| CTNS | −0.240420671 | 0.013463621 | RNASEK | −0.414834906 | 0.041364592 |
| PYCARD | −1.04998592 | 0.013981248 | MACROD1 | −0.407846567 | 0.041485982 |
| ABHD4 | −0.311055626 | 0.014582448 | DDX55 | −0.177007387 | 0.041521555 |
| TEKT3 | −0.800459798 | 0.015545465 | MAP4K1 | −0.454128214 | 0.041777603 |
| SMPDL3B | −0.748848378 | 0.022812161 | MADCAM1 | −0.634611517 | 0.042721026 |
| KLC3 | −0.853327537 | 0.023692875 | NMRK2 | −0.914961387 | 0.042934722 |
| PNKP | −0.217233163 | 0.024437941 | RARRES2 | −0.561445961 | 0.044126316 |
| SPNS1 | −0.702171614 | 0.024838304 | GABRD | −0.661000578 | 0.044432972 |
| FAM117A | −0.248500192 | 0.025868873 | CTSD | −0.304162915 | 0.044610728 |
| PPL | −0.393152334 | 0.026069274 | FBXO2 | −0.529736744 | 0.044969345 |
| ZNF425 | −0.23168104 | 0.026180649 | MT1X | −0.685808527 | 0.045842417 |
| MT2A | −0.77049102 | 0.02632325 | LRRC2 | −0.823382162 | 0.045853063 |
| PPP1R1B | −0.67697667 | 0.026677416 | SLC45A2 | −1.050263427 | 0.046871029 |
| CKS1B | −0.315320708 | 0.02807621 | KLHL21 | −0.272303106 | 0.047318696 |
| LGR6 | −0.609125893 | 0.028853165 | RILPL1 | −0.169220722 | 0.047560251 |
| ART5 | −0.508223193 | 0.030155652 | PSMB10 | −0.566946728 | 0.048107795 |
| ADRA2B | −0.745128354 | 0.031233579 | LHPP | −0.266911278 | 0.048445403 |
| ZNF394 | −0.197706159 | 0.031885505 | RABEP2 | −0.249553119 | 0.049224822 |
| ETV5 | −0.243186497 | 0.031953602 | LARGE2 | −0.565952568 | 0.049340025 |
| VWA2 | −0.824905931 | 0.033110679 | APOL1 | −0.7489224 | NS |
| CDC42BPG | −0.638641249 | 0.034205433 | ATP8B4 | −0.6945131 | NS |
| TRAF3IP2 | −0.341989037 | 0.035638975 | HIST1H1E | −1.4219311 | NS |
| TXNRD2 | −0.397068698 | 0.036129679 | CXCL11 | −1.175631 | NS |
| RAB43 | −0.766653544 | 0.036339642 | GOLGA8H | −0.5649952 | NS |

NS = not significant.

The same analysis was performed with a second cohort comprising 19 subjects with major depression, 4 of which were known responders to the depression drug Citalopram and 15 of which were known non-responders. Similarly, a third cohort of 7 subjects with major depression, 2 of which were known responders to the depression drug Mirtazapine and 5 of which were known non-responders were also analyzed, LCLs were reprogramed into iPSCs and differentiated to frontal cortical neuronal cells and RNA was analyzed both before and after administration of these two drugs. For the most part each drug produced a unique set of up- and downregulated genes, however, some common markers were found and are presented in bold in the tables.

Example 2: Morphological Differences are Observable in Neurons Derived from Antidepressant Responders and Non-Responders Immunohistochemical examination was carried out on the induced neuronal cells. Synaptic morphology and post-synaptic marker analysis were performed as described hereinabove (see Materials and Methods) and the imaging platform was shown to be highly reproducible through several repeats.

Figure 2A:
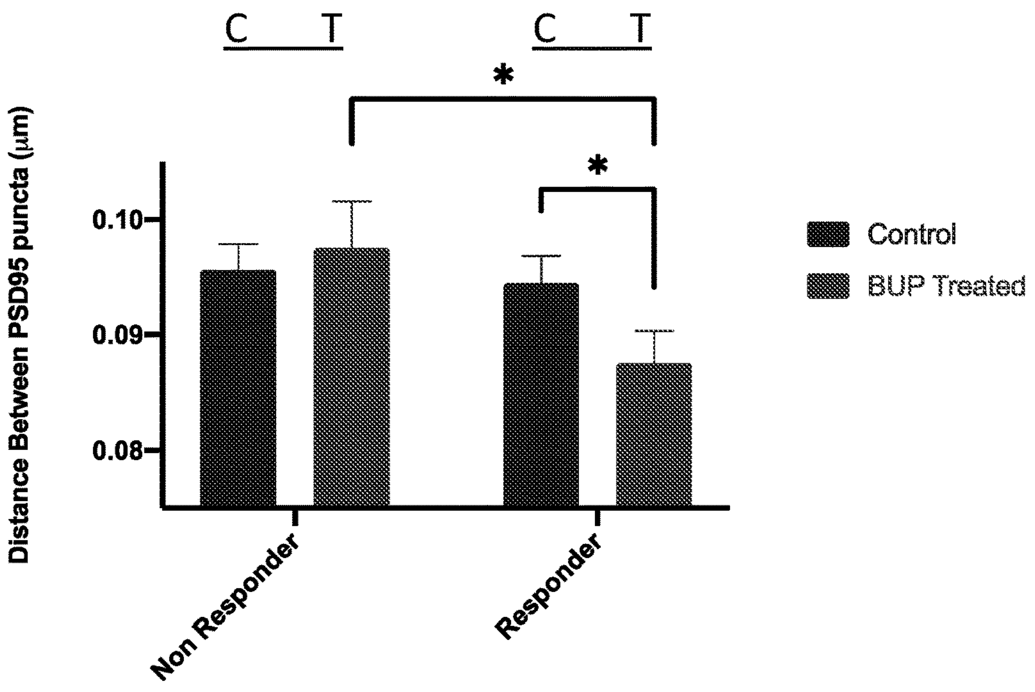
FIGS. 2A-2C. Analysis PSD95 puncta density (post-synaptic marker). Post-synaptic markers were analyzed using confocal microscopy in samples treated with (2A) Bupropion, (2B) Nortriptyline and (2C) Citalopram. Images were acquired with a 100× objective in z-stacks. Post-synaptic marker analysis was performed using CellProfiler. Total dendritic length was measured using Fiji software. (*=$p<0.05$; =$p<0.01$; *=$p<0.005$. Student t-test, for all figures)
Figure 2B:
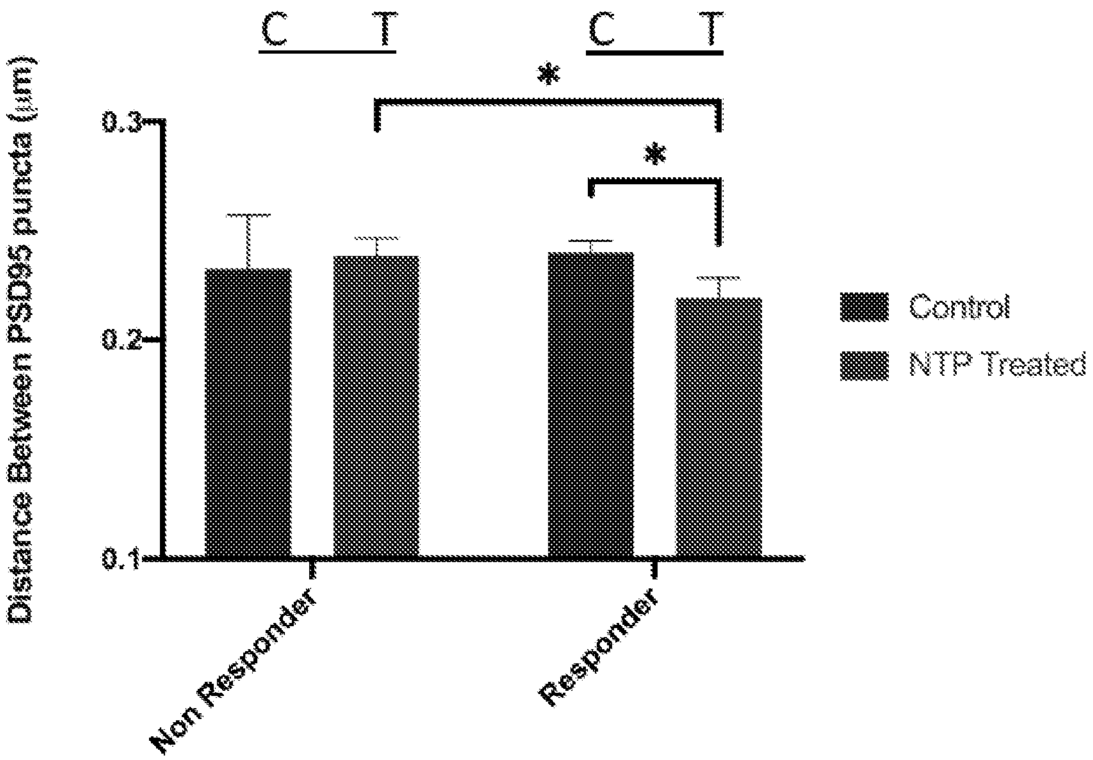
Figure 2C:
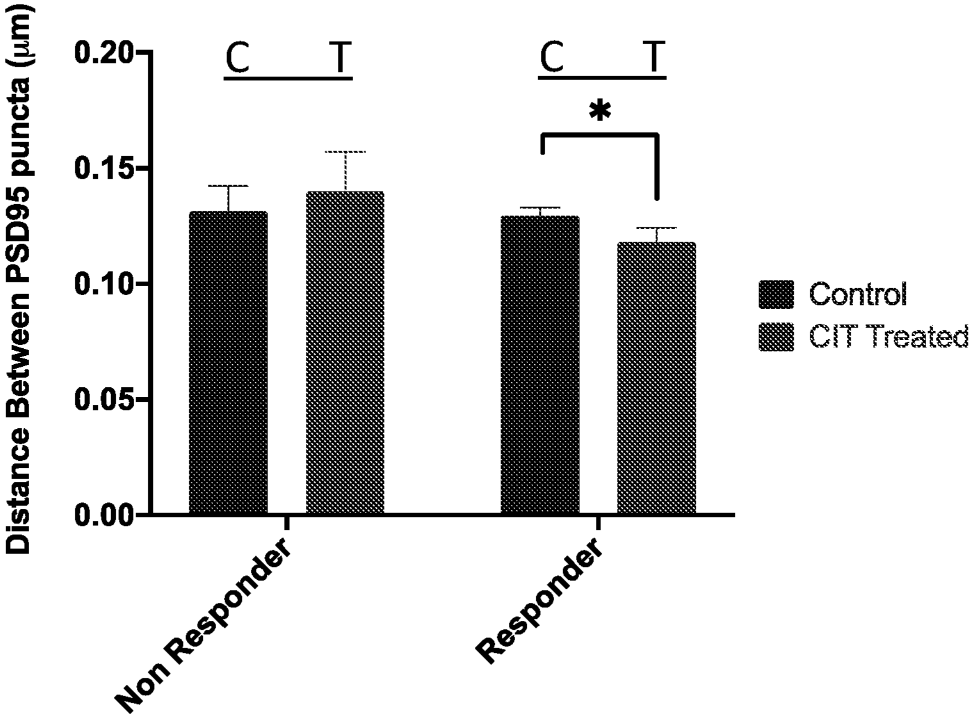

The density of post-synaptic terminals, as measured by the distance between PSD95 puncta 7 days after treatment, was significantly increased (interval distance between puncta is decreased) in responders to Bupropion after treatment with Bupropion (FIG. 2A). Not only was there a significant increase in density as compared to responder samples before treatment, but there was also an increase in density as compared to non-responders after treatment. Post-synaptic terminal density was also measured in samples from responders and non-responders to two other anti-depressive drugs Nortriptyline and Citalopram, both before and after treatment with those drugs. Similar to what was observed for Bupropion, there was a significant increase in density in responders after treatment with Nortriptyline (FIG. 2B) and Citalopram (FIG. 2C). Also similar to Bupropion the increase in density was also present when compared to non-responders after treatment.

Figure 3:
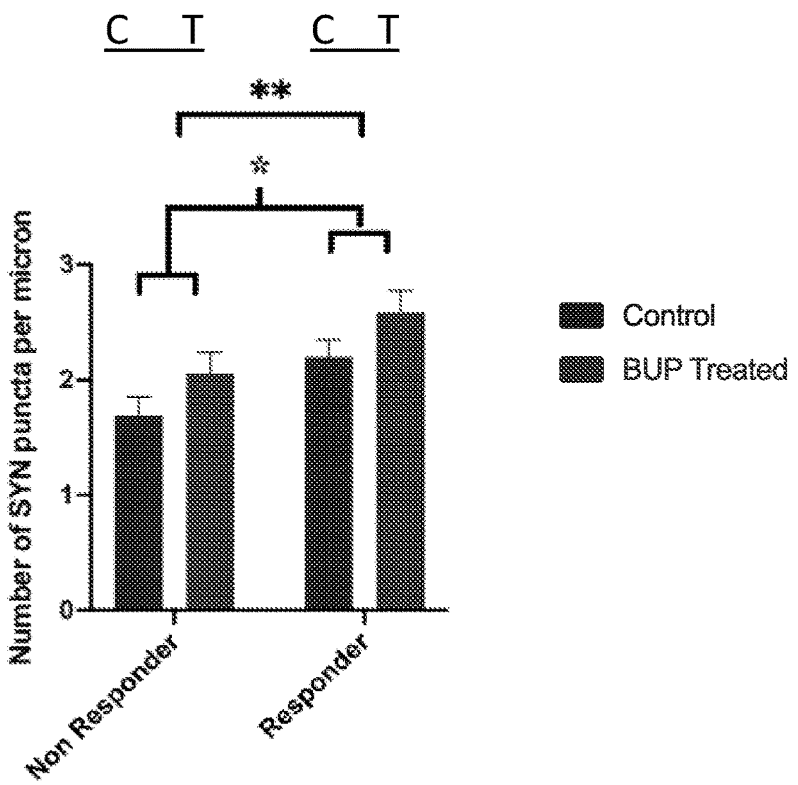
FIG. 3. Analysis of number of SYN puncta per micrometer (pre-synaptic marker). Pre-synaptic markers were analyzed using confocal microscopy in samples treated with Bupropion. Images were acquired with a 100× objective in z-stacks. Pre-synaptic marker analysis was performed using CellProfiler. Total dendritic length was measured using Fiji software.

Next, pre-synaptic terminals, as measured by Synapsin puncta density, were examined for Bupropion responders and non-responders. An increase in these neurons was observed in both responders and non-responders following treatment (FIG. 3). Further, the levels of pre-synaptic terminals were significantly higher in cells from responders both before and after treatment as compared to the non-responders.

Figure 4A:
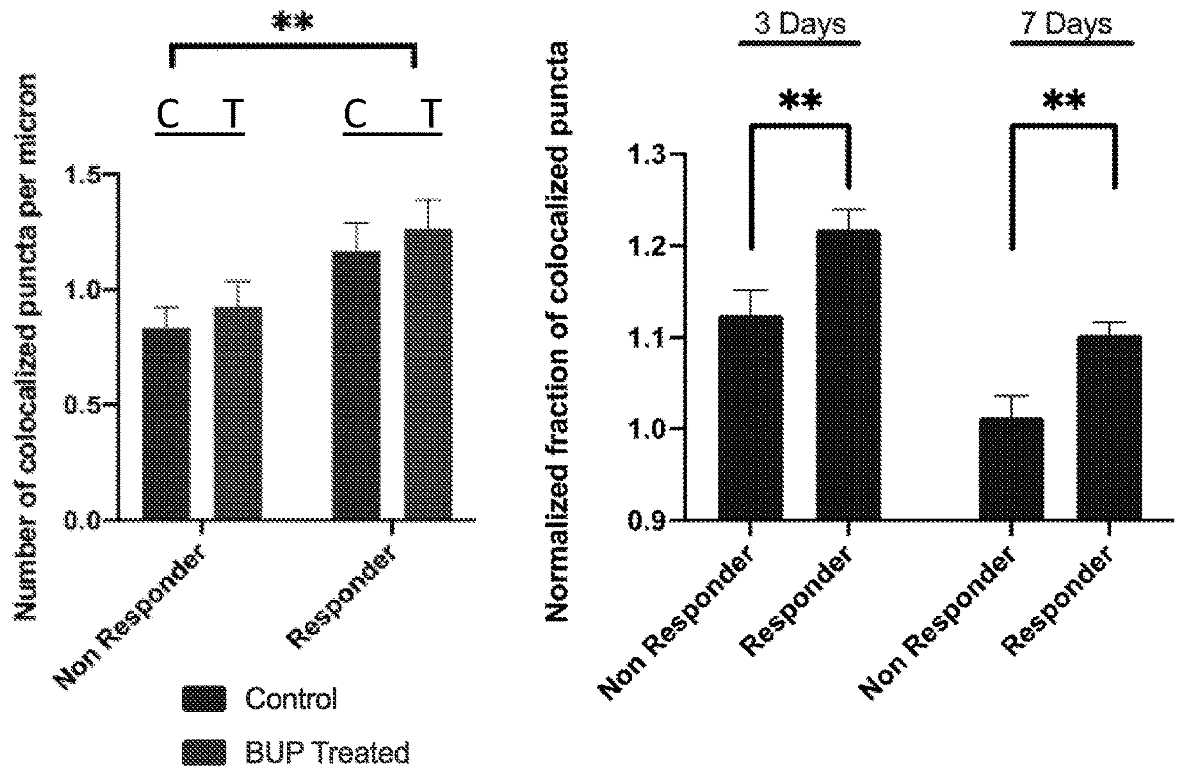
FIGS. 4A-4C. Analysis of number and fraction of colocalized pre-synaptic and post-synaptic puncta per micrometer. Post and pre-synaptic markers were analyzed using confocal microscopy in samples treated with (4A) Bupropion, (4B) Nortriptyline and (4C) Citalopram. Images were acquired with a 100× objective in z-stacks. Neuronal and synaptic morphology was assessed using the Neurolucida software and post-synaptic marker analysis was performed using CellProfiler. Total dendritic length was measured using Fiji software. 4A shows measurements after 7 days of treatment (left) and normalized colocalization after 3 and 7 days of treatment (right).
Figure 4B:
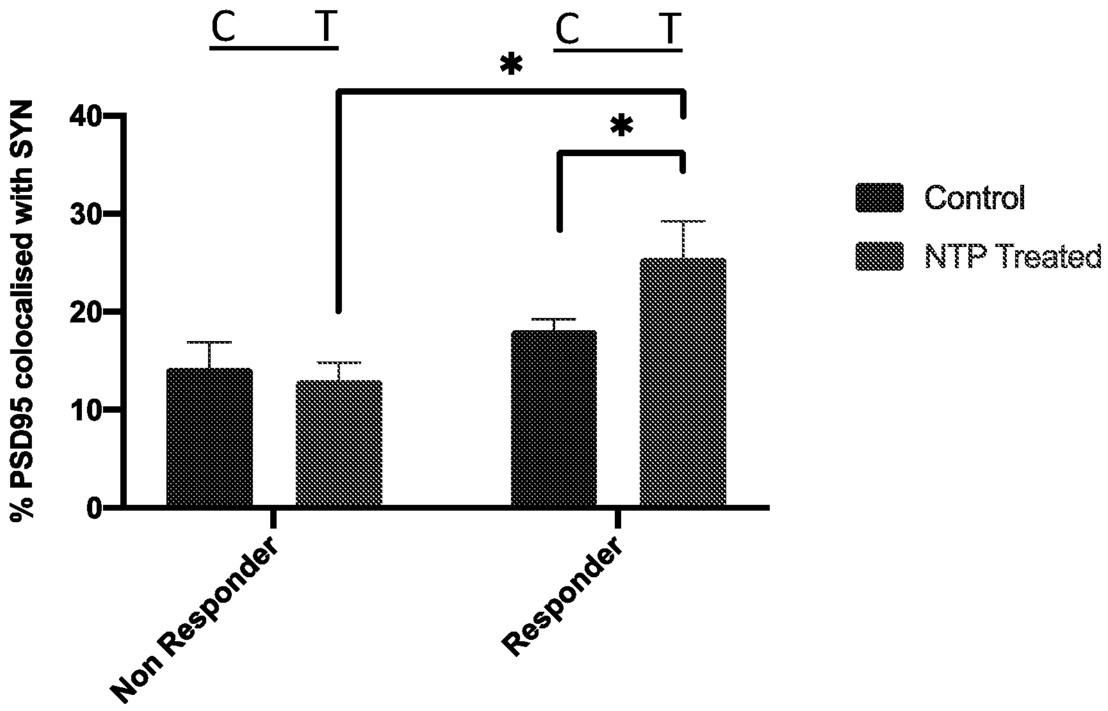
Figure 4C:
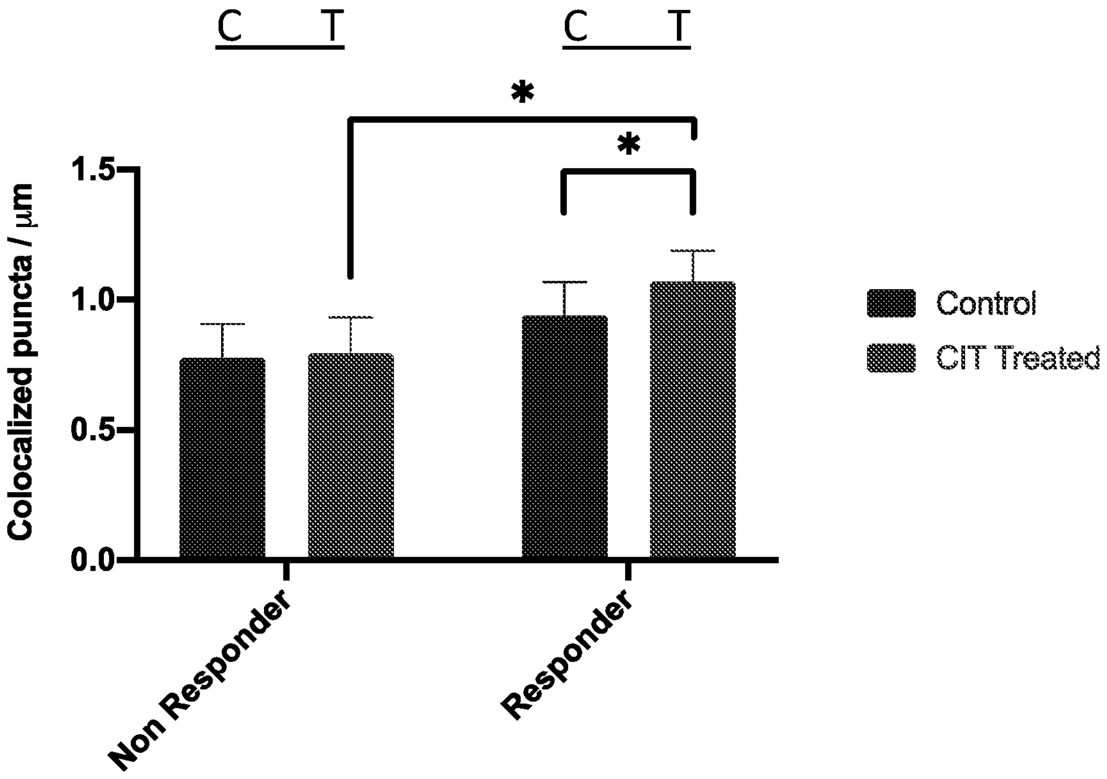

This increase in Synapsin positive terminals in responder neurons translates into an increase in intact synapses, as defined by colocalization of pre- and post-synaptic terminals (FIG. 4A). This increase was seen both at baseline and after treatment. Both responders and non-responders showed increased intact synapses as compared to the untreated samples. Further, these differences were significant already at 3 days (FIG. 4A, right) after treatment and were still present 7 days after treatment (FIG. 4A, left and right). These results were even more pronounced for Nortriptyline treatment after 7 days (FIG. 4B). Responders to Nortriptyline already had slightly increased numbers of intact synapses before treatment. Intact synapses however were significantly upregulated in responders after treatment, while non-responders showed no change or even a slight decrease. As a result, responders showed significantly more intact synapses than non-responders after treatment. Further, the number of intact puncta was significantly higher in cells from responders after treatment as compared to the non-responders after treatment. The same pattern was seen when induced neurons from responders and non-responders to Citalopram were examined both before and after treatment with this drug (FIG. 4C). At baseline responders showed slightly greater numbers of intact synapses, but while non-responders showed no change in intact synapses after treatment with Citalopram, responders showed a significant increase in total intact synapse number after treatment. Once again, this results in responders showing more intact synapses than non-responders after treatment. Further, the number of intact puncta was significantly higher in cells from responders after treatment as compared to the non-responders after treatment.

Figure 5:
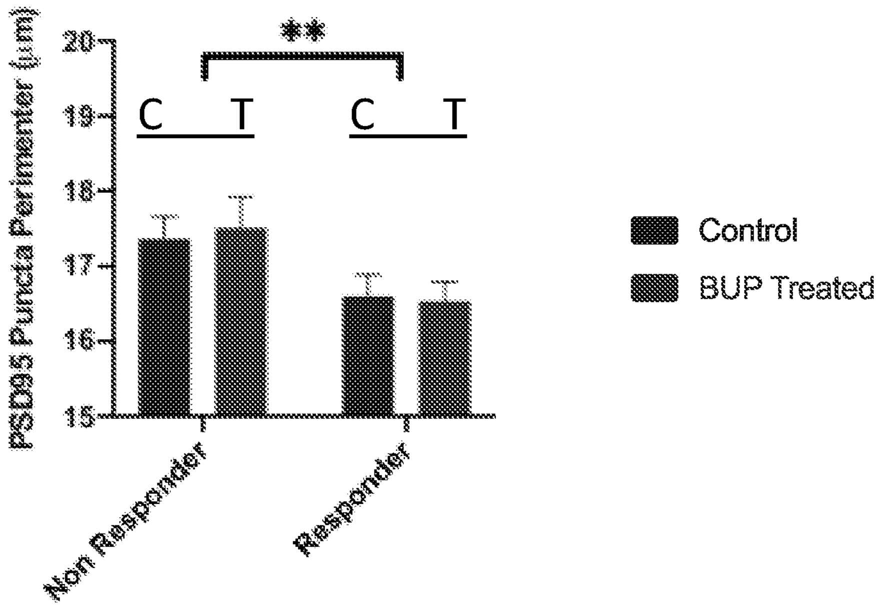
FIG. 5. Analysis of PSD95 puncta perimeter (post-synaptic marker). Post-synaptic markers were analyzed using microscopy in samples treated with Bupropion. Images were acquired with a 100× objective in z-stacks. Neuronal and synaptic morphology was assessed using the Neurolucida software and post-synaptic marker analysis was performed using CellProfiler. Total dendritic length was measured using Fiji software.
Figure 6:
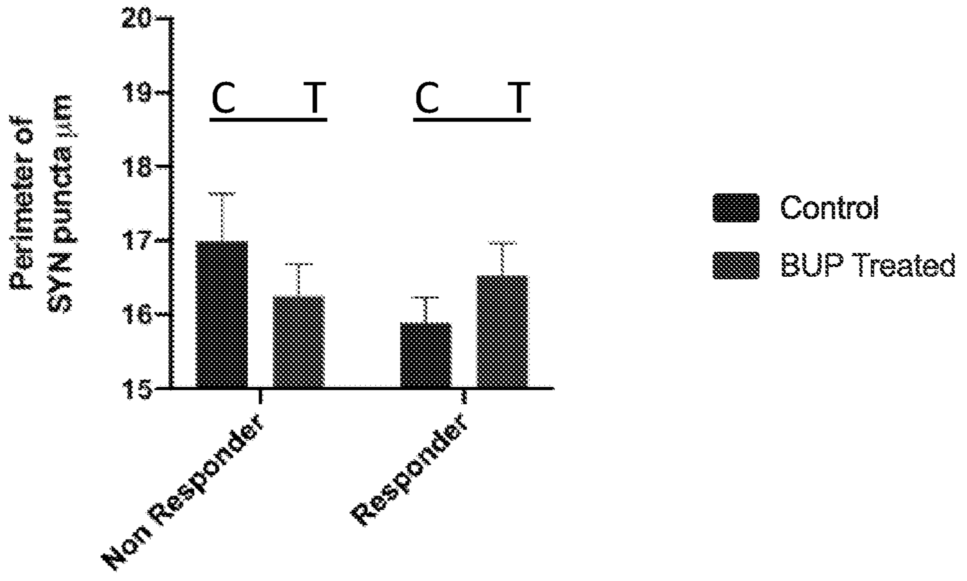
FIG. 6. Analysis of SYN puncta perimeter (pre-synaptic marker). Pre-synaptic markers were analyzed using confocal microscopy in samples treated with Bupropion. Neurons were stained and images were acquired with a 100× objective in z-stacks. Neuronal and synaptic morphology was assessed using the Neurolucida software and pre-synaptic marker analysis was performed using CellProfiler. Total dendritic length was measured using Fiji software.

The size of PSD95 puncta was also measured and was found to be reduced in cells from responders at baseline and after treatment, although the treatment had no significant effect (FIG. 5). Conversely, at baseline the size of Synapsin puncta was smaller in cells derived from responders as compared to non-responders (FIG. 6). However, treatment caused a reduction in puncta perimeter size in cells from non-responders and an increase in puncta perimeter size in cells from responders, suggesting that this marker may be useful before treatment and as a dynamic marker when comparing before and after.

Figure 7:
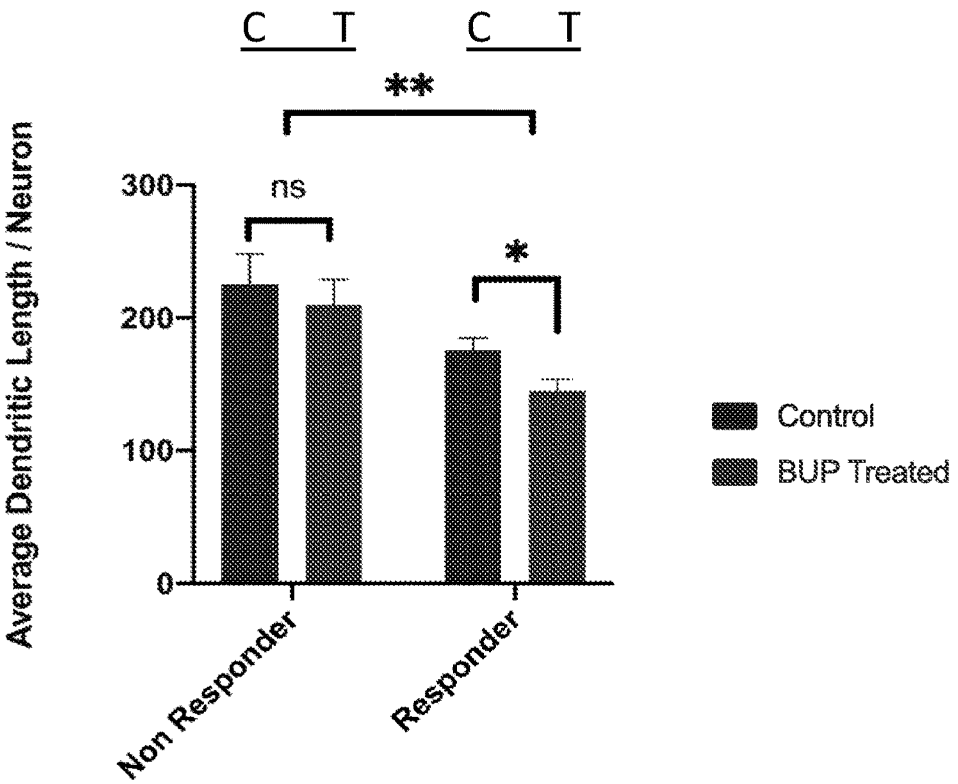
FIG. 7. Analysis of dendritic arborization. Dendritic arborization was analyzed using confocal microscopy in samples treated with Bupropion. Images for dendritic arborization were acquired with a 20× objective in z-stacks and analyzed using Neurolucida software.
Figure 8:
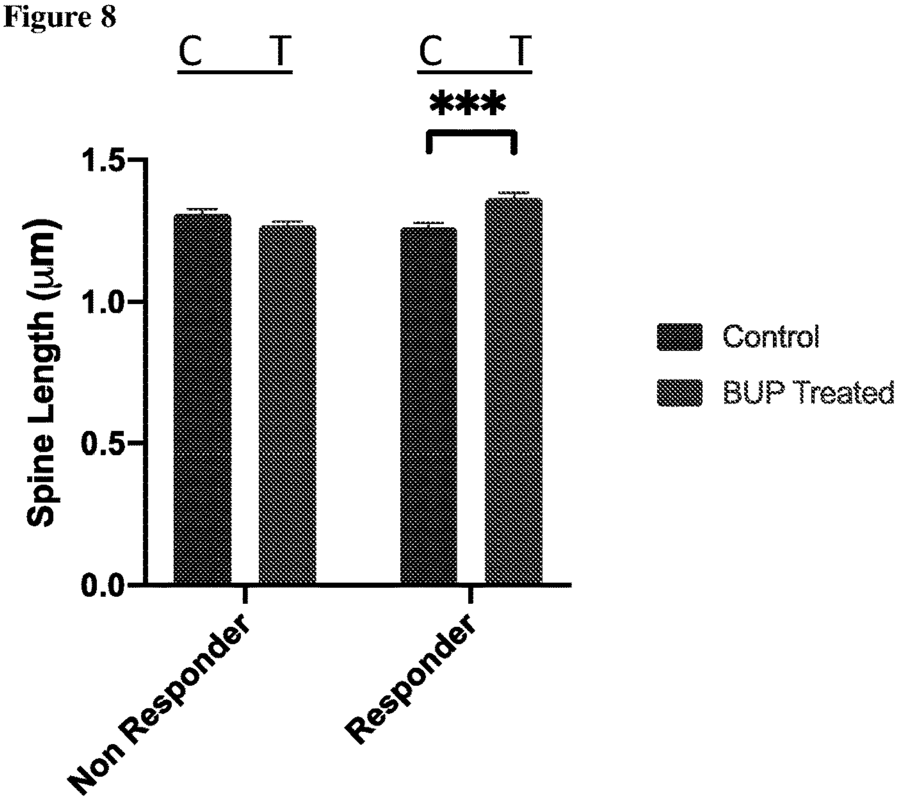
FIG. 8. Average dendritic spine length. Dendritic spine length was analyzed using confocal microscopy in samples treated with Bupropion. For imaging of dendritic spines, images were acquired using the Nikon Confocal A1R with a 60× objective and a 2× digital zoom in z-stacks. Analysis was performed using Neurolucida software.
Figure 9A:
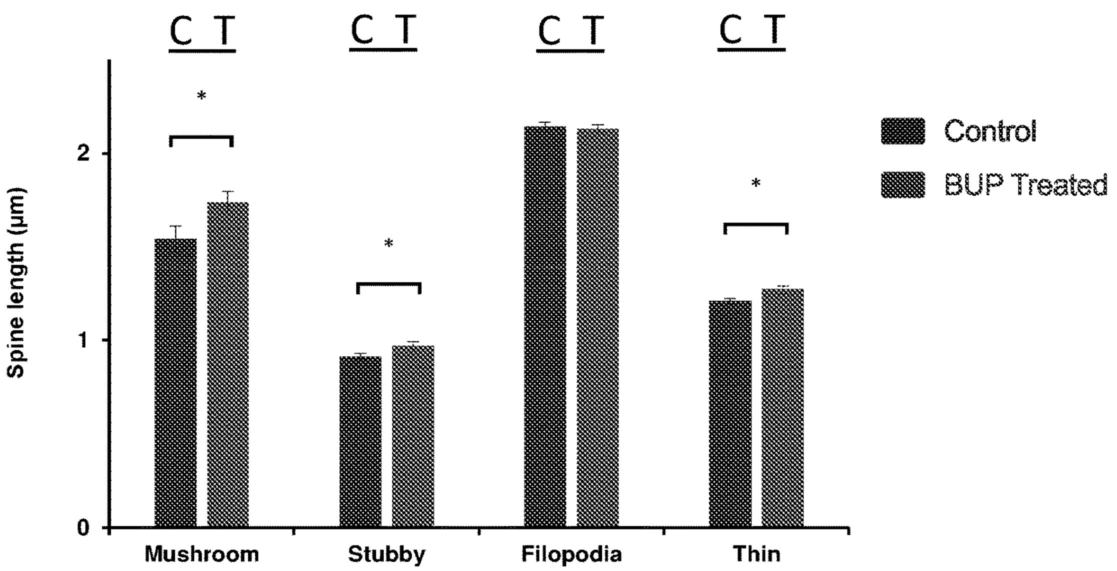
FIGS. 9A-9B. Average dendritic spine length in specific spine types. Dendritic spine length for four spine types was analyzed in cells from (9A) responders to Bupropion and (9B) non-responders to Bupropion using confocal microscopy. For imaging of dendritic spines, images were acquired using the Nikon Confocal A1R with a 60× objective and a 2× digital zoom in z-stacks. Analysis was performed using Neurolucida software.
Figure 9B:
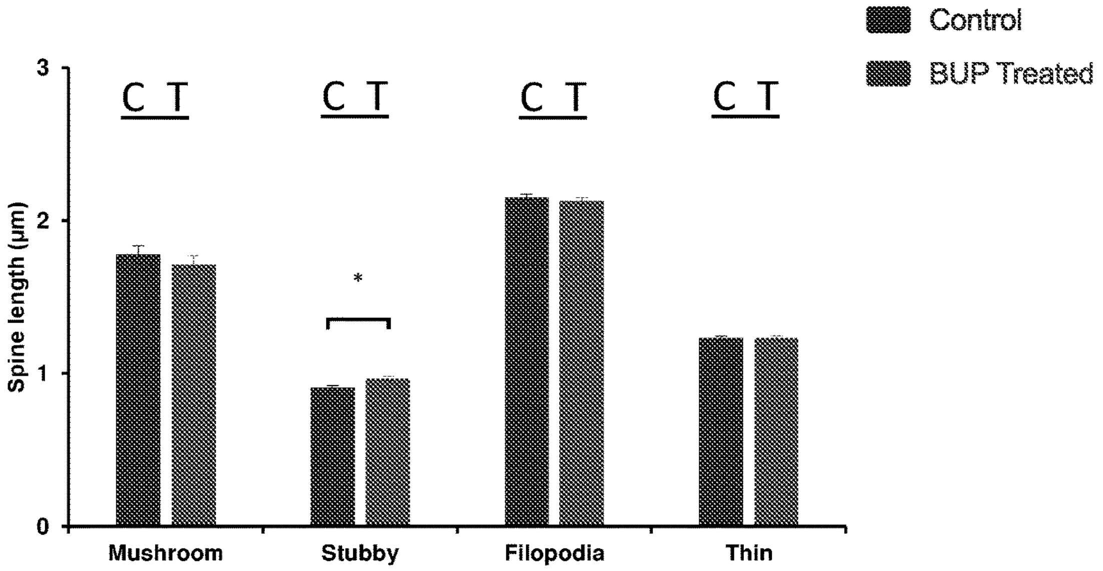

Dendritic arborization was also analyzed. First, dendrite length was measured; the dendrites of cells derived from responders were found to be shorter at baseline (FIG. 7). This difference became exacerbated after treatment, which caused a significant decrease in dendritic length in neurons derived from responders and did not in cells derived from non-responders. The average length of dendritic spines was also analyzed. A significant increase in total dendritic spine length in cells derived from responders after treatment was observed, while no difference was observed in cells derived from non-responders (FIG. 8). At baseline, no difference was observable between the two cell types. When four specific spine types, mushroom, stubby, filopodia and thin, were examined individually, a significant increase in the number of mushroom, stubby and thin spines was seen in responder's cells after treatment (FIG. 9A). Cells from non-responders only showed an increase in the number of stubby spines after treatment (FIG. 9B), and no significant difference between cells of responders and non-responders was observed at baseline.

Example 3: Analysis of Neurons Derived Directly from T Cells

Similar RNA and histological analyses are performed on neurons that are derived directly from responder and non-responder T cells, without initial conversion to iPSCs. A protocol such as that provided in Tanabe et al., 2018 "Transdifferentiation of human adult peripheral blood T cells into neurons", or a similar protocol is employed. RNA sequencing analysis is performed and markers both before and after drug administration are investigated. Morphological markers including pre- and post-synaptic markers as well as dendritic arborization are monitored.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A method of determining suitability of a subject suffering from depression to be treated with Bupropion, comprising:

a) providing a neuronal cell derived from a non-neuronal cell from said subject;

b) assessing said neuronal cell for at least one biomarker, wherein said biomarker is selected from a group consisting of pre-synaptic puncta perimeter length, dendritic spine length, and dendrite length;

c) administering Bupropion to said neuronal cell; and assessing Bupropion's effect on said at least one biomarker, wherein a. downregulation of dendrite length, upregulation of dendritic spine length, or upregulation of pre-synaptic puncta perimeter length indicates suitability of said subject to be treated with Bupropion; and b. downregulation of pre-synaptic puncta perimeter length, or dendritic spine length indicates unsuitability of said subject to be treated with Bupropion;

thereby determining suitability of a subject to be treated with Bupropion.

2. The method of claim 1, further comprising assessing said neuronal cell for at least one additional biomarker, wherein said at least one additional biomarker is expression of at least one gene selected from: CXCL11, PTPRQ, COX16, RSAD2, LLPH, TSTD2, HS3ST5, CHMP4A, PSD3, ARL17B, FGF1, INMT, LHFPL3, SCN9A, MINDY3, ZFP69B, and ZNF221, wherein upregulation of expression of said at least one gene indicates suitability of said subject to be treated with said psychiatric drug.

3. The method of claim 1, further comprising assessing said neuronal cell for at least one additional biomarker, wherein said at least one additional biomarker is expression of at least one gene selected from: LIN37, NFKBID, TCF7, DUSP23, TENT5B, UGT3A2, CCDC51, CTNS, PYCARD, ABHD4, TEKT3, SMPDL3B, KLC3, PNKP, SPNS1, FAM117A, PPL, ZNF425, MT2A, PPP1R1B, CKS1B, LGR6, ART5, ADRA2B, ZNF394, ETV5, VWA2, CDC42BPG, TRAF3IP2, TXNRD2, RAB43, APOE, TYW1B, TOM1, GPR89A, HAUS8, TNNI3, TJP3, RNASEK, MACROD1, DDX55, MAP4K1, MADCAM1, NMRK2, RARRES2, GABRD, CTSD, FBXO2, MT1X, LRRC2, SLC45A2, KLHL21, RILPL1, PSMB10, LHPP, RABEP2, and LARGE2, wherein downregulation of expression of said at least one gene indicates suitability of said subject to be treated with said psychiatric drug.

4. The method of claim 1, further comprising administering said psychiatric drug to a subject determined to be suitable to be treated with said psychiatric drug.

5. The method of claim 1, wherein said neuron is a cortical neuron.

6. The method of claim 1, wherein said neuronal cell is derived from:

a. an induced pluripotent stem cell (iPSC) derived from a non-neuronal cell from said subject;

b. a blood cell;

c. a peripheral blood mononuclear cell (PBMC); or d. a lymphoblast.

7. The method of claim 1, wherein said at least one biomarker obtained from said neuronal cell is used alone or combined with said subject's clinical, genetic or biological background to determine suitability of said subject to be treated by said psychiatric drug.

8. The method of claim 1, wherein said depression comprises major depression, unipolar depression or both.

9. The method of claim 1, wherein said pre-synaptic puncta are defined by expression of synapsin.

10. The method of claim 5, wherein said cortical neuron is a frontal cortical neuron.

11. A method of determining suitability of a subject suffering from depression to be treated with a psychiatric drug selected from Bupropion, Nortriptyline and Citalopram, comprising:

a) providing a neuronal cell derived from a non-neuronal cell from said subject;

b) assessing said neuronal cell for at least one biomarker, wherein said biomarker is selected from a group consisting of pre-and post-synaptic colocalized puncta number, density of post-synaptic puncta and expression of Paired-like homeodomain transcription factor 2 (PITX2);

c) administering said psychiatric drug to said neuronal cell; and assessing said psychiatric drug's effect on said at least one biomarker, wherein upregulation of pre-and post-synaptic colocalized puncta number, upregulation of density of post-synaptic puncta or upregulation of expression of PITX2, indicates suitability of said subject to be treated with said psychiatric drug;

thereby determining suitability of a subject to be treated with a psychiatric drug.

12. The method of claim 11, further comprising administering said psychiatric drug to a subject determined to be suitable to be treated with said psychiatric drug.

13. The method of claim 11, wherein said neuron is a cortical neuron.

14. The method of claim 13, wherein said cortical neuron is a frontal cortical neuron.

15. The method of claim 11, wherein said neuronal cell is derived from:

a. an induced pluripotent stem cell (iPSC) derived from a non-neuronal cell from said subject;

b. a blood cell;

c. a peripheral blood mononuclear cell (PBMC); or d. a lymphoblast.

16. The method of claim 11, wherein said assessing comprises measuring expression of said PITX2 in said neuronal cell and wherein said expression is RNA expression, protein expression or both, optionally wherein said expression is RNA expression and said assessing comprises RNA sequencing, RNA microarray analysis, PCR or microscopy analysis.

17. The method of claim 11, wherein said at least one biomarker obtained from said neuronal cell is used alone or combined with said subject's clinical, genetic or biological background to determine suitability of said subject to be treated by said psychiatric drug.

18. The method of claim 11, wherein said depression comprises major depression, unipolar depression or both.

19. The method of claim 11, wherein (a) said pre-synaptic puncta are defined by expression of synapsin; (b) said post-synaptic puncta are defined by expression of PSD95; or (c) both (a) and (b).

20. The method of claim 11, wherein said psychiatric drug is Bupropion.

* * * * *